(12) United States Patent
Thompson et al.

(10) Patent No.: US 8,969,009 B2
(45) Date of Patent: *Mar. 3, 2015

(54) IDENTIFICATION OF DISCRIMINANT PROTEINS THROUGH ANTIBODY PROFILING, METHODS AND APPARATUS FOR IDENTIFYING AN INDIVIDUAL

(76) Inventors: Vicki S. Thompson, Idaho Falls, ID (US); Jeffrey A. Lacey, Idaho Falls, ID (US); Cynthia A. Gentillon, Idaho Falls, ID (US); William A. Apel, Jackson, WY (US)

( * ) Notice: Subject to any disclaimer, the term of this patent is extended or adjusted under 35 U.S.C. 154(b) by 1259 days.

This patent is subject to a terminal disclaimer.

(21) Appl. No.: 12/586,109

(22) Filed: Sep. 17, 2009

(65) Prior Publication Data

US 2011/0065594 A1  Mar. 17, 2011

(51) Int. Cl.
G01N 33/53     (2006.01)
G01N 33/68     (2006.01)

(52) U.S. Cl.
CPC ................................ G01N 33/6845 (2013.01)
USPC ........................................................ 435/7.1

(58) Field of Classification Search
None
See application file for complete search history.

(56) References Cited

U.S. PATENT DOCUMENTS

| | | | |
|---|---|---|---|
| 566,558 A | 8/1896 | Bell | |
| 4,235,869 A | 11/1980 | Schwarzberg | |
| 4,542,104 A | 9/1985 | Stryer et al. | |
| 4,880,750 A | 11/1989 | Francoeur | |
| 5,238,652 A | 8/1993 | Sun et al. | |
| 5,270,167 A * | 12/1993 | Francoeur ..................... | 435/7.21 |
| 5,281,521 A | 1/1994 | Trojanowski et al. | |
| 5,445,934 A | 8/1995 | Fodor et al. | |
| 5,471,549 A | 11/1995 | Kurosu et al. | |
| 5,529,922 A | 6/1996 | Chapman et al. | |
| 5,541,113 A | 7/1996 | Siddigi et al. | |
| 5,605,662 A | 2/1997 | Heller et al. | |
| 5,744,305 A | 4/1998 | Fodor et al. | |
| 5,858,801 A | 1/1999 | Brizzolara | |
| 5,885,780 A | 3/1999 | Olivera et al. | |
| 5,888,813 A | 3/1999 | Endl et al. | |
| 6,103,479 A | 8/2000 | Taylor | |
| 6,553,135 B1 | 4/2003 | Douglass et al. | |
| 6,591,193 B2 | 7/2003 | Krebs et al. | |
| 6,591,196 B1 | 7/2003 | Yakhini et al. | |
| 6,906,104 B2 | 6/2005 | Schostarez et al. | |
| 6,965,704 B2 | 11/2005 | Kaushikkar et al. | |
| 6,980,677 B2 | 12/2005 | Niles et al. | |
| 6,989,276 B2 | 1/2006 | Thompson et al. | |
| 7,219,016 B2 | 5/2007 | Rimm et al. | |
| 7,682,797 B2 * | 3/2010 | Thompson et al. ............ | 435/7.1 |
| 7,682,798 B2 | 3/2010 | Thompson et al. | |
| 7,695,919 B2 * | 4/2010 | Apel et al. ..................... | 435/7.1 |
| 8,014,577 B2 | 9/2011 | Bouchard et al. | |
| RE44,031 E | 2/2013 | Apel et al. | |
| RE44,539 E | 10/2013 | Thompson et al. | |
| 2002/0127623 A1 * | 9/2002 | Minshull et al. ............. | 435/7.92 |
| 2002/0168699 A1 | 11/2002 | Thompson et al. | |
| 2003/0073149 A1 | 4/2003 | Archer et al. | |
| 2004/0063220 A1 * | 4/2004 | Lebrun ......................... | 436/518 |
| 2004/0085443 A1 | 5/2004 | Kallioniemi et al. | |
| 2005/0042696 A1 | 2/2005 | Kovalenko | |
| 2005/0047678 A1 | 3/2005 | Jones et al. | |
| 2005/0054118 A1 | 3/2005 | Lebrun | |
| 2005/0202421 A1 | 9/2005 | Hirsch et al. | |
| 2005/0208529 A1 | 9/2005 | Winther et al. | |
| 2005/0214882 A1 | 9/2005 | Zou et al. | |
| 2006/0057741 A1 | 3/2006 | Thompson et al. | |
| 2006/0115429 A1 | 6/2006 | Afeyan et al. | |
| 2006/0223131 A1 | 10/2006 | Schweitzer et al. | |
| 2006/0257396 A1 | 11/2006 | Jacobsen | |
| 2007/0190585 A1 | 8/2007 | Apel et al. | |
| 2008/0058215 A1 | 3/2008 | Kim et al. | |
| 2008/0144899 A1 | 6/2008 | Varma et al. | |
| 2008/0200796 A1 * | 8/2008 | Graham et al. ............... | 600/411 |
| 2008/0286881 A1 * | 11/2008 | Apel et al. .................... | 436/514 |
| 2008/0298667 A1 | 12/2008 | Lassahn et al. | |
| 2008/0300796 A1 | 12/2008 | Lassahn et al. | |
| 2009/0042213 A1 | 2/2009 | Hoofnagle et al. | |
| 2009/0047281 A1 * | 2/2009 | Sherman .................... | 424/134.1 |
| 2011/0065594 A1 | 3/2011 | Thompson et al. | |
| 2011/0065601 A1 | 3/2011 | Apel et al. | |

FOREIGN PATENT DOCUMENTS

| | | |
|---|---|---|
| CA | 2685997 | 10/2013 |
| GB | 2190490 | 11/1987 |
| JP | 61122223 | 6/1986 |
| WO | 9729206 | 8/1977 |
| WO | 86/02734 | 5/1986 |

(Continued)

OTHER PUBLICATIONS

Identity Sciences, "Identity Sciences LLC Introduces a Non-DNA Human Identification Test with Results Available in Two Hours," Apr. 16, 2008. Retrieved from the internet May 10, 2011: <URL: http://www.identitysciences.com/releases/IDS_04-16-08.pdf> p. 1.

(Continued)

Primary Examiner — Ann Lam
(74) Attorney, Agent, or Firm — Taylor English Duma LLP

(57) ABSTRACT

A method for determining a plurality of proteins for discriminating and positively identifying an individual based from a biological sample. The method may include profiling a biological sample from a plurality of individuals against a protein array including a plurality of proteins. The protein array may include proteins attached to a support in a preselected pattern such that locations of the proteins are known. The biological sample may be contacted with the protein array such that a portion of antibodies in the biological sample reacts with and binds to the proteins forming immune complexes. A statistical analysis method, such as discriminant analysis, may be performed to determine discriminating proteins for distinguishing individuals. Proteins of interest may be used to form a protein array. Such a protein array may be used, for example, to compare a forensic sample from an unknown source with a sample from a known source.

24 Claims, 1 Drawing Sheet

(56) References Cited

FOREIGN PATENT DOCUMENTS

| WO | 8602734 | 5/1986 | | |
|---|---|---|---|---|
| WO | 90/05296 | 5/1990 | | |
| WO | WO 97/29206 | * | 2/1997 | .............. C12P 19/30 |
| WO | 97/29206 | 8/1997 | | |
| WO | 9831839 | 7/1998 | | |
| WO | 9838490 | 9/1998 | | |
| WO | 9938985 | 8/1999 | | |
| WO | 03052422 | 6/2003 | | |
| WO | 2007031874 | 3/2007 | | |
| WO | 2008118558 | 10/2008 | | |
| WO | 2008144085 | 11/2008 | | |
| WO | 2011037827 | 3/2011 | | |

OTHER PUBLICATIONS

PCT International Search Report and Written Opinion of the International Searching Authority for PCT/US10/49227, dated May 25, 2011, 14 pages.

Bernstein et al., Cellular Protein and RNA Antigens in Autoimmune Disease, 2 Mol. Biol. Med. 105-120 (1984).

Cabilly, Combinatorial Peptide Library Protocols, Humana Press, 304 p. p., 129 154 (1997).

Cwirla et al., Peptides on Phage: A Vast Library of Peptides for Identifying Ligands, 87 Proc. Nat'l Acad. Sci. USA 6378-6382 (1990).

Devlin et al., Random Peptide Libraries: A Source of Specific Protein Binding Molecules, 249 Science 404-406 (1990).

Fodor, P. S., 277 Science 393-395 (1997).

Francoeur et al., Identification of Ki (Ku, p70/p80) Autoantigens and Analysis of Anti-Ki Autoantibody Reactivity, 136 J. Immunol. 1648 (1986).

Francoeur, A. M., Antibody Fingerprinting: A Novel Method for Identifying Individual People and Animals, 6 Bio/technology 821-825 (1988).

Good et al., Hydrogen Ion Buffers, 24 Methods Enzymology 53-68 (1972).

Han et al., Detection of Analyte Binding to Microarrays Using Gold Nanoparticle Labels and a Desktop Scanner, 3 Lab Chip 329; 329-332 (2003).

Hemmila, I., Fluoroimmunoassays and Immunofluorometric Assays, 31 Clin. Chem. 359 (1985).

Invitrogen, "Antibody Profiling on Invitrogen ProtoArray, High-Density Protein Microarrays," Application Note, <www.invitrogen.com/protoarray> (2005) 6 pages.

Invitrogen, "ProtoArray Immune Response Biomarker Profiling Application Kit," User Manual, Catalog No. PA016, Version A, Sep. 13, 2006, 36 pages.

Kemeny et al., Elisa and Other Solid Phase Immunoassays, (John Wiley & Sons Ltd.) (1988).

Lam et al., A New Type of Synthetic Peptide Library for Identifying Ligand-binding Activity, 354 Nature 82-84 (1991).

Leland et al., Electrogenerated Chemiluminescence: An Oxidative-Reduction Type ECL Reactions Sequence Using Triprophyl Amine, 137 J. Electrochemical Soc. 3127-3131 (1990).

Michaud, et al., "Biomarker Identification Using ProtoArray High Density Protein Microarrays: Profiling Auto-antibodies in Disease," Application Note, <www.invitrogen.com/protoarray> (2005) 6 pages.

Persoon, T., "Immunochemical Assays in the Clinical Laboratory," 5 Clinical Laboratory Science 31 (1992).

Petrik, J., "Microarray technology: the future of blood testing?" Review, Blackwell Science Ltd. Vox Sanguinis (2001) 80, pp. 1-11.

Predki et al., "Protein microarrays: A new tool for profiling antibody cross-reactivity," Human Antibodies, IOS Press, 14 (2005) pp. 7-15.

Ryder, Stacey, "Microarrays Provide Fast and Sensitive Genetic Fingerprint for Forensic Investigations," Affymetrix Microarray Bulletin, Sequence Analysis, vol. 1, Issue 4, pp. 1-5 (Oct. 2005).

Santangelo et al., Cloning of Open Reading Frames and Promoters from the *Saccharomyces cerevisiae* Genome: Construction of Genomic Libraries of Random Small Fragments, 46 Gene 181-186 (1986).

Scott et al., Searching for Peptide Ligands with an Epitope Library, 249 Science 386 (1990).

Stites et al., Basic and Clinical Immunology, (1994).

Thompson et al., Antibody profiling as an identification tool for forensic samples, 3576 Investigation and Forensic Science Technologies 52-59 (1999).

Thompson et al., Fiber-Optic Immunosensor for the Detection of Fumonisin B1, 44 J. Agric. Food Chem. 1041-1046 (1996).

Unger et al., Individual-specific Antibody Profiles as a Means of Newborn Infant Identification, 15 J. Perinatology 152-155 (1995).

Wong, S. S., Chemistry of Protein Conjugation and Cross Linking CRC Press, 340 (1991).

Young et al., Yeast RNA Polymerase II Genes: Isolation with Antibody Probes, 222 Science 778-782 (1983).

Boguslaski et al., Clinical Immunochemistry: Principles of Methods and Applications, (1984).

Thompson, et al; "Forensic Validation Study of Antibody Profiling Identification", Idaho National Engineering and Environmental Laboratory, FRENZY—Forensic Science and Crime Scene Technology, Conference and Expo, Washington, D.C., May 14-17 2001, 24 pg.

Thompson, et al; "Novel Assay for Drug and Identity Determination of Body Fluids", Idaho National Engineering and Environmental Laboratory, American Academy of Forensic Sciences Annual Meeting, Reno, Feb. 22-26, 2000, 2 pgs.

Unlu et al., "Difference gel electrophoresis: A single gel method for detecting changes in protein extracts," Electrophoresis, vol. 18; 1997; pp. 2071-2077.

Agg et al., "Preliminary Investigations into Tris (2,2'-bipyridyl) Ruthenium (III) as a Chemiluminescent Reagent for the Detection of 3,6-Diacetylmorphine (Heroin) on Surfaces," Journal of Forensic Science, Sep. 2007, vol. 52, No. 5, p. 1111-1114.

Ascher et al., "Determination of the Etiology of Seroreversals in HIV Testing by Antibody Fingerprinting", Journal of Acquired Immune Deficiency Syndromes, 6:241-244 (1993) Raven Press, Ltd, NY.

Baird, Jeffrey, Forensic DNA in the Trial Court 1990-1992: A Brief History, pp. 61-75.

Bernard et al., "Micromosaic Immunoassays," Analytical Chemistry vol. 73, 2001, pp. 8-12.

BioDiscovery, Inc.; "ImaGene User Manual", Version 7, 1996-2006, 8 pgs.

Bowers, Larry D., "Athletic Drug Testing", Sport Pharmacology, 1998, p. 299-319.

Cambridge Healthtech Institute's Fourth Annual, DNA Forensics (Brochure), 2000, 6 pgs.

Caterino-De-Araujo et al., "Sensitivity of Two Enzyme-linked Immunosorbent Assay Tests in Relation to Western Blot in Detecting Human T-Cell Lymphotropic Virus Types I and II Infection among HIV-1 Infected Patients from Sao Paulo, Brazil," Diagnostic Microbiol Infect Dis; 1998; 30; 173-182; 10 pgs.

Cone, Edward; "Salvia Testing for Drugs of Abuse", Annals New York Academy of Sciences, 1995, p. 91-127.

Controversy Over Forensic DNA Analysis, Science in the Courtroom, QC Researcher, pp. 924-925, Oct. 22, 1993.

Derisi et al., "Exploring the Metabolic and Genetic Control of Gene Expression on a Genomic Scale," Science, vol. 278; Oct. 24, 1997; pp. 680-686.

Dow et al., "Automatic Multiparameter Fluorescence Imaging for Determining Lymphocyte Phenotype and Activation Status in Melanoma Tissue Sections," Cytometry, vol. 25; 1996, pp. 71-81.

Eisen, M. "ScanAiyze User Manual," 1999, Retrieved from http://rana.lbl.gov/manuals/ScanAiyzeDoc.pdf on Nov. 6, 2009.

International Preliminary Report on Patentability for serial No. PCT/US02/39027, filed Nov. 25, 2002, mailed Mar. 19, 2004, 8 pgs.

International Preliminary Report on Patentability for serial No. PCT/US2008/065339, filed May 30, 2008, mailed Dec. 1, 2009, 6 pgs.

International Preliminary Report on Patentability for serial No. PCT/US2008/054011, filed Feb. 14, 2008, mailed Sep. 29, 2009, 8 pgs.

(56) References Cited

OTHER PUBLICATIONS

International Preliminary Report on Patentability for serial No. PCT/US2008/065321, filed May 30, 2008, mailed Dec. 1, 2009, 8 pgs.
International Search Report and Written Opinion for serial No. PCT/US08/65339, filed May 30, 2008, mailed Jan. 28, 2009, 5 pgs.
International Search Report and Written Opinion for serial No. PCT/US2008/065321, filed May 30, 2008, mailed Jan. 16, 2009, 7 pgs.
International Search Report and Written Opinion for serial No. PCT/US08/54011, filed Feb. 14, 2008, mailed Oct. 21, 2008, 8 pgs.
International Search Report and Written Opinion for serial No. PCT/US02/039027, filed Nov. 25, 2002, mailed Mar. 13, 2013, 6 pgs.
Karch. S. B., Drug Abuse Handbook, CRC Press, 1998, p. 727-798.
Kidwell, et al; "Testing for drugs of abuse in saliva and sweat", Jounral of Chromatography B, vol. 173, 1998, p. 111-135.
McCabe, John; "DNA Fingerprinting: The Failings of Frye", Westlaw, 16 N. III. U. L. Rev. 455, pp. 455-481.
Miragen, "Antibody Profile Assay", Advertisement, 1996, 1 pg.
Parry, Tests for HIV and hepatitis viruses, 694 Annals N.Y Acad. Sci. 221, 1993, 18 pgs.
Peat et al., "Analytical Considerations and Approaches for Drugs", Drug Abuse Handbook, 1998, p. 751-764.
Sanchez-Carbayo, Marta: "Antibody arrays: Technical considerations and clinical applications in cancer," Clinical Chemistry, vol. 52, No. 9, Sep. 2006, pp. 1651-1659.
Schramm et al.. "Drugs of Abuse in Saliva: A Review", 16 J. Anal. Toxicology, 1992, p. 1-9.
Supplementary European Search Report from EP 08 72 9906 dated Mar. 25, 2010; 5 pages.
Thompson et al., "A Novel Test for Detection of Drugs in the Body That Also Provides the Identity of the Person Being Examined," ONDCP International Technology Symposium Jun. 25-28, 2001, 10 pgs.
Thompson et al., "Antibody Profiling Technique for Rapid Identification of Forensic Samples," CAT/NWAFS/SWAFS/SAT Combined Professional Training Seminar, Las Vegas, Nov. 3-7, 1997, 19 pgs.
Supplementary European Search Report for serial No. EP08780412, filed Feb. 12, 2008, mailed Nov. 8, 2010; 13 pgs.
Shin Masashi et al; "Multilayer peroxidase-labeled antibody method: Comparison with labeled streptavidin-biotin method, avidin-biotin-peroxidase complex method, and peroxidase-antiperoxidase method" Journal of Clinical Laboratory Analysis, vol. 9, No. 6, 1995, pp. 424-430, XP002608579.
Morgan A C Jr et al: Monoclonal antibodies to human melanoma-associated antigens: an amplified enzyme-linked immunosorbent assay for the detection of antigen, antibody, and immune complexes Cancer Research, American Association for Cancer Rerearch, US, vol. 43, No. 7, Jul. 1, 1983, pp. 3155-3159, XP009140641.
Linsenmayer T F et al: "Multiple Reaction 11-5 Cycling a Method for Enhancement of the Immunochemical Signal of Monoclonal Antibodies"Journal of Histochemistry and Cytochemistry, vol. 36, No. 8, 1988, pp. 1075-1078.
McQuaid et al: "Detection protocols for 11-5 biotinylated probes: optimization using multistep techniques." The Journal of Histochemistry and Cytochemistry : Official Journal of the Histochemistry Society Apr. 1992 LNKD• Pubmed:1552190, vol. 40, No. 4, Apr. 1992, pp. 569-574, XP002608581.
Butler; The amplified ELISA: principles of and applications for the comparative quantitation of class and subclass antibodies and the distribution of antibodies and antigens in biochemical separates. Methods in Enzymology; [Methods in Enzymology], Academic Press Inc, San Diego, CA US Lnkd—DOI:10:1016/0076-6879(81) 73087-8, vol, 73, No. Part B, Jan. 1, 1981 pp. 482-523, XP009140635.
Canadian Office Action for serial No. 2,679,573, filed Feb. 14, 2008, mailed Aug. 23, 2012, 4 pgs.
Aurell, et al; "Rapid Detection and Enumeration of *Legionella pneumophila* in Hot Water Systems by Solid-Phase Cytometry," Applied and Environmental Microbiology, Mar. 2004, p. 1651-1657.

Tuson, et al.; "A novel immunohistochemical technique for demonstration of specific binding of human monoclonal antibodies to human cryostat tissue sections". The Journal of Histochemistry and Cytochemistry, vol. 38, No. 7, 1990, p. 923-926.
Brown, et al; "Primary antibody-Fab fragment complexes: a flexible alternative to traditional direct and indirect immunolabeling techniques", Journal of Histochemistry and Cytochemistry, vol. 52(9): 2004, p. 1219-1230.
Habb, et al; "Protein microarrays for highly parallel detection and quantitation of specific proteins and antibodies in complex solutions." Genome Biology 2001, 2(2):research0004.1-0004.13, 13 pgs.
International Search Report and Written Opinion for serial No. PCT/US08/53641, filed Feb. 12, 2008, mailed Sep. 8, 2008, 8 pgs.
Thompson, Vicki; U.S. Patent Application entitled: Rapid Classificaiton of Biological Components, having U.S. Appl. No. 11/101,216, filed Apr. 6, 2005, 48 pgs.
Apel, William A.; Non-Final Office Action for U.S. Appl. No. 13/771,915, filed Feb. 20, 2013, mailed Sep. 11, 2013, 11 pgs.
Thompson, Vicki; Non-Final Office Action for U.S. Appl. No. 11/101,216, filed 416/2005, mailed May 8, 2007, 21 pgs.
Thompson, Vicki; Final Office Action for U.S. Appl. No. 11/101,216, filed Apr. 6, 2005, mailed Oct. 19, 2007, 13 pgs.
Thompson, Vicki; Non-Final Office Action for U.S. Appl. No. 11/101,216, filed Apr. 6, 2005, mailed Mar. 13, 2008, 13 pgs.
Thompson, Vicki; Final Office Action for U.S. Appl. No. 11/101,216, filed Apr. 6, 2005, mailed Sep. 30, 2008, 15 pgs.
Thompson, Vicki; Non-Final Office Action for U.S. Appl. No. 11/101,216, filed Apr. 6, 2005, mailed Feb. 25, 2009, 17 pgs.
Thompson, Vicki; Notice of Allowance for U.S. Appl. No. 11/101,216, filed Apr. 6, 2005, mailed Sep. 22, 2009, 11 pgs.
Thompson, Vicki; Issue Notification for U.S. Appl. No. 11/101,216, filed Apr. 6, 2005, mailed Mar. 3, 2010, 1 pg.
Apel, William; U.S. Patent Application entitled: Antibody Profiling Sensitivity Through Increased Reporter Antibody Layering, having U.S. Appl. No. 11/691,096, filed Mar. 26, 2007, 46 pgs.
Apel, William; Restriction Requirement for U.S. Appl. No. 11/691,096, filed Mar. 26, 2007, mailed Aug. 20, 2008, 9 pgs.
Apel, William; Non-Final Office Action for U.S. Appl. No. 11/691,096, filed Mar. 26, 2007, mailed Dec. 29, 2008, 30 pgs.
Apel, William; Notice of Allowance for or U.S. Appl. No. 11/691,096, filed Mar. 26, 2007, mailed Jul. 15, 2009, 6 pgs.
Apel, William; Examiner Interview Summary Record for U.S. Appl. No. 11/691,096, filed Mar. 26, 2007, mailed Aug. 25, 2009, 2 pgs.
Apel, William; Issue Notification for or U.S. Appl. No. 11/691,096, filed Mar. 26, 2007, mailed Dec. 23, 2009, 1 pgs.
Apel, William; Notice of Allowance for or U.S. Appl. No. 11/691,096, filed Mar. 26, 2007, mailed Jan. 28, 2010, 10 pgs.
Apel, William; Issue Notification for or U.S. Appl. No. 11/691,096, filed Mar. 26, 2007, mailed Mar. 24, 2010, 1 pgs.
Apel, William; U.S. Patent Re-issue Application entitled: Antibody Profiling Sensitivity Through Increased Reporter Antibody Layering, having U.S. Appl. No. 13/439,400, filed Apr. 4, 2012, 22 pgs.
Apel, William; Notice of Allowance for U.S. Appl. No. 13/439,400, filed Apr. 4, 2012, mailed Oct. 17, 2012, 18 pgs.
Apel, William; Issue Notification for U.S. Appl. No. 13/439,400, filed Apr. 4, 2012, mailed Feb. 6, 2013, 1 pg.
Apel, William; U.S. Patent Continuation Re-Issue Application entitled: Improved Antibody Profiling Sensitivity Through Increased Reporter Antibody Layering, having U.S. Appl. No. 13/771,915, filed Feb. 20, 2013, 24 pgs.
Lacey, Jeffrey A.; U.S. Provisional Patent Application entitled: Computing Systems, Computer-Readable Media and Methods of Antibody Profiling, U.S. Appl. No. 61/786,961, filed Mar. 15, 2013, 60 pgs.
Apel, William A.; U.S. Patent Application entitled: Antibody Profiling, Methods and Apparatus for Identifying an Individual or Source of a Biological Material, U.S. Appl. No. 13/832,406, filed Mar. 15, 2013; 53 pgs.
Apel, William; U.S. Patent Application entitled: Identification of Discriminant Proteins Through Antibody Profiling, Methods, and Apparatus for Identifying an Individual, having U.S. Appl. No. 12/883,002, filed Sep. 15, 2010, 43 pgs.

(56) References Cited

OTHER PUBLICATIONS

Thompson, Vicki; U.S. Patent Application entitled: Rapid Classification of Biological Components, having U.S. Appl. No. 10/017,577, filed Dec. 14, 2001, 58 pgs.
Thompson, Vicki; Restriction Requirement for U.S. Appl. No. 10/017,577, filed Dec. 14, 2001, mailed Jun. 29, 2004, 7 pgs.
Thompson, Vicki; Restriction Requirement for U.S. Appl. No. 10/017,577, filed Dec. 14, 2001, mailed Oct. 20, 2004, 8 pgs.
Thompson, Vicki; Notice of Allowance for U.S. Appl. No. 10/017,577, filed Dec. 14, 2001, mailed Jan. 25, 2005, 13 pgs.
Thompson, Vicki; U.S. Patent Re-issue Application entitled: Rapid Classification of Biological Components, having U.S. Appl. No. 13/425,181, filed Mar. 20, 2012, 24 pgs.
Thompson, Vicki; Non-Final Office Action for U.S. Appl. No. 13/425,181, filed Mar. 20, 2012, mailed Sep. 5, 2012, 28 pgs.
Thompson, Vicki; U.S. Patent Application entitled: Rapid Classification of Biological Components, having U.S. Appl. No. 11/101,254, filed Apr. 6, 2005, 48 pgs.
Thompson, Vicki; Non-Final Office Action for U.S. Appl. No. 11/101,254, filed Apr. 6, 2005, mailed May 2, 2007, 19 pgs.
Thompson, Vicki; Non-Final Office Action for U.S. Appl. No. 11/101,254, filed Apr. 6, 2005, mailed Oct. 4, 2007, 12 pgs.
Thompson, Vicki; Non-Final Office Action for U.S. Appl. No. 11/101,254, filed Apr. 6, 2005, mailed Mar. 17, 2008, 15 pgs.
Thompson, Vicki; Final Office Action for U.S. Appl. No. 11/101,254, filed Apr. 6, 2005, mailed Sep. 5, 2008, 15 pgs.
Thompson, Vicki; Advisory Action for U.S. Appl. No. 11/101,254, filed Apr. 6, 2005, mailed Dec. 2, 2008, 17 pgs.
Thompson, Vicki; Non-Final Office Action for U.S. Appl. No. 11/101,254, filed Apr. 6, 2005, mailed Dec. 17, 2008, 17 pgs.
Thompson, Vicki; Notice of Allowance for U.S. Appl. No. 11/101,254, filed Apr. 6, 2005, mailed Aug. 10, 2009, 7 pgs.
Thompson, Vicki; Issue Notification for U.S. Appl. No. 11/101,254, filed Apr. 6, 2005, mailed Mar. 23, 2010, 1 pg.
Apel, William A.; U.S. Patent Application entitled: Compositions and Methods for Combining Report Antibodies, having U.S. Appl. No. 11/748,361, filed May 14, 2007, 57 pgs.
Apel, William; Non-Final Office Action for U.S. Appl. No. 11/748,361, filed May 14, 2007, mailed Oct. 2, 2009, 13 pgs.
Apel, William; Final Office Action for U.S. Appl. No. 11/748,361, filed May 14, 2007, mailed Mar. 18, 2010, 16 pgs.
Apel, William; Non-Final Office Action for U.S. Appl. No. 11/748,361, filed May 14, 2007, mailed Jun. 10, 2010, 10 pgs.
Apel, William; Final Office Action for U.S. Appl. No. 11/748,361, filed May 14, 2007, mailed Nov. 24, 2010, 13 pgs.
Canada Office Action for serial No. 2,685,997, filed Feb. 12, 2008, mailed Mar. 14, 2012, 2 pgs.
Hellstrom, et al; "Epitope mapping and use of anti-idiotypic antibodies to the L6 monoclonal anticarcinoma antibody", Cancer Research 50, 1990, p. 2449-2454.
Thompson, Vicki; Advisory Action for U.S. Appl. No. 11/101,216, filed Apr. 6, 2005, mailed Dec. 31, 2008, 17 pgs.
Apel, William A.; Restriction Requirement for U.S. Appl. No. 12/883,002, mailed Apr. 30, 2013, 10 pgs.

Extended European Search Report for serial No. 10819278.2, filed Mar. 28, 2012, mailed Jun. 28, 2013, 10 pgs.
Gaseitsiwe et al; "Pattern Recognition in Pulmonary Tuberculosis Defined by High Content Peptide Microarray Chip Analysis Representing 61 Proteins from *M. tuberculosis*", PLOS ONE, Public Library of Science, vol. 3, No. 12, Dec. 1, 2008, pp. e3840-1, XP07159747, ISSN:1932-6203.
Canadian Office Action for serial No. 2,679,573, filed Feb. 14, 2008, mailed Jul. 11, 2013, 5 pgs.
Apel, William; Non-Final Office Action for U.S. Appl. No. 12/883,002, filed Sep. 15, 2010, mailed Jul. 29, 2013, 17 pgs.
Apel, William A.; Non-Final Office Action for U.S. Appl. No. 11/748,361, filed May 14, 2007, mailed Oct. 3, 2013, 63 pgs.
Harlow, et al. 1988. Antibodies, A Laboratory Manual, Cold Spring Harbor Laboratory, Cold Spring Harbor. pp. 319, 321, and 344.
Mokry, 1996. Versatility of immunochemical reactions: comprehensive survey of detections sytems. Acta Medica 39: 129-140.
Apel, William A.; Final Office Action for U.S. Appl. No. 12/883,002, filed Sep. 15, 2010, mailed Feb. 10, 2014, 40 pgs.
Apel, William A.; Final Office Action for U.S. Appl. No. 13/771,915, filed Feb. 20, 2013, mailed Mar. 19, 2014, 33 pgs.
Apel, William A.; Non-Final Office Action for U.S. Appl. No. 13/832,406, filed Mar. 15, 2013, mailed Jul. 25, 2014, 75 pgs.
Apel, William A.; Restriction Requirement for U.S. Appl. No. 13/832,406, filed Mar. 15, 2013, mailed Feb. 26, 2014; 7 pgs.
Guo, et al.; Functional Protein Microarrays in Drug Discovery 8 (2007) : 53.
Lacey, Jeffrey A.; U.S. Patent Application Entitled: Computing Systems, Computer-Readable Media and Methods of Antibody Profiling, U.S. Appl. No. 14/209,720, filed Mar. 13, 2014; 60 pgs.
Apel, William A.; Notice of Allowance for U.S. Appl. No. 12/883,002, filed Sep. 15, 2010, mailed Apr. 18, 2014, 7 pgs.
Canadian Office Action for serial No. 2,679,573, filed Feb. 14, 2008, mailed May 16, 2014, 5 pgs.
Apel, William A.; European Office Action for serial No. 08780412.6, filed Feb. 12, 2008, mailed Apr. 4, 2014, 6 pgs.
Apel, William; PCT Application entitled: Antibody Profiling, Methods and Apparatus for Identifying an Individual or Source of a Biological Material, having serial No. PCT/US2014/024779, filed Mar. 12, 2014, 49 pgs.
Lacey, Jeffrey A.; International Search Report and Written Opinion for PCT/US2014/025561, filed Mar. 13, 2014, mailed Aug. 7, 2014, 9 pgs.
Lacey, Jeffrey; PCT Application entitled: Computing Systems, Computer-Readable Media and Methods of Antibody Profiling, having serial No. PCT/US14/25561, filed Mar. 13, 2014, 57 pgs.
Thompson, Vicki; European Office Action for serial No. 10819278.2, filed Sep. 17, 2010, mailed Feb. 17, 2014, 5 pgs.
Apel, William; International Search Report and Written Opinion for serial No. PCT/US2014/024779, filed Mar. 12, 2014, mailed Sep. 8, 2014, 27 pgs.
Espina, et al.; Protein microarrays: molecular profiling technologies for clinical specimens. Proteomics Nov. 2003, vol. 3 No. 11, pp. 2091-2100.
William A.; Notice of Allowance for U.S. Appl. No. 13/771,915, filed Feb. 20, 2013, mailed Oct. 31, 2014, 9 pgs.

\* cited by examiner

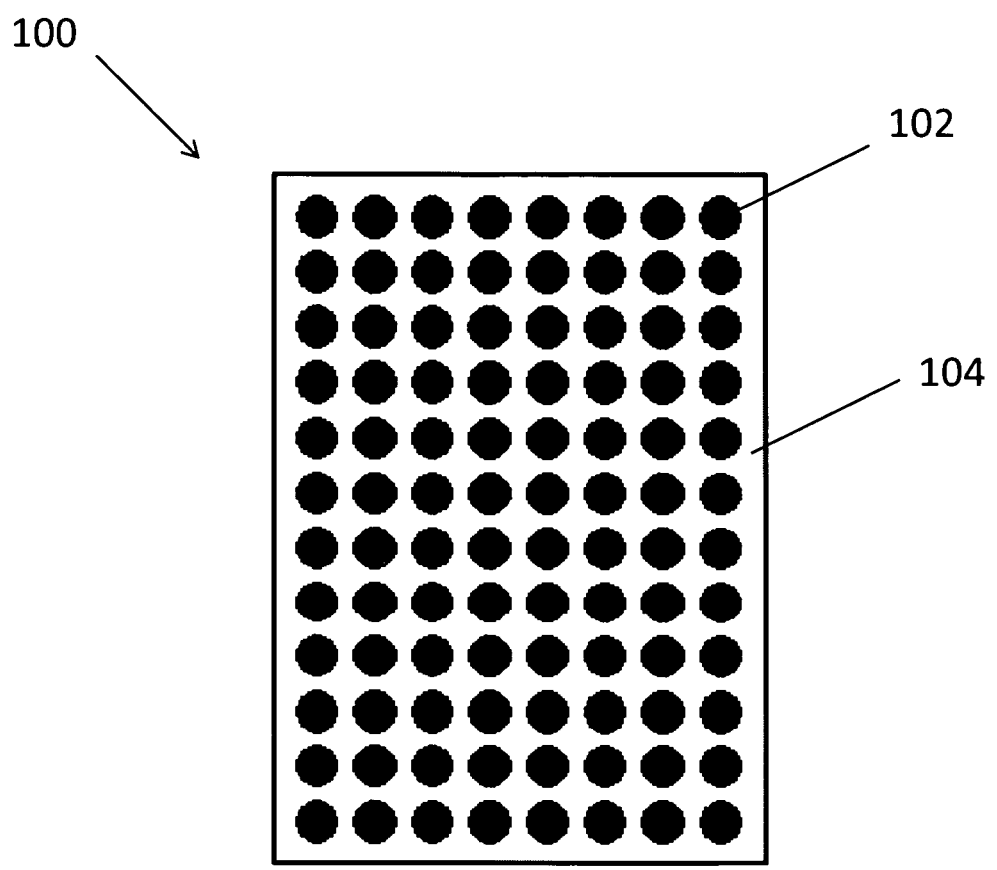

IDENTIFICATION OF DISCRIMINANT PROTEINS THROUGH ANTIBODY PROFILING, METHODS AND APPARATUS FOR IDENTIFYING AN INDIVIDUAL

GOVERNMENT RIGHTS

This invention was made with government support under Contract Number DE-AC07-05ID14517 awarded by the United States Department of Energy. The government has certain rights in the invention.

TECHNICAL FIELD

Embodiments of the present invention relate to analyzing biological samples to identify proteins useful in identifying individuals, and more particularly, to methods and apparatus for identifying an individual using such proteins.

BACKGROUND

The importance of differentiating and identifying individuals based on biological samples with a high degree of efficiency and accuracy is presented in various contexts. For example, the need for accurate means of identification is of increasing importance in law enforcement as it may be critical to link an individual to a forensic sample, such as blood, tissue, hair, saliva, or the like.

Many methods are known for identifying individuals or biological samples obtained from such individuals. For example, blood typing is based on the existence of antigens on the surface of red blood cells. The ABO system relates to four different conditions with respect to two antigens, A and B. Type A individuals exhibit the A antigen; Type B individuals exhibit the B antigen; Type AB individuals exhibit both the A and B antigens; and Type O individuals exhibit neither the A nor the B antigen. By analyzing a sample of a person's blood, it is possible to classify the blood as belonging to one of these blood groups. While this method may be used to identify one individual out of a small group of individuals, the method is limited when the group of individuals is larger because no distinction is made between persons of the same blood group. For example, the distribution of the ABO blood groups in the U.S. is approximately 45% O, 42% A, 10% B, and 3% AB. Tests based on other blood group antigens or isozymes present in body fluids suffer from the same disadvantages as the ABO blood typing tests. These methods may exclude certain individuals, but cannot differentiate between members of the same blood group.

A variety of immunological and biochemical tests based on genetics are routinely used in paternity testing, as well as for determining the compatibility of donors and recipients involved in transplant or transfusion procedures, and also sometimes as an aid in the identification of humans and animals. For example, serological testing of proteins encoded by the human leukocyte antigen (HLA) gene locus is well known. Although a good deal of information is known concerning the genetic makeup of the HLA locus, there are many drawbacks to using HLA serological typing for identifying individuals in a large group. Each of the HLA antigens must be tested for in a separate assay, and many such antigens must be assayed to identify an individual, an arduous process when identifying one individual in a large group.

In the past decade, DNA-based analysis methods, such as restriction fragment length polymorphisms (RFLPs) and polymerase chain reaction (PCR) have rapidly gained acceptance in forensic and paternity analyses for matching biological samples to an individual. RFLP techniques are problematic, however, due to the need for relatively large sample sizes, specialized equipment, highly skilled technicians, and lengthy analysis times. For forensic applications there is often not enough sample available for this type of assay, and in remote areas the necessary equipment is often not available. In addition, the cost and length of time required to performed this technique may hinder a criminal investigation. Moreover, the cost of RFLP analysis may be prohibitory if screening of many samples is necessary. PCR techniques have the advantages over RFLP analysis of requiring much smaller sample sizes and permitting more rapid analysis, but they still require specialized equipment and skilled technicians, and they are also expensive.

Antibody profiling is an identification technique that has many advantages over conventional DNA-based analysis methods. For example, antibody profiling methods provide increased speed and ease of use and decreased costs in comparison to conventional DNA based analysis. Current antibody profiling methods for identifying individuals utilize an undefined mixture of proteins.

U.S. Pat. No. 4,880,750 and U.S. Pat. No. 5,270,167 each disclose antibody profiling as a method that purportedly overcomes many of the disadvantages associated with DNA analysis. The antibody profiling method is based on the discovery that every individual has a unique set of antibodies present in his or her bodily fluids. R. M. Bernstein et al., *Cellular Protein and RNA Antigens in Autoimmune Disease*, 2 Mol. Biol. Med. 105-120 (1984). Such antibodies, termed "individual-specific antibodies" or "ISAs," were found in blood, serum, saliva, urine, semen, perspiration, tears, and body tissues. A. M. Francoeur, *Antibody Fingerprinting: A Novel Method for Identifying Individual People and Animals*, 6 Bio/technology 821-825 (1988). The ISAs are not associated with disease and are thought to be directed against cellular components of the body. Individuals are born with an antibody profile that matches the mother's antibody profile. T. F. Unger & A. Strauss, *Individual-specific Antibody Profiles as a Means of Newborn Infant Identification*, 15 J. Perinatology 152-155 (1995). An individual's antibody profile gradually changes, however, until a stable unique pattern is obtained by about two years of age. It has been shown that even genetically identical individuals have different antibody profiles. An individual's profile is apparently stable for life and is not affected by short-term illnesses. A. M. Francoeur, supra. Few studies have been conducted on individuals with long-term diseases. Preliminary results, however, indicate that, although a few extra bands may appear, the overall pattern remains intact. This technique has been used in the medical field to track patient samples and avoid sample mix-ups. In addition, the technique has been used in hospitals in cases where switching of infants or abduction has been alleged.

WO 97/29206 discloses a method for identifying the source of a biological sample used for diagnostic testing by linking diagnostic test results to an antibody profile of the biological sample. By generating an antibody profile of each biological sample, the origin of the biological sample is identified.

Assays are also available that use specific nucleic acid probes or other biological molecules attached to surfaces such as glass, silicon, polymethacrylate, polymeric filters, microspheres, resins, and the like. In a configuration where the surface is planar, these assays are sometimes referred to as "biochips." Initially, biochips contained nucleic acid probes attached to glass or silicon substrates in microarrays. These DNA or RNA chips are made by microfabrication technologies initially developed for use in computer chip manufacturing. Leading DNA chip technologies include an in situ photochemical synthesis approach, P. S. Fodor, 277 Science 393-395 (1997); U.S. Pat. No. 5,445,934; an electrochemical positioning approach, U.S. Pat. No. 5,605,662; depositing gene probes on the chip using a sprayer that resembles an ink-jet printer; and the use of gels in a solution-based process. Arrays of other types of molecules, such as peptides, have been fabricated on biochips, e.g., U.S. Pat. No. 5,445,934.

BRIEF SUMMARY OF THE INVENTION

In some embodiments, the present invention includes a method of determining discriminant proteins useful for identifying an individual. For example, the method may be used to determine a set that includes one or more of such discriminant proteins. A plurality of samples may be obtained from a different individual and may include individual specific antibodies. Each of the plurality of samples may be contacted with an array including a plurality of antigens to form at least one immune complex, the immune complex including an individual specific antibody from the sample bound to an antigen of the array. Each antigen of the array is known and is immobilized at a known predetermined location in the array. At least one detection agent may be applied to the array and may include at least one interacting protein conjugated to a marker to detect the immune complexes. The immune complexes on the array may be detected to obtain an antibody profile corresponding to each of the different individuals and the antibody profiles corresponding to the different individuals may be compared using, for example, discriminant analysis, to determine at least one target antigen as a discriminant protein useful for indentifying an individual from at least one other individual or population of individuals.

In additional embodiments, the present invention includes a method for identifying source of a biological material. Less than about 200 antigens may be immobilized on a support to form an array. A sample of a biological material including individual-specific antibodies may be obtained and contacted with the array to bind at least a portion of the individual-specific antibodies to the multiple antigens of the array forming immune complexes. A blocking step may be performed prior to applying the sample to prevent binding of antigens, antibodies, and the like to the support wherein such antigens, antibodies, or other molecules are not intended to bind. The support may then be washed to remove any unbound antigens. A detection system such as those disclosed in U.S. Patent Application Nos. 2007/0190585 and 2008/0298667, each of which is incorporated herein by reference, may be used to detect the immune complexes. For example, at least one detection agent including at least one interacting protein conjugated to a marker may be applied to the array to detect the immune complexes. The support may then be washed to remove non-immobilized individual-specific antibodies and detection agent. The immune complexes on the array may be detected to obtain an antibody profile and the antibody profile may be compared to a known antibody profile obtained from an individual. For example, the antibody profile may be correlated to a single individual in a population of from about 1 million individuals to about 100 billion individuals.

In yet further embodiments, the present invention includes a method of designing a protein array useful in identifying an individual. A plurality of samples may be introduced to an array comprising a plurality of antigens, wherein each of the antigens is known and wherein each of the antigens is immobilized at a known predetermined location on a support. Each of the antigens may be known and may be immobilized at a known predetermined location on a support. At least one detection agent including at least one interacting protein conjugated to a marker may be applied to the array to detect immune complexes formed between individual-specific antibodies and antigens of the plurality. The immune complexes formed on the array may be detected to obtain an antibody profile for each of the plurality of samples. The antibody profiles may be analyzed to determine a set of antigens useful in distinguishing an individual among a population.

In still further embodiments, the present invention includes a method of determining a relationship between a plurality of individuals. An array including less than about 200 antigens on a support may be formed. Each of the antigens is determined to distinguish between individuals. A sample of a biological material having individual-specific antibodies may be obtained from each of a plurality of individuals. The array may be contacted with the sample to bind at least a portion of the individual-specific antibodies therein to the multiple antigens of the array, at least one immune complex. At least one detection agent including at least one interacting protein conjugated to a marker may be applied to the array to detect the immune complexes. The support may be washed to remove non-immobilized individual-specific antibodies and detection agent and the immune complexes on the array detected to obtain an antibody profile.

BRIEF DESCRIPTION OF THE DRAWINGS

While the specification concludes with claims particularly pointing out and distinctly claiming that which is regarded as the present invention, advantages of this invention may be more readily ascertained from the following description of the invention when read in conjunction with the accompanying drawings in which:

FIG. 1 is an illustration of a protein array according to an embodiment of the invention.

DETAILED DESCRIPTION OF THE INVENTION

Before embodiments of the present invention are described in detail, it is to be understood that this invention is not limited to the particular configurations, process acts, and materials disclosed herein as such configurations, process acts, and materials may vary somewhat. It is also to be understood that the terminology employed herein is used for the purpose of describing particular embodiments only and is not limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that such documents constitute prior art, or that the inventors are not entitled to antedate such disclosure by virtue of prior invention.

While the known methods for using antibody profiling are generally suitable for their limited purposes, they possess certain inherent deficiencies that detract from their overall utility in analyzing, characterizing, and identifying biological samples. For example, the known methods rely on fractionation of antigens by electrophoresis and then transfer of the fractionated antigens to a membrane. Due to differences in conditions from one fractionation procedure to another, there are lot-to-lot differences in the positions of the antigens on the membrane such that results obtained using membranes from one lot cannot be compared with results obtained using membranes from another lot. Further, when colorimetric procedures are used for detecting immune complexes on the membrane, color determination may be subjective such that results may be interpreted differently by different observers.

It would be advantageous to provide a method identifying proteins capable of distinguishing an individual and methods for efficiently and accurately determining identity, distinguishing between individuals, as well as determining the source of biological fluids, especially those amenable to automation.

It must be noted that, as used in this specification and the appended claims, the singular forms "a," "an," and "the" include plural referents unless the context clearly dictates otherwise. Thus, for example, reference to a method for analyzing a biological sample from "an animal" includes reference to two or more of such animals, reference to "a support" includes reference to one or more of such supports, and reference to "an array" includes reference to two or more of such arrays.

As used herein, "blood" means and includes whole blood, plasma, serum, or any derivative of blood. A blood sample may be, for example, serum.

As used herein, "comprising," "including," "containing," "characterized by," and grammatical equivalents thereof are inclusive or open-ended terms that do not exclude additional, unrecited elements or method acts. "Comprising" is to be interpreted as including the more restrictive terms "consisting of" and "consisting essentially of."

As used herein, "consisting of" and grammatical equivalents thereof exclude any element, step, or ingredient not specified in the claim.

As used herein, "consisting essentially of" and grammatical equivalents thereof limit the scope of a claim to the specified materials or acts and those that do not materially affect the basic and novel characteristic or characteristics of the claimed invention.

As used herein, the terms "biological sample" and "sample" mean and include a sample comprising individual-specific antibodies obtained from an organism or from components (e.g., cells) of an organism. The sample may be of any biological material. Such samples include, but are not limited to, blood, blood fractions (e.g. serum, plasma), blood cells (e.g., white cells), tissue or fine needle biopsy samples, urine, saliva, perspiration or semen. Biological samples may also include sections of tissues such as frozen sections taken for histological purposes.

As used herein, "colorigenic" refers to a substrate that produces a colored product upon digestion with an appropriate enzyme. Such colored products include fluorescent and luminescent products.

The term "discriminant analysis" means and includes a set of statistical methods used to select features that optimally discriminate between two or more groups. Application of discriminant analysis to a data set allows the user to focus on the most discriminating features for further analysis.

As used herein, the terms "immobilized" or "affixed" mean and include an association between a protein or antigen and a substrate at the molecular level (i.e., through a covalent or non-covalent bond or interaction). For example, a protein may be immobilized to a support by covalent bonding directly to a surface of the support which may or may not be modified to enhance such covalent bonding. Also, the protein may be immobilized to the support by use of a linker molecule between the protein and the support. Proteins may further be immobilized on the support by steric hindrance within a polymerized gel or by covalent bonding within a polymerized gel. Proteins may also be immobilized on a support through hybridization between the protein and a molecule immobilized on the support.

The term "protein array" as used herein refers to a protein array, a protein macroarray, a protein microarray or a protein nanoarray. A protein array may include, for example, but is not limited to, ProtoArray™ high density protein array, which is commercially available from Invitrogen (Carlsbad, Calif.). The ProtoArray™ high density protein array may be used to screen complex biological mixtures, such as serum, to assay for the presence of autoantibodies directed against human proteins. Alternatively, a custom protein array that includes autoantigens, such as those provided herein, for the detection of autoantibody biomarkers, may be used to assay for the presence of autoantibodies directed against human proteins. In certain disease states including autoimmune diseases and cancer, autoantibodies are expressed at altered levels relative to those observed in healthy individuals.

As used herein, "support" means a generally or substantially planar substrate onto which an array of antigens is disposed. A support may comprise any material or combination of materials suitable for carrying the array. Materials used to construct these supports need to meet several requirements, such as (1) the presence of surface groups that may be easily derivatized, (2) inertness to reagents used in the assay, (3) stability over time, and (4) compatibility with biological samples. For example, suitable materials include glass, silicon, silicon dioxide (i.e., silica), plastics, polymers, hydrophilic inorganic supports, and ceramic materials. Illustrative plastics and polymers include poly(tetrafluoroethylene), poly (vinylidenedifluoride), polystyrene, polycarbonate, polymethacrylate, and combinations thereof. Illustrative hydrophilic inorganic supports include alumina, zirconia, titania, and nickel oxide. An example of a glass substrate would be a microscope slide. Silicon wafers used to make computer chips have also been used to make biochips. See, for example, U.S. Pat. No. 5,605,662. The supports may further include a coating, such as, nitrocellulose, gelatin, a polymer (i.e., polyvinyl difluoride) or an aldehyde.

In some embodiments, a method of determining proteins useful in discriminating one individual from 1 or more other individuals and/or positively identifying an individual is provided. Such proteins may be referred to herein as "discriminant proteins." The method may employ a protein array including a plurality of proteins immobilized on a support. As a non-limiting example, the protein array may be a ProtoArray™ human protein microarray, which is commercially available from Invitrogen Corporation (Carlsbad. Calif.). The plurality of proteins immobilized on the support may include a plurality of antigens.

In a typical assay, a plurality of biological samples including individual-specific antibodies may each be physically contacted with a protein array, under conditions that permit high affinity binding, but that minimize non-specific interactions. In one embodiment, the biological samples are introduced to the protein array that includes a plurality of antigens immobilized in predetermined locations on a support. The protein array may be washed free of unbound material, and the presence of bound antibodies may be detected, and correlated with the cognate antigen.

The data collected from each of the plurality of biological samples profiled on a protein array may be used to determine an antibody profile for the individual. The antibody profiles may be analyzed using, for example, conventional discriminant analysis methods, to determine proteins relevant in discriminating and positively identifying an individual (i.e., discriminant proteins) from a population of one or more other individuals. The discriminant proteins may be used to generate a test panel for identifying an individual or determining a source of a biological sample. In some embodiments, the test panel may be, for example, a protein array 100, as shown in FIG. 1, including a plurality of the discriminant proteins arranged as spots 102 in predetermined locations on a support 104.

Protein Array

The protein array may be prepared by attaching the antigens to the surface of the support in a preselected pattern such that the locations of antigens in the array are known. As used herein, an antigen is a substance that is bound by an antibody. Antigens may include proteins, carbohydrates, nucleic acids, hormones, drugs, receptors, tumor markers, and the like, and mixtures thereof. An antigen may also be a group of antigens, such as a particular fraction of proteins eluted from a size exclusion chromatography column. Still further, an antigen may also be identified as a designated clone from an expression library or a random epitope library.

In one embodiment, antigens may be isolated from HeLa cells as generally described in A. M. Francoeur et al., *Identification of Ki (Ku, p70/p80) Autoantigens and Analysis of Anti-Ki Autoantibody Reactivity*, 136 J. Immunol. 1648 (1986). Briefly, HeLa cells may be grown in standard medium under standard tissue culture conditions. Confluent HeLa cell cultures may then be rinsed, preferably with phosphate-buffered saline (PBS), lysed with detergent, and centrifuged to remove insoluble cellular debris. The supernate contains approximately 10,000 immunologically distinct antigens suitable for generating an array.

There is no requirement that the antigens used to generate the array be known. All that is required is that the source of the antigens be consistent such that a reproducible array may be generated. For example, the HeLa cell supernate containing the antigens may be fractionated on a size exclusion column, electrophoretic gel, density gradient, or the like, as is well known in the art. Fractions may be collected, and each fraction collected could represent a unique set of antigens for the purpose of generating the array. Thus, even though the antigens may be unknown, a reproducible array may be generated if the HeLa cell antigens may be isolated and fractionated using the same method and conditions.

Other methods, such as preparation of random peptide libraries or epitope libraries are well known in the art and may be used to reproducibly produce antigens (e.g., J. K. Scott and G. P. Smith, *Searching for Peptide Ligands with an Epitope Library*, 249 Science 386 (1990); J. J. Devlin et al., *Random Peptide Libraries: A Source of Specific Protein Binding Molecules*, 249 Science 404-406 (1990); S. E. Cwirla et al., *Peptides on Phage: A Vast Library of Peptides for Identifying Ligands*, 87 Proc. Nat'l Acad. Sci. USA 6378-6382 (1990); K. S. Lam et al., *A New Type of Synthetic Peptide Library for Identifying Ligand-binding Activity*, 354 Nature 82-84 (1991); S. Cabilly, *Combinatorial Peptide Library Protocols*, Humana Press, 304 p.p., 129-154 1997; and U.S. Pat. No. 5,885,780). Such libraries may be constructed by ligating synthetic oligonucleotides into an appropriate fusion phage. Fusion phages may be filamentous bacteriophage vectors in which foreign sequences may be cloned into phage gene III and displayed as part of the gene III protein (pIII) at one tip of the virion. Each phage encodes a single random sequence and expresses it as a fusion complex with pIII, a minor coat protein present at about five molecules per phage. For example, in the fusion phage techniques of J. K. Scott and G. P. Smith, supra, a library was constructed of phage containing a variable cassette of six amino acid residues. The hexapeptide modules fused to bacteriophage proteins provided a library for the screening methodology that may examine $>10^{12}$ phages (or about $10^8$-$10^{10}$ different clones) at one time, each with a test sequence on the virion surface. The library obtained was used to screen monoclonal antibodies specific for particular hexapeptide sequences. The fusion phage system has also been used by other groups, and libraries containing longer peptide inserts have been constructed. Fusion phage prepared according to this methodology may be selected randomly or non-randomly for inclusion in the array of antigens. The fusion phages selected for inclusion in the array may be propagated by standard methods to result in what is virtually an endless supply of the selected antigens.

Other methods for producing antigens are also known in the art. For example, expression libraries may be prepared by random cloning of DNA fragments or cDNA into an expression vector (e.g., R. A. Young and R. W. Davis, *Yeast RNA Polymerase II Genes: Isolation with Antibody Probes*, 222 Science 778-782 (1983); G. M. Santangelo et al., *Cloning of Open Reading Frames and Promoters from the Saccharomyces cerevisiae Genome: Construction of Genomic Libraries of Random Small Fragments*, 46 Gene 181-186 (1986). Expression vectors that could be used for making such libraries are commercially available from a variety of sources. For example, random fragments of HeLa cell DNA or cDNA may be cloned into an expression vector, and then clones expressing HeLa cell proteins may be selected. These clones may then be propagated by methods well known in the art. The expressed proteins may then be isolated or purified and may be used in the making of the array.

Alternatively, antigens may be synthesized using recombinant DNA technology well known in the art. Genes that code for many proteins from a gamut of organisms including viruses, bacteria, and mammals have been cloned, and thus large quantities of highly pure proteins may be synthesized quickly and inexpensively. For example, the genes that code for many eukaryotic and mammalian membrane-bound receptors, growth factors, cell adhesion molecules, and regulatory proteins have been cloned and may be useful as antigens. Many proteins produced by such recombinant techniques, such as transforming growth factor, acidic and basic fibroblast growth factors, interferon, insulin-like growth factor, and various interleukins from different species, are commercially available. In most instances, the entire polypeptide need not be used as an antigen. For example, any size or portion of the polypeptide that contains at least one epitope, i.e., antigenic determinant or portion of an antigen that specifically interacts with an antibody, will suffice for use in the array. In addition, a particular antigen may be purified or isolated from any natural or synthetic source of the antigen by methods known in the art.

The antigens, whether selected randomly or non-randomly, may be disposed on the support to result in the array. The pattern of the antigens on the support should be reproducible. In embodiments, the location and identity of each antigen on the support may be known. For example, in a 10×10 array one skilled in the art might place antigens 1-100 in locations 1-100, respectively, of the array. As a non-limiting example, each of the antigens of the array may be deposited on the support as a spot having a diameter of from about 10 microns to about 500 microns and, more particularly, from about 50 microns to about 300 microns.

The proteins may placed in arrays on the surface of the support using a pipetting device or a machine or device configured for placing liquid samples on a support, for example, using a commercially available microarrayer, such as those from Arrayit Corporation (Sunnyvale, Calif.); Genomic Solutions, Inc. (Ann Arbor, Mich.); Gene Machines (San Carlos, Calif.); Genetic MicroSystems, Inc. (Woburn, Mass.); GenePack DNA (Cambridge, UK); Genetix Ltd. (Christchurch, Dorset, UK); and Packard Instrument Company (Meriden, Conn.).

Relevant methods to array a series of proteins onto a surface include contact printing processes, non-contact printing processes and in silico protein synthesis arrayer processes. Commercially available instruments are available for both methods. In some embodiments, conventional contact printing processes, such as contact pin printing and microstamping, in which the printing device may physically contact a surface may be used to apply the proteins to the surface of a support. For example, a pin printing device such as that commercially available from Arrayit Corporation may be used to deposit spots having an average diameter of 65 microns or larger. As another non-limiting example, Genomic Solutions offers several nanoliter dispensing instruments that may dispense liquid volumes from 20 nL up to 250 µL from 96-, 384-, 1536-, 3456-, and 9600-well microtiter plates and place them precisely on a surface with densities up to 400 spots/cm$^2$. The instruments will spot onto surfaces in a variety of patterns. In additional embodiments, the protein antigens may be applied to the surface without physical contact between the printing device and the surface using conventional non-contact printing processes including, but not limited to, photochemistry-based methods, laser writing, electrospray deposition, and inkjet. As the name implies, inkjet technology utilizes the same principles as those used in inkjet printers. MicroFab Technologies, Inc. (Plano, Tex.), offers a ten-fluid print head that may dispense picoliter quantities of liquids onto a surface in a variety of patterns. An illustrative pattern for the present application would be a simple array ranging from 10×10 up to 100×100. The protein antigens may be applied to the surface using a serial deposition process or a parallel deposition process.

There are a number of methods that may be used to attach proteins or other antigens to the surface of a support. The simplest of these is simple adsorption through hydrophobic, ionic, and van der Waals forces. As a non-limiting example, bifunctional organosilanes may be used in attachment of proteins to the surface of the support (e.g., Thompson and Maragos, *Fiber-Optic Immunosensor for the Detection of Fumonisin $B_1$*, 44 J. Agric. Food Chem. 1041-1046 (1996)). One end of the organosilane reacts with exposed —OH groups on the surface of the support to form a silanol bond. The other end of the organosilane contains a group that is reactive with various groups on the protein surface, such as —NH$_2$ and —SH groups. This method of attaching proteins to the support results in the formation of a covalent linkage between the protein and the support. Other suitable methods that have been used for protein attachment to surfaces include arylazide, nitrobenzyl, and diazirine photochemistry methodologies. Exposure of the above chemicals to UV light causes the formation of reactive groups that may react with proteins to form a covalent bond. The arylazide chemistry forms a reactive nitrene group that may insert into C—H bonds, while the diazirine chemistry results in a reactive carbene group. The nitrobenzyl chemistry is referred to as caging chemistry whereby the caging group inactivates a reactive molecule. Exposure to UV light frees the molecule and makes it available for reaction. Still other methods for attaching proteins to supports are well known in the art, (e.g., S. S. Wong, *Chemistry of Protein Conjugation and Cross-Linking* CRC Press, 340, 1991).

Following attachment of the antigens on the support in the selected array, the support may be washed. The wash solution may include, for example, one or more of a surfactant or a non-specific protein such as bovine serum albumin (BSA). Appropriate liquids for washing include, but are not limited to, phosphate buffered saline (PBS) and the like, i.e., relatively low ionic strength, biocompatible salt solutions buffered at or near neutrality. Many of such appropriate wash liquids are known in the art or may be devised by a person skilled in the art without undue experimentation (e.g., N.E. Good and S. Izawa, *Hydrogen Ion Buffers,* 24 Methods Enzymology 53-68 (1972)).

The support may be processed for blocking of nonspecific binding of proteins and other molecules to the support. This blocking step may prevent the binding of antigens, antibodies, and the like to the support wherein such antigens, antibodies, or other molecules are not intended to bind. Blocking may reduce the background that might swamp out the signal, thus increasing the signal-to-noise ratio. The support may be blocked by incubating the support in a medium that contains inert molecules that bind to sites where nonspecific binding might otherwise occur. Examples of suitable blockers include, but are not limited to, bovine serum albumin, human albumin, gelatin, nonfat dry milk, polyvinyl alcohol, TWEEN® 20, and various commercial blocking buffers, such as SEABLOCK™ blocking buffer from EastCoast Bio, Inc., (West Berwick, Me.) and SUPERBLOCK® blocking buffer from Pierce Chemical Co., (Rockford, Ill.). In some embodiments, one or more of the suitable blockers may be incorporated into the wash solution described above.

Antibody Profile

The array may be contacted with a sample of the biological material to be tested. For example, the biological sample may be obtained from various bodily fluids and solids, including blood, saliva, semen, serum, plasma, urine, amniotic fluid, pleural fluid, cerebrospinal fluid, and mixtures thereof. These samples may be obtained according to methods well known in the art. Depending on the detection method used, it may be required to manipulate the biological sample to attain optimal reaction conditions. For example, the ionic strength or hydrogen ion concentration or the concentration of the biological sample may be adjusted for optimal immune complex formation, enzymatic catalysis, and the like.

As described in detail in U.S. Pat. No. 5,270,167 to Francoeur, when ISAs are allowed to react with a set of random antigens, a certain number of immune complexes form. For example, using a panel of about 1000 unique antigens, about 30 immune complexes between ISAs in a biological sample that has been diluted 20-fold may be detected. If the biological sample is undiluted, the total number of possible detectable immune complexes that could form would be greater than $10^{23}$. The total number of possible immune complexes may also be increased by selecting "larger" antigens, i.e., proteins instead of peptides) that have multiple epitopes. Therefore, it will be appreciated that depending on the antigens and number thereof used, the dilution of the biological sample, and the detection method, one skilled in the art may regulate the number of immune complexes that will form and be detected. As used herein, an "antibody profile" refers to the set of unique immune complexes that form and fail to form between the ISAs in the biological sample and the antigens in the array.

Detection and/or Quantification of Reactions

Methods for detecting antibody/antigen or immune complexes are well known in the art. The present invention may be modified by one skilled in the art to accommodate the various detection methods known in the art. The particular detection method chosen by one skilled in the art depends on several factors, including the amount of biological sample available, the type of biological sample, the stability of the biological sample, the stability of the antigen, and the affinity between the antibody and antigen. Moreover, as discussed above, depending on the detection methods chosen, it may be required to modify the biological sample. While these techniques are well known in the art, non-limiting examples of a few of the detection methods that may be used to practice the present invention are briefly described below.

There are many types of immunoassays known in the art. The most common types of immunoassay are competitive and non-competitive heterogeneous assays, such as, for example, enzyme-linked immunosorbent assays (ELISAs). In a non-competitive ELISA, unlabeled antigen is bound to a support. A biological sample may be combined with antigens bound to the reaction vessel, and antibodies (primary antibodies) in the biological sample may be allowed to bind to the antigens, forming the immune complexes. After the immune complexes have formed, excess biological sample may be removed and the array may be washed to remove nonspecifically bound antibodies. The immune complexes may then be reacted with an appropriate enzyme-labeled anti-immunoglobulin (secondary antibody). The secondary antibody reacts with antibodies in the immune complexes, not with other antigens bound to the array. Secondary antibodies specific for binding antibodies of different species, including humans, are well known in the art and are commercially available, such as from Sigma Chemical Co. (St. Louis, Mo.) and Santa Cruz Biotechnology, Inc. (Santa Cruz, Calif.). After an optional further wash, the enzyme substrate may be added. The enzyme linked to the secondary antibody catalyzes a reaction that converts the substrate into a product. When excess antigen is present, the amount of product is directly proportional to the amount of primary antibody present in the biological sample. By way of non-limiting example, the product may be fluorescent or luminescent, which may be measured using technology and equipment well known in the art. It is also possible to use reaction schemes that result in a colored product, which may be measured spectrophotometrically.

In other embodiments of the invention, the secondary antibody may not be labeled to facilitate detection. Additional antibodies may be layered (i.e., tertiary, quaternary, etc.) such that each additional antibody specifically recognizes the antibody previously added to the immune complex. Any one of these additional (i.e., tertiary, quaternary, etc.) may be labeled so as to allow detection of the immune complex as described herein.

Sandwich or capture assays may also be used to identify and quantify immune complexes. Sandwich assays are a mirror image of non-competitive ELISAs in that antibodies are bound to the solid phase and antigen in the biological sample is measured. These assays may be particularly useful in detecting antigens having multiple epitopes that are present at low concentrations. This technique requires excess antibody to be attached to a solid phase. The bound antibody is then incubated with the biological samples, and the antigens in the sample may be allowed to form immune complexes with the bound antibody. The immune complex is incubated with an enzyme-linked secondary antibody, which recognizes the same or a different epitope on the antigen as the primary antibody. Hence, enzyme activity is directly proportional to the amount of antigen in the biological sample. D. M. Kemeny and S. J. Challacombe, *ELISA and Other Solid Phase Immunoassays*, (John Wiley & Sons Ltd.) (1988).

Typical enzymes that may be linked to secondary antibodies include, but are not limited to, horseradish peroxidase, glucose oxidase, glucose-6-phosphate dehydrogenase, alkaline phosphatase, β-galactosidase, and urease. Secondary antigen-specific antibodies linked to various enzymes are commercially available from, for example, Sigma Chemical Co. and Amersham Life Sciences (Arlington Heights, Ill.).

Competitive ELISAs are similar to noncompetitive ELISAs except that enzyme linked antibodies compete with unlabeled antibodies in the biological sample for limited antigen binding sites. Briefly, a limited number of antigens may be bound to the support. Biological sample and enzyme-labeled antibodies may be added to the support. Antigen-specific antibodies in the biological sample compete with enzyme-labeled antibodies for the limited number of antigens bound to the support. After immune complexes have formed, non-specifically bound antibodies may be removed by washing, enzyme substrate is added, and the enzyme activity is measured. No secondary antibody is required. Because the assay is competitive, enzyme activity is inversely proportional to the amount of antibodies in the biological sample.

Another competitive ELISA may also be used within the scope of the present invention. In this embodiment, limited amounts of antibodies from the biological sample may be bound to the surface of the support as described herein. Labeled and unlabeled antigens may be then brought into contact with the support such that the labeled and unlabeled antigens compete with each other for binding to the antibodies on the surface of the support. After immune complexes have formed, nonspecifically bound antigens may be removed by washing. The immune complexes may be detected by incubation with an enzyme-linked secondary antibody, which recognizes the same or a different epitope on the antigen as the primary antibody, as described above. The activity of the enzyme is then assayed, which yields a signal that is inversely proportional to the amount of antigen present.

Homogeneous immunoassays may also be used when practicing the method of the present invention. Homogeneous immunoassays may be preferred for detection of low molecular weight compounds, such as hormones, therapeutic drugs, and illegal drugs that cannot be analyzed by other methods, or compounds found in high concentration. Homogeneous assays may be particularly useful because no separation step is necessary. R. C. Boguslaski et al., *Clinical Immunochemistry Principles of Methods and Applications*, (1984).

In homogeneous techniques, bound or unbound antigens may be enzyme-linked. When antibodies in the biological sample bind to the enzyme-linked antigen, steric hindrances inactivate the enzyme. This results in a measurable loss in enzyme activity. Free antigens (i.e., not enzyme-linked) compete with the enzyme-linked antigen for limited antibody binding sites. Thus, enzyme activity is directly proportional to the concentration of antigen in the biological sample.

Enzymes useful in homogeneous immunoassays include, but are not limited to, lysozyme, neuraminidase, trypsin, papain, bromelain, glucose-6-phosphate dehydrogenase, and β-galactosidase. T. Persoon, "Immunochemical Assays in the Clinical Laboratory," 5 Clinical Laboratory Science 31 (1992). Enzyme-linked antigens are commercially available or may be linked using various chemicals well known in the art, including glutaraldehyde and maleimide derivatives.

Prior antibody profiling technology involved an alkaline phosphatase labeled secondary antibody with 5-bromo-4-chloro-3'-indolylphosphate p-toluidine salt (BCIP) and nitro-blue tetrazolium chloride (NBT), both of which are commercially available from a variety of sources, such as from Pierce Chemical Co. (Rockford, Ill.). The enzymatic reaction forms an insoluble colored product that is deposited on the surface of membrane strips to form bands wherever antigen-antibody complexes occur. As a non-limiting example, the array may be scanned to detect a colored product using one of a variety of conventional desktop scanners, which are commercially available from a variety of sources, such as from Canon U.S.A. (Lake Success, N.Y.). The intensity of the colored product may be quantified by calculating the median feature pixel intensity minus median background pixel intensity.

As another non-limiting example, gold nanoparticle labeled antibodies may be employed and may be detected using a scanning, transmission electron microscopy, and/or dark-field zoom stereomicroscopy. Compared to conventional fluorescent labels, the gold nanoparticles scatter incident white light to generate monochromatic light which may be easily detected. The light intensity generated by the gold nanoparticles may be up to 100,000 times greater than that generated by fluorescent-labeled molecules. For example, the gold nanoparticles may be detected using a conventional desktop scanner. Han et al., *Detection of Analyte Binding to Microarrays Using Gold Nanoparticle Labels and a Desktop Scanner*, 3 Lab Chip 329; 329-332 (2003).

Fluorescent immunoassays may also be used when practicing the method of the present invention. Fluorescent immunoassays are similar to ELISAs except the enzyme is substituted for fluorescent compounds called fluorophores or fluorochromes. These compounds have the ability to absorb energy from incident light and emit the energy as light of a longer wavelength and lower energy. Fluorescein and rhodamine, usually in the form of isothiocyanates that may be readily coupled to antigens and antibodies, are most commonly used in the art. D. P. Stites et al., *Basic and Clinical Immunology*, (1994). Fluorescein absorbs light of 490 to 495 nm in wavelength and emits light at 520 nm in wavelength. Tetramethylrhodamine absorbs light of 550 nm in wavelength and emits light at 580 nm in wavelength. Illustrative fluorescence-based detection methods include ELF-97 alkaline phosphatase substrate (Molecular Probes, Inc., Eugene, Oreg.); PBXL-1 and PBXL-3 (phycobilisomes conjugated to streptavidin) (Martek Biosciences Corp., Columbia, Md.); FITC (fluorescein isothiocyanate) and Texas Red labeled goat anti-human IgG (Jackson ImmunoResearch Laboratories, Inc., West Grove, Pa.); and B-Phycoerythrin and R-Phycoerythrin conjugated to streptavidin (Molecular Probes Inc.). ELF-97 is a nonfluorescent chemical that is digested by alkaline phosphatase to form a fluorescent molecule. Because of turnover of the alkaline phosphatase, use of the ELF-97 substrate results in signal amplification. Fluorescent molecules attached to secondary antibodies do not exhibit this amplification.

Phycobiliproteins isolated from algae, porphyrins, and chlorophylls, which all fluoresce at about 600 nm, are also being used in the art. I. Hemmila, *Fluoroimmunoassays and Immunofluorometric Assays*, 31 Clin. Chem. 359 (1985); U.S. Pat. No. 4,542,104. Phycobiliproteins and derivatives thereof are commercially available under the names R-phycoerythrin (PE) and QUANTUM RED™ from Sigma Chemical Co.

In addition, Cy-conjugated secondary antibodies and antigens may be useful in immunoassays and are commercially available. Cy3, for example, is maximally excited at 554 nm and emits light at between 568 and 574 nm. Cy3 is more hydrophilic than other fluorophores and thus has less of a tendency to bind nonspecifically or aggregate. Cy-conjugated compounds are commercially available from Amersham Life Sciences.

Illustrative luminescence-based detection methods include CSPD® and CDP star alkaline phosphatase substrates from Roche Molecular Biochemicals, (Indianapolis, Ind.) and SUPERSIGNAL® horseradish peroxidase substrate from Pierce Chemical Co., (Rockford, Ill.).

Chemiluminescence, electroluminescence, and electrochemiluminescence (ECL) detection methods may also be attractive means for quantifying antigens and antibodies in a biological sample. Luminescent compounds have the ability to absorb energy, which is released in the form of visible light upon excitation. In chemiluminescence, the excitation source is a chemical reaction; in electroluminescence the excitation source is an electric field; and in ECL an electric field induces a luminescent chemical reaction.

Molecules used with ECL detection methods generally comprise an organic ligand and a transition metal. The organic ligand forms a chelate with one or more transition metal atoms forming an organometallic complex. Various organometallic and transition metal-organic ligand complexes have been used as ECL labels for detecting and quantifying analytes in biological samples. Due to their thermal, chemical, and photochemical stability, their intense emissions and long emission lifetimes, ruthenium, osmium, rhenium, iridium, and rhodium transition metals are favored in the art. The types of organic ligands are numerous and include anthracene and polypyridyl molecules and heterocyclic organic compounds. For example, bipyridyl, bipyrazyl, terpyridyl, and phenanthrolyl, and derivatives thereof, are common organic ligands in the art. A common organometallic complex used in the art includes tris-bipyridine ruthenium (II), commercially available from IGEN, Inc. (Rockville, Md.) and Sigma Chemical Co.

ECL may be performed under aqueous conditions and under physiological pH, thus minimizing biological sample handling. J. K. Leland et al., *Electrogenerated Chemiluminescence: An Oxidative-Reduction Type ECL Reactions Sequence Using Triprophyl Amine*, 137 J. Electrochemical Soc. 3127-3131 (1990); WO 90/05296; and U.S. Pat. No. 5,541,113. Moreover, the luminescence of these compounds may be enhanced by the addition of various cofactors, such as amines.

A tris-bipyridine ruthenium (II) complex, for example, may be attached to a secondary antibody using strategies well known in the art, including attachment to lysine amino groups, cysteine sulfhydryl groups, and histidine imidazole groups. In a typical ELISA immunoassay, secondary antibodies would recognize antibodies bound to antigens, but not unbound antigens. After washing nonspecific binding complexes, the tris-bipyridine ruthenium (II) complex may be excited by chemical, photochemical, and electrochemical excitation means, such as by applying current to the array (e.g., WO 86/02734). The excitation would result in a double oxidation reaction of the tris-bipyridine ruthenium (II) complex, resulting in luminescence that could be detected by, for example, a photomultiplier tube. Instruments for detecting luminescence are well known in the art and are commercially available, for example, from IGEN, Inc. (Rockville, Md.).

Solid state color detection circuitry may also be used to monitor the color reactions on the array and, on command, compare the color patterns before and after the sample application. A color camera image may also be used and the pixel information analyzed to obtain the same information.

Still another method involves detection using a surface plasmon resonance (SPR) chip. The surface of the chip is scanned before and after sample application and a comparison is made. The SPR chip relies on the refraction of light when the molecules of interest may be exposed to a light source. Each molecule has its own refraction index by which it may be identified. This method requires precise positioning and control circuitry to scan the chip accurately.

Yet another method involves a fluid rinse of the array with a fluorescing reagent. The antigens that combine with the biological sample will fluoresce and may be detected with a charge-coupled device (CCD) array. The output of such a CCD array is analyzed to determine the unique pattern associated with each sample. Speed is not a factor with any of the methods since the chemical combining of sample and reference takes minutes to occur.

Moreover, array scanners are commercially available, such as from Genetic MicroSystems, Inc. The GMS 418 Array Scanner uses laser optics to rapidly move a focused beam of light over the array. This system uses a dual-wavelength system including high-powered, solid-state lasers that generate high excitation energy to allow for reduced excitation time. At a scanning speed of 30 Hz, the GMS 418 may scan a 22×75-mm slide with 10-µm resolution in about four minutes.

Software for image analysis obtained with an array scanner is readily available. Available software packages include Ima-Gene (BioDiscovery, Los Angeles, Calif.); ScanAlyze (available at no charge; developed by Mike Eisen, Stanford University, Palo Alto, Calif.); De-Array (developed by Yidong Chen and Jeff Trent of the National Institutes of Health; used with IP Lab from Scanalytics, Inc., Fairfax, Va.); Pathways (Research Genetics, Huntsville, Ala.); GEM Tools (Incyte Pharmaceuticals, Inc., Palo Alto, Calif.); and Imaging Research (Amersham Pharmacia Biotech, Inc., Piscataway, N.J.).

Once interactions between the antigens and antibodies have been identified and quantified, the signals may be digitized. The digitized antibody profile may serve as a signature that identifies the source of the biological sample. Depending on the array used, the digitized data may take numerous forms. For example, the array may include 10 columns and 10 rows for a total number of 100 spots, each including at least one antigen. After the biological sample including the antibodies is added to the array and allowed to incubate, interactions between antigens and antibodies in the biological sample may be identified and quantified. In each spot, an interaction between the antigen in the spot and the antibody in the biological sample will either result in or not result in a quantifiable signal. In one embodiment, the results of the antibody profile may be digitized by, by way of non limiting example, ascribing each one of the 100 spots a numerical value of either "0," if a quantifiable signal was not obtained, or "1," if a quantifiable signal was obtained. Using this method, the digitized antibody profile may comprise a unique set of zeroes and ones. It will be understood that the use of 1 and 0 is merely exemplary and that any set of values or indicators may be used to signify the absence, presence, or intensity of a particular signal.

The numerical values "0" or "1" may, of course, be normalized to signals obtained in internal control spots so that digitized antibody profiles obtained at a later time may be properly compared. For example, one or several of the spots may contain a known antigen, which will remain constant over time. Therefore, if a subsequent biological sample is more or less dilute than a previous biological sample, the signals may be normalized using the signals from the known antigen.

It will be appreciated by one skilled in the art that other methods of digitizing the antibody profile exist and may be used. For example, rather than ascribing each spot with a numerical value of "0" or "1," the numerical value may be incremental and directly proportional to the strength of the signal.

Statistical Analysis

The antibody profiles obtained from the plurality of individuals may be analyzed using conventional discriminant analysis methods to determine proteins useful in discriminating or identifying an individual from one or more other individuals. For example, discriminant proteins may be determined using forward selection, backward elimination, or stepwise selection to determine a subset of proteins that best reveals differences among the classes (i.e., the individuals). The STEPDISC procedure, which is available from SAS Institute, Inc. (Cary, N.C.), may be used to perform a stepwise discriminant analysis to select a subset of the proteins useful in discriminating among individuals. Signals from a set of proteins that make up each class may be assumed to be multivariate normal with a common covariance matrix.

Using the STEPDISC procedure, variables (in particular, signals from particular proteins) may be chosen to enter or leave the model according to the significance level of an F-test from an analysis of covariance, where the variables already chosen act as covariates and the variable under consideration is the dependent variable. In other embodiments, a variable could be chosen to enter or leave the model according to whether the squared partial correlation for its prediction using the class variable (and controlling for the effects of the other variables already in the model) is high.

In some embodiments, the discriminant proteins useful in discriminating or identifying an individual may be determined by calculating various discriminant functions for classifying observations using the protein signals. Linear or quadratic discriminant functions may be used for data with approximately multivariate normal within-class distributions. Nonparametric methods may be used without making any assumptions about these distributions.

One or more of the discriminant proteins may be used to identify an individual, to distinguish between individuals, or to establish or rule out the source of a biological sample. In some embodiments, one or more of the discriminant proteins may be used as part of a test panel. For example, discriminant proteins may be immobilized on a support in the form of an array as described above to form a protein array useful in discriminating among individuals and/or sources of a biological sample. However, other methods of detecting an interaction between a discriminant protein and an antibody present in a biological sample, such as conventional protein affinity chromatography methods, affinity blotting methods, immunoprecipitation methods, and cross-linking methods, may also be used. In embodiments, the array or test panel may be used to generate an antibody profile which may be used to distinguish between individuals in a population, or to establish or rule out the source of a biological sample within a population, wherein the population may comprise 1 million, 10 million, 100 million, 1 billion, 10 billion, 100 billion, or more individuals.

The array may include several discriminant proteins, each of which may be immobilized on a support. The array may include less than about 200, 175, 150, 125, 100, 75, or 50 discriminant proteins. For example, the test panel for discriminating or identifying an individual may include from about 20 to about 90 discriminant proteins, and more particularly, from about 45 to about 80 discriminant proteins. With "X" different profiles that are each independent, the probability that no two different people have the same profile among "m" people can be shown to be equal to $\exp[-m*m/(2\times)]$. As a non-limiting example, greater than about 76 independent discriminant proteins may be used to distinguish an individual among a population of about 10 billion individuals, the probability of a match between two different individuals being less than about 0.0001. As another non-limiting example, greater than about 86 independent discriminant proteins may be used to distinguish an individual among a population of about 100 billion individuals, the probability of a match between two different individuals being less than about 0.0001. Examples of discriminant proteins include, but are not limited to, those proteins presented in Table 1.

In an embodiment of the invention, a protein array including discriminant proteins may be used for forensic analysis for matching a biological sample to an individual such as, for example, a criminal suspect. Forensic samples obtained from crime scenes are often subject to drying of the samples, small sample sizes, mixing with samples from more than one individual, adulteration with chemicals, and the like. The present method provides the advantages of rapid analysis, simplicity, low cost, and accuracy for matching forensic samples with suspects. For example, the forensic sample and a sample from one or more suspects may be obtained according to methods well known in the art. The samples may be tested against the array and compared. If the discriminant proteins obtained from the samples match, it may be concluded that the forensic sample was obtained from the matching suspect. If no match of discriminant proteins is obtained, then none of the suspects was the source of the forensic sample.

Example

Serum samples from ninety-four (94) individuals were profiled against a high throughput protein array with over 8000 proteins and the data from these chips was statistically analyzed to determine proteins useful for discriminating among sets of individuals in a population. The ninety-four (94) individuals included nineteen (19) Asian individuals, twenty (20) African American individuals, twenty (20) Native American individuals, and thirty-five (35) Caucasian individuals. For quality assurance (QA), the arrays contained the immobilized proteins in pairs on a support. Thus, each array provided two opportunities for antigen/antibody binding for each protein.

The serum samples were diluted 1:150 and used to probe human ProtoArray™. The arrays were blocked for 1 hour and then incubated with the serum samples for 90 minutes at about 4° C. without shaking. The arrays were then transferred to ice and washed about three times by adding about 20 ml buffer (1×PBS, 5 mM $MgCl_2$, 0.5 mM DTT, 0.05% Triton X-100, 5% Glycerol, 1% BSA) to the arrays, incubating the arrays with the buffer for 8 minutes at 4° C., and decanting the buffer from the arrays by inverting. The arrays were incubated with anti-human IgG antibody conjugated to AlexaFluor 647 for about 90 minutes, washed as above and dried. The arrays were scanned using a ScanArray Express® 3.0 HT microarray scanner, which is available commercially from Perkin Elmer, Inc. (Waltham, Mass.). The images were captured from the microarray scanner using a 633 nm laser with the scanner set to 10 µm resolution. Following scanning, data was acquired using ImaGene 8.0 microarray analysis software from BioDiscovery (El Segundo, Calif.). Background-subtracted signals from each population were normalized utilizing a quantile normalization strategy. Subjects were distinguished from one another using conventional discriminant analysis. The STEPDISC procedure from SAS Institute, Inc. was utilized to identify discriminant proteins based on the logarithms of the intensities detected. The discriminant proteins of interest were identified as significant in distinguishing between individuals. A list of 80 discrimininating proteins from among the over 8,000 on the arrays was determined. The 80 discriminating proteins are listed in Table 1.

TABLE 1

| SEQ ID NO | Protein ID | SelOrdAll | MinPSeeOrNot | sRatio | maxCorrAfter |
| --- | --- | --- | --- | --- | --- |
| SEQ ID NO: 1 | PM_2149 | 16 | 0.45 | 22.1 | 0.683 |
| SEQ ID NO: 2 | PM_2151 | 99 | 0.25 | 13.4 | 0.585 |
| SEQ ID NO: 3 | BC010125.1 | 62 | 0.23 | 15.6 | 0.500 |
| SEQ ID NO: 4 | BC011414.1 | 15 | 0.40 | 19.9 | 0.482 |
| SEQ ID NO: 5 | BC012945.1 | 38 | 0.33 | 18.4 | 0.570 |
| SEQ ID NO: 6 | BC014409.1 | — | 0.32 | 10.7 | 0.448 |
| SEQ ID NO: 7 | BC015219.1 | 76 | 0.29 | 15.6 | 0.652 |
| SEQ ID NO: 8 | BC016470.2 | 74 | 0.19 | 14.6 | 0.579 |
| SEQ ID NO: 9 | BC018206.1 | 31 | 0.38 | 16.1 | 0.551 |
| SEQ ID NO: 10 | BC018404.1 | 93 | 0.27 | 19.0 | 0.754 |
| SEQ ID NO: 11 | BC019039.2 | 33 | 0.41 | 17.2 | 0.544 |
| SEQ ID NO: 12 | BC019315.1 | 27 | 0.48 | 17.8 | 0.846 |
| SEQ ID NO: 13 | BC021189.2 | 29 | 0.34 | 17.2 | 0.488 |
| SEQ ID NO: 14 | BC023152.1 | 6 | 0.10 | 25.3 | 0.752 |
| SEQ ID NO: 15 | BC026175.1 | 50 | 0.39 | 15.6 | 0.582 |
| SEQ ID NO: 16 | BC026346.1 | 78 | 0.48 | 16.4 | 0.360 |
| SEQ ID NO: 17 | BC032825.2 | 13 | 0.10 | 18.9 | 0.491 |
| SEQ ID NO: 18 | BC033711.1 | 72 | 0.29 | 14.6 | 0.567 |
| SEQ ID NO: 19 | BC036123.1 | 101 | 0.35 | 15.0 | 0.649 |
| SEQ ID NO: 20 | BC040949.1 | 45 | 0.37 | 17.9 | 0.523 |
| SEQ ID NO: 21 | BC050377.1 | 70 | 0.14 | 11.0 | 0.310 |
| SEQ ID NO: 22 | BC052805.1 | 56 | 0.29 | 16.6 | 0.501 |
| SEQ ID NO: 23 | BC053602.1 | 42 | 0.32 | 16.1 | 0.621 |
| SEQ ID NO: 24 | BC060824.1 | 12 | 0.28 | 19.4 | 0.421 |
| SEQ ID NO: 25 | NM_015138.2 | 91 | 0.33 | 13.3 | 0.607 |
| SEQ ID NO: 26 | NM_175887.2 | 34 | 0.43 | 15.4 | 0.537 |
| SEQ ID NO: 27 | NM_000394.2 | 44 | 0.38 | 20.2 | 0.737 |
| SEQ ID NO: 28 | NM_000723.3 | 200 | 0.22 | 9.4 | 0.580 |
| SEQ ID NO: 29 | NM_001008220.1 | 17 | 0.22 | 21.7 | 0.405 |
| SEQ ID NO: 30 | NM_001106.2 | 22 | 0.41 | 20.3 | 0.303 |
| SEQ ID NO: 31 | NM_001312.2 | 81 | 0.42 | 13.2 | 0.619 |
| SEQ ID NO: 32 | NM_001537.1 | 84 | 0.49 | 23.5 | 0.733 |
| SEQ ID NO: 33 | NM_002737 | 73 | 0.47 | 10.0 | 0.300 |
| SEQ ID NO: 34 | NM_002740 | 79 | 0.28 | 12.4 | 0.620 |
| SEQ ID NO: 35 | NM_002744 | 3 | 0.42 | 22.4 | 0.215 |
| SEQ ID NO: 36 | NM_003907.1 | 57 | 0.37 | 14.8 | 0.440 |
| SEQ ID NO: 37 | NM_003910.2 | 63 | 0.12 | 12.7 | 0.594 |
| SEQ ID NO: 38 | NM_004064.2 | 54 | 0.20 | 13.8 | 0.422 |
| SEQ ID NO: 39 | NM_004394.1 | 58 | 0.48 | 16.3 | 0.641 |
| SEQ ID NO: 40 | NM_004845.3 | 30 | 0.25 | 18.0 | 0.432 |
| SEQ ID NO: 41 | NM_004965.3 | 97 | 0.46 | 11.4 | 0.648 |
| SEQ ID NO: 42 | NM_005030 | 95 | 0.41 | 14.2 | 0.683 |
| SEQ ID NO: 43 | NM_005246.1 | 77 | 0.22 | 9.3 | 0.625 |
| SEQ ID NO: 44 | NM_006007.1 | 80 | 0.24 | 13.3 | 0.417 |
| SEQ ID NO: 45 | NM_006218.2 | 90 | 0.24 | 8.2 | 0.573 |
| SEQ ID NO: 46 | NM_006628.4 | 66 | 0.29 | 15.0 | 0.538 |

TABLE 1-continued

| SEQ ID NO | Protein ID | SelOrdAll | MinPSeeOrNot | sRatio | maxCorrAfter |
|---|---|---|---|---|---|
| SEQ ID NO: 47 | NM_006819.1 | 4 | 0.22 | 17.9 | 0.356 |
| SEQ ID NO: 48 | NM_012472.1 | 11 | 0.49 | 23.0 | 0.578 |
| SEQ ID NO: 49 | NM_014240.1 | 19 | 0.44 | 18.9 | 0.459 |
| SEQ ID NO: 50 | NM_014245.1 | 18 | 0.29 | 22.9 | 0.676 |
| SEQ ID NO: 51 | NM_014460.2 | 21 | 0.32 | 19.7 | 0.414 |
| SEQ ID NO: 52 | NM_014622.4 | 65 | 0.49 | 15.7 | 0.566 |
| SEQ ID NO: 53 | NM_014891.1 | 32 | 0.23 | 19.1 | 0.343 |
| SEQ ID NO: 54 | NM_014943.3 | 71 | 0.16 | 12.7 | 0.519 |
| SEQ ID NO: 55 | NM_015149.2 | 96 | 0.18 | 11.4 | 0.665 |
| SEQ ID NO: 56 | NM_015417.2 | 8 | 0.12 | 19.3 | 0.353 |
| SEQ ID NO: 57 | NM_015509.2 | 43 | 0.23 | 12.8 | 0.554 |
| SEQ ID NO: 58 | NM_016096.1 | 41 | 0.28 | 16.0 | 0.516 |
| SEQ ID NO: 59 | NM_016520.1 | 60 | 0.38 | 13.3 | 0.471 |
| SEQ ID NO: 60 | NM_017855.2 | 69 | 0.29 | 14.2 | 0.578 |
| SEQ ID NO: 61 | NM_017949.1 | 49 | 0.16 | 16.2 | 0.630 |
| SEQ ID NO: 62 | NM_018326.1 | 26 | 0.39 | 17.5 | 0.254 |
| SEQ ID NO: 63 | NM_018584.4 | 7 | 0.37 | 21.7 | 0.448 |
| SEQ ID NO: 64 | NM_024718.2 | 103 | 0.17 | 11.0 | 0.495 |
| SEQ ID NO: 65 | NM_024826.1 | 20 | 0.41 | 17.8 | 0.328 |
| SEQ ID NO: 66 | NM_025241.1 | 48 | 0.43 | 13.2 | 0.268 |
| SEQ ID NO: 67 | NM_032345.1 | 85 | 0.16 | 13.4 | 0.765 |
| SEQ ID NO: 68 | NM_032368.3 | 39 | 0.36 | 19.2 | 0.635 |
| SEQ ID NO: 69 | NM_079420.1 | 51 | 0.45 | 14.0 | 0.643 |
| SEQ ID NO: 70 | NM_080390.3 | 86 | 0.23 | 15.3 | 0.582 |
| SEQ ID NO: 71 | NM_138623.2 | 67 | 0.12 | 14.4 | 0.538 |
| SEQ ID NO: 72 | NM_145796.2 | 64 | 0.26 | 11.4 | 0.590 |
| SEQ ID NO: 73 | NM_153757.1 | 46 | 0.46 | 16.8 | 0.402 |
| SEQ ID NO: 74 | NM_177973.1 | 10 | 0.26 | 18.5 | 0.290 |
| SEQ ID NO: 75 | NM_178010.1 | 9 | 0.31 | 16.8 | 0.124 |
| SEQ ID NO: 76 | NM_199124.1 | 28 | 0.38 | 14.0 | 0.252 |
| SEQ ID NO: 77 | NM_201262.1 | 14 | 0.27 | 17.5 | 0.118 |
| SEQ ID NO: 78 | NM_203284.1 | 5 | 0.31 | 26.9 | 0.277 |
| SEQ ID NO: 79 | NM_205853.1 | 25 | 0.44 | 17.7 | 0.208 |
| SEQ ID NO: 80 | NM_212540.1 | 75 | 0.17 | 12.4 | — |

The discriminant proteins of Table 1 were selected to discriminate an individual based on the primary criterion that the logarithms of the associated intensity signals appear as selected variables in a STEPDISC model. Several STEPDISC models were tested. One used only data from the first QA sample associated with each protein. A second model used only data from the other QA sample. A third model used average values, and a fourth used all the data (a total of 198 sets of protein intensity data from 99 non-blank arrays). The "SelOrdAll" column in Table 1 shows the order of selection of proteins from the fourth model. The values are ranked, so "1" corresponds to the first protein selected, "2" for the second, and so forth. The protein (SEQ. ID NO: 6) with no value in this column was selected in a fifth STEPDISC model that used just data from subjects with replication (specifically, data from the two individuals with more than one array in the data set were used in this model). The fourth run identified a total of 197 proteins. The filter sought proteins among the first 100 selected using this model. For later protein lists that needed more proteins than just the 80, additional proteins selected in the first three STEPDISC models were included in the screening list.

The initial list was refined using three additional filters. First, proteins retained on the list had to have the between-subject standard deviation as the largest of the estimated standard deviations. The standard deviations for this filter were obtained using a conventional "components of variance" analysis for each protein that sought variation between subjects, arrays, spots on the array and the QA sampling variation. The ratio of the between-subject estimate divided by the QA sample standard deviation estimate is shown in the "sRatio" column of Table 1. This ratio was used as a further criteria in narrowing the selection (see further below).

The second criterion used in refining the list of discriminant proteins to get just 80 was related to the probability of detection. For the example embodiment of the invention, a median intensity of greater than 1500 was assumed to be required in order to observe the presence of antigen/antibody bonding for a protein. The fraction of array data exceeding 1500 was tabulated for each protein. In initial data screening, this fraction was required to be at least 0.1 and less than 0.9. If nearly all the sample intensities are invisible, or nearly all are visible, there is less potential for discriminating between people. The minimum of the probability of visibility, and 1-this probability, was used further as described below. This attribute of a protein is denoted as "MinPSeeOrNot" in Table 1.

To determine the subset of 45 discriminant proteins listed in Table 2 below, pairwise correlation coefficients for all pairs among the 80 proteins were evaluated. The correlations were estimated using the data set of people with just one array per person (92 arrays), so that complete independence in the results would be ideal. The correlations were estimated using JMP® statistical software from SAS Institute. For each of the 80 proteins, a maximum correlation was identified. The pair of proteins in the array with the maximum correlation of all of these was identified. The protein in this pair with other relatively high correlations was identified as the worst protein from the correlation standpoint. This protein was recorded and then all correlations associated with it were removed from further consideration. This process was repeated using the remaining data, leading to identification of the second-worst protein and its highest correlation, conditioned on the first (worst) protein being omitted. This process was repeated until only two proteins remained in the set of data being considered. These are the two most "independent" proteins among the set of 80. The maximum correlation estimated between a given protein and some other protein, given that the more highly-correlated proteins have been removed from the data set, is shown as "MaxCorrAfter" in Table 1. The most discriminating proteins have the lowest values for "MaxCorrAfter."

The 45 discriminant proteins in Table 2 were identified using the following cutoff values for the three filters discussed above: sRatio greater than or equal to about 11, a "MaxCorrAfter" less than about 0.6, and "MinPSeeOrNot" greater than about 0.2. The numbers in this filter were selected by trial and error to retain exactly 45 proteins.

TABLE 2

45 proteins, sorted on sRatio.

| Protein ID | SEQ ID NO | selOrdAll | MinPSeeOrNot | sRatio | maxCorrAfter |
|---|---|---|---|---|---|
| NM_203284.1 | SEQ ID NO: 78 | 5 | 0.3131 | 26.9 | 0.277 |
| NM_012472.1 | SEQ ID NO: 48 | 11 | 0.4949 | 23.0 | 0.578 |
| NM_002744 | SEQ ID NO: 35 | 3 | 0.4192 | 22.4 | 0.215 |
| NM_018584.4 | SEQ ID NO: 63 | 7 | 0.3737 | 21.7 | 0.448 |
| NM_001008220.1 | SEQ ID NO: 29 | 17 | 0.2172 | 21.7 | 0.405 |
| NM_001106.2 | SEQ ID NO: 30 | 22 | 0.4091 | 20.3 | 0.303 |
| BC011414.1 | SEQ ID NO: 4 | 15 | 0.4040 | 19.9 | 0.482 |
| NM_014460.2 | SEQ ID NO: 51 | 21 | 0.3182 | 19.7 | 0.414 |
| BC060824.1 | SEQ ID NO: 24 | 12 | 0.2828 | 19.4 | 0.421 |
| NM_014891.1 | SEQ ID NO: 53 | 32 | 0.2323 | 19.1 | 0.343 |
| NM_014240.1 | SEQ ID NO: 49 | 19 | 0.4444 | 18.9 | 0.459 |
| NM_177973.1 | SEQ ID NO: 74 | 10 | 0.2576 | 18.5 | 0.290 |
| BC012945.1 | SEQ ID NO: 5 | 38 | 0.3333 | 18.4 | 0.570 |
| NM_004845.3 | SEQ ID NO: 40 | 30 | 0.2525 | 18.0 | 0.432 |
| NM_006819.1 | SEQ ID NO: 47 | 4 | 0.2222 | 17.9 | 0.356 |
| BC040949.1 | SEQ ID NO: 20 | 45 | 0.3737 | 17.9 | 0.523 |
| NM_024826.1 | SEQ ID NO: 65 | 20 | 0.4141 | 17.8 | 0.328 |
| NM_205853.1 | SEQ ID NO: 79 | 25 | 0.4394 | 17.7 | 0.208 |
| NM_018326.1 | SEQ ID NO: 62 | 26 | 0.3939 | 17.5 | 0.254 |
| NM_201262.1 | SEQ ID NO: 77 | 14 | 0.2727 | 17.5 | 0.118 |
| BC021189.2 | SEQ ID NO: 13 | 29 | 0.3434 | 17.2 | 0.488 |
| BC019039.2 | SEQ ID NO: 11 | 33 | 0.4091 | 17.2 | 0.544 |
| NM_178010.1 | SEQ ID NO: 75 | 9 | 0.3081 | 16.8 | 0.124 |
| NM_153757.1 | SEQ ID NO: 73 | 46 | 0.4596 | 16.8 | 0.402 |
| BC052805.1 | SEQ ID NO: 22 | 56 | 0.2879 | 16.6 | 0.501 |
| BC026346.1 | SEQ ID NO: 16 | 78 | 0.4798 | 16.4 | 0.360 |
| BC018206.1 | SEQ ID NO: 9 | 31 | 0.3838 | 16.1 | 0.551 |
| NM_016096.1 | SEQ ID NO: 58 | 41 | 0.2828 | 16.0 | 0.516 |
| NM_014622.4 | SEQ ID NO: 52 | 65 | 0.4899 | 15.7 | 0.566 |
| BC026175.1 | SEQ ID NO: 15 | 50 | 0.3889 | 15.6 | 0.582 |
| BC010125.1 | SEQ ID NO: 3 | 62 | 0.2323 | 15.6 | 0.500 |
| NM_175887.2 | SEQ ID NO: 26 | 34 | 0.4293 | 15.4 | 0.537 |
| NM_080390.3 | SEQ ID NO: 70 | 86 | 0.2273 | 15.3 | 0.582 |
| NM_006628.4 | SEQ ID NO: 46 | 66 | 0.2929 | 15.0 | 0.538 |
| NM_003907.1 | SEQ ID NO: 36 | 57 | 0.3737 | 14.8 | 0.440 |
| BC033711.1 | SEQ ID NO: 18 | 72 | 0.2929 | 14.6 | 0.567 |
| NM_017855.2 | SEQ ID NO: 60 | 69 | 0.2879 | 14.2 | 0.578 |
| NM_199124.1 | SEQ ID NO: 76 | 28 | 0.3788 | 14.0 | 0.252 |
| NM_004064.2 | SEQ ID NO: 38 | 54 | 0.2020 | 13.8 | 0.422 |
| PM_2151 | SEQ ID NO: 2 | 99 | 0.2475 | 13.4 | 0.585 |
| NM_016520.1 | SEQ ID NO: 59 | 60 | 0.3838 | 13.3 | 0.471 |
| NM_006007.1 | SEQ ID NO: 44 | 80 | 0.2424 | 13.3 | 0.417 |
| NM_025241.1 | SEQ ID NO: 66 | 48 | 0.4343 | 13.2 | 0.268 |
| NM_015509.2 | SEQ ID NO: 57 | 43 | 0.2273 | 12.8 | 0.554 |
| NM_145796.2 | SEQ ID NO: 72 | 64 | 0.2576 | 11.4 | 0.590 |

While the invention is susceptible to various modifications and implementation in alternative forms, specific embodiments have been shown by way of non-limiting example in the drawings and have been described in detail herein. However, it should be understood that the invention is not intended to be limited to the particular forms disclosed. Rather, the invention includes all modifications, equivalents, and alternatives falling within the scope of the invention as defined by the following appended claims and their legal equivalents.

What is claimed is:

1. A protein array for identifying an individual comprising proteins immobilized on a support, wherein no more than about 200 proteins are in the array, wherein each protein is known, wherein each protein is immobilized at a known predetermined location on the support, and wherein each protein is useful in identifying an individual.

2. The protein array of claim 1, wherein each of the proteins is immobilized on the support to form a spot having a diameter of greater than about at least 50 microns to form an array.

3. The protein array of claim 1, wherein at least one of the proteins is one of SEQ ID NOs: 1-80, or a fragment thereof comprising an epitope.

4. The protein array of claim 1, wherein at least one of the proteins is one of SEQ ID NOs: 1-45, or a fragment thereof comprising an epitope.

5. The protein array of claim 1, wherein the array comprises each of the proteins of SEQ ID NOs: 1-80.

6. The protein array of claim 1, wherein the array comprises each of the proteins of SEQ ID NOs: 1-45.

7. The protein array of claim 1, wherein less than about 100 proteins are immobilized on the support.

8. The protein array of claim 1, wherein about from 45 to about 80 proteins are immobilized on the support.

9. A method for analyzing biological material having individual-specific antibodies, the method comprising:
   obtaining a sample of the biological material having individual-specific antibodies;
   contacting the array of claim 1 with the sample to bind at least a portion of the individual-specific antibodies to the multiple proteins of the array, to form immune complexes;
   applying at least one detection agent to the array, the detection agent comprising at least one interacting protein conjugated to a marker to detect the immune complexes;
   washing the support to remove non-immobilized individual-specific antibodies and the detection agent; and
   detecting the immune complexes on the array to obtain an antibody profile.

10. The method of claim 9, wherein obtaining a sample of the biological material having individual-specific antibodies comprises obtaining a plurality of samples from each of a plurality of individuals.

11. The method of claim 9, wherein no more than about 100 proteins are in the array.

12. The method of claim 9, wherein each of the proteins of the array has a spot diameter sufficient to be detected with a color scanner.

13. The method of claim 9, wherein each of the proteins of the array has a spot diameter of at least 300 microns.

14. The method of claim 9, wherein obtaining a sample of a biological material comprises obtaining a sample of a biological material selected from the group of biological material consisting of tissue, blood, saliva, urine, perspiration, tears, semen, serum, plasma, amniotic fluid, pleural fluid, cerebrospinal fluid, and combinations thereof.

15. The method of claim 9, wherein applying at least one detection agent to the array comprises applying a detection agent comprising at least one interacting protein conjugated to at least one of a chemiluminescent marker, a fluorescent marker, and a colorigenic marker.

16. The method of claim 9, wherein detecting the immune complexes on the array to obtain an antibody profile comprises detecting at least one of a chemiluminescent marker, a fluorescent marker, and a colorigenic marker using a portable device.

17. The method of claim 9, further comprising comparing the antibody profile to a known antibody profile obtained from an individual.

18. A method for analyzing biological material comprising antibodies, the method comprising:
   obtaining a sample of a biological material comprising antibodies;
   contacting the sample with the array of claim 1 to bind at least a portion of the antibodies to the proteins to form immune complexes;
   applying at least one detection agent to the array, the detection agent comprising at least one interacting protein conjugated to a marker to detect the immune complexes;
   washing the support to remove non-immobilized antibodies and detection agent; and
   detecting the immune complexes on the array, to obtain an antibody profile.

19. The method of claim 18, wherein each of the proteins of the array is selected from Table 1 or Table 2.

20. The method of claim 18, further comprising correlating the antibody profile to a single individual in a population of from about 1 million individuals to about 100 billion individuals.

21. The method of claim 20, wherein correlating the antibody profile to a single individual in a population of from about 1 million individuals to about 100 billion individuals comprises correlating the antibody profile to the single individual in a population of about 10 million individuals.

22. The method of claim 20, wherein correlating the antibody profile to a single individual in a population of from about 1 million individuals to about 100 billion individuals comprises correlating the antibody profile to an individual among a population of about 10 billion individuals.

23. A method of analyzing biological material from each of the plurality of individuals, comprising:
   obtaining a plurality of samples of a biological material from each of the plurality of individuals, each of the plurality of samples having individual-specific antibodies;
   contacting the array of claim 1 with each of the plurality of samples to bind at least a portion of the individual-specific antibodies to the multiple proteins of the array, to form immune complexes;
   applying at least one detection agent to the array, the detection agent comprising at least one interacting protein conjugated to a marker to detect the immune complexes;
   washing the support to remove non-immobilized individual-specific antibodies and detection agent; and
   detecting the immune complexes on the array, to obtain an antibody profile.

24. The method of claim 23, further comprising comparing the antibody profile obtained from each of the plurality of individuals to determine a relationship.

* * * * *

SEQUENCE LISTING

<160> NUMBER OF SEQ ID NOS: 80

<210> SEQ ID NO 1
<211> LENGTH: 2768
<212> TYPE: PRT
<213> ORGANISM: Homo sapiens

<400> SEQUENCE: 1

```
Met Ala Leu Val Leu Glu Ile Phe Thr Leu Leu Ala Ser Ile Cys Trp
1               5                   10                  15

Val Ser Ala Asn Ile Phe Glu Tyr Gln Val Asp Ala Gln Pro Leu Arg
            20                  25                  30

Pro Cys Glu Leu Gln Arg Glu Thr Ala Phe Leu Lys Gln Ala Asp Tyr
        35                  40                  45

Val Pro Gln Cys Ala Glu Asp Gly Ser Phe Gln Thr Val Gln Cys Gln
    50                  55                  60

Asn Asp Gly Arg Ser Cys Trp Cys Val Gly Ala Asn Gly Ser Glu Val
65                  70                  75                  80

Leu Gly Ser Arg Gln Pro Gly Arg Pro Val Ala Cys Leu Ser Phe Cys
                85                  90                  95

Gln Leu Gln Lys Gln Gln Ile Leu Leu Ser Gly Tyr Ile Asn Ser Thr
            100                 105                 110

Asp Thr Ser Tyr Leu Pro Gln Cys Gln Asp Ser Gly Asp Tyr Ala Pro
        115                 120                 125

Val Gln Cys Asp Val Gln Gln Val Gln Cys Trp Cys Val Asp Ala Glu
    130                 135                 140

Gly Met Glu Val Tyr Gly Thr Arg Gln Leu Gly Arg Pro Lys Arg Cys
145                 150                 155                 160

Pro Arg Ser Cys Glu Ile Arg Asn Arg Arg Leu Leu His Gly Val Gly
                165                 170                 175

Asp Lys Ser Pro Pro Gln Cys Ser Ala Glu Gly Glu Phe Met Pro Val
        180                 185                 190

Gln Cys Lys Phe Val Asn Thr Thr Asp Met Met Ile Phe Asp Leu Val
    195                 200                 205

His Ser Tyr Asn Arg Phe Pro Asp Ala Phe Val Thr Phe Ser Ser Phe
    210                 215                 220

Gln Arg Arg Phe Pro Glu Val Ser Gly Tyr Cys His Cys Ala Asp Ser
225                 230                 235                 240

Gln Gly Arg Glu Leu Ala Glu Thr Gly Leu Glu Leu Leu Leu Asp Glu
                245                 250                 255

Ile Tyr Asp Thr Ile Phe Ala Gly Leu Asp Leu Pro Ser Thr Phe Thr
            260                 265                 270

Glu Thr Thr Leu Tyr Arg Ile Leu Gln Arg Arg Phe Leu Ala Val Gln
        275                 280                 285

Ser Val Ile Ser Gly Arg Phe Arg Cys Pro Thr Lys Cys Glu Val Glu
    290                 295                 300

Arg Phe Thr Ala Thr Ser Phe Gly His Pro Tyr Val Pro Ser Cys Arg
305                 310                 315                 320

Arg Asn Gly Asp Tyr Gln Ala Val Gln Cys Gln Thr Glu Gly Pro Cys
                325                 330                 335

Trp Cys Val Asp Ala Gln Gly Lys Glu Met His Gly Thr Arg Gln Gln
            340                 345                 350

Gly Glu Pro Pro Ser Cys Ala Glu Gly Gln Ser Cys Ala Ser Glu Arg
        355                 360                 365

Gln Gln Ala Leu Ser Arg Leu Tyr Phe Gly Thr Ser Gly Tyr Phe Ser
    370                 375                 380

Gln His Asp Leu Phe Ser Ser Pro Glu Lys Arg Trp Ala Ser Pro Arg
385                 390                 395                 400

Val Ala Arg Phe Ala Thr Ser Cys Pro Pro Thr Ile Lys Glu Leu Phe
                405                 410                 415
```

-continued

Val Asp Ser Gly Leu Leu Arg Pro Met Val Glu Gly Gln Ser Gln Gln
            420                 425                 430

Phe Ser Val Ser Glu Asn Leu Leu Lys Glu Ala Ile Arg Ala Ile Phe
        435                 440                 445

Pro Ser Arg Gly Leu Ala Arg Leu Ala Leu Gln Phe Thr Thr Asn Pro
    450                 455                 460

Lys Arg Leu Gln Gln Asn Leu Phe Gly Gly Lys Phe Leu Val Asn Val
465                 470                 475                 480

Gly Gln Phe Asn Leu Ser Gly Ala Leu Gly Thr Arg Gly Thr Phe Asn
                485                 490                 495

Phe Ser Gln Phe Gln Gln Leu Gly Leu Ala Ser Phe Leu Asn Gly
                    500                 505                 510

Gly Arg Gln Glu Asp Leu Ala Lys Pro Leu Ser Val Gly Leu Asp Ser
                515                 520                 525

Asn Ser Ser Thr Gly Thr Pro Glu Ala Ala Lys Lys Asp Gly Thr Met
    530                 535                 540

Asn Lys Pro Thr Val Gly Ser Phe Gly Phe Glu Ile Asn Leu Gln Glu
545                 550                 555                 560

Asn Gln Asn Ala Leu Lys Phe Leu Ala Ser Leu Leu Glu Leu Pro Glu
                565                 570                 575

Phe Leu Leu Phe Leu Gln His Ala Ile Ser Val Pro Glu Asp Val Ala
                580                 585                 590

Arg Asp Leu Gly Asp Val Met Glu Thr Val Leu Ser Ser Gln Thr Cys
            595                 600                 605

Glu Gln Thr Pro Glu Arg Leu Phe Val Pro Ser Cys Thr Thr Glu Gly
            610                 615                 620

Ser Tyr Glu Asp Val Gln Cys Phe Ser Gly Glu Cys Trp Cys Val Asn
625                 630                 635                 640

Ser Trp Gly Lys Glu Leu Pro Gly Ser Arg Val Arg Gly Gly Gln Pro
                645                 650                 655

Arg Cys Pro Thr Asp Cys Glu Lys Gln Arg Ala Arg Met Gln Ser Leu
                660                 665                 670

Met Gly Ser Gln Pro Ala Gly Ser Thr Leu Phe Val Pro Ala Cys Thr
        675                 680                 685

Ser Glu Gly His Phe Leu Pro Val Gln Cys Phe Asn Ser Glu Cys Tyr
    690                 695                 700

Cys Val Asp Ala Glu Gly Gln Ala Ile Pro Gly Thr Arg Ser Ala Ile
705                 710                 715                 720

Gly Lys Pro Lys Lys Cys Pro Thr Pro Cys Gln Leu Gln Ser Glu Gln
                725                 730                 735

Ala Phe Leu Arg Thr Val Gln Ala Leu Leu Ser Asn Ser Ser Met Leu
            740                 745                 750

Pro Thr Leu Ser Asp Thr Tyr Ile Pro Gln Cys Ser Thr Asp Gly Gln
        755                 760                 765

Trp Arg Gln Val Gln Cys Asn Gly Pro Pro Glu Gln Val Phe Glu Leu
    770                 775                 780

Tyr Gln Arg Trp Glu Ala Gln Asn Lys Gly Gln Asp Leu Thr Pro Ala
785                 790                 795                 800

Lys Leu Leu Val Lys Ile Met Ser Tyr Arg Glu Ala Ala Ser Gly Asn
                805                 810                 815

Phe Ser Leu Phe Ile Gln Ser Leu Tyr Glu Ala Gly Gln Gln Asp Val
            820                 825                 830

```
Phe Pro Val Leu Ser Gln Tyr Pro Ser Leu Gln Asp Val Pro Leu Ala
             835                 840                 845

Ala Leu Glu Gly Lys Arg Pro Gln Pro Arg Glu Asn Ile Leu Leu Glu
850                 855                 860

Pro Tyr Leu Phe Trp Gln Ile Leu Asn Gly Gln Leu Ser Gln Tyr Pro
865                 870                 875                 880

Gly Ser Tyr Ser Asp Phe Ser Thr Pro Leu Ala His Phe Asp Leu Arg
                 885                 890                 895

Asn Cys Trp Cys Val Asp Glu Ala Gly Gln Leu Glu Gly Met Arg
             900                 905                 910

Ser Glu Pro Ser Lys Leu Pro Thr Cys Pro Gly Ser Cys Glu Glu Ala
             915                 920                 925

Lys Leu Arg Val Leu Gln Phe Ile Arg Glu Thr Glu Glu Ile Val Ser
             930                 935                 940

Ala Ser Asn Ser Ser Arg Phe Pro Leu Gly Glu Ser Phe Leu Val Ala
945                 950                 955                 960

Lys Gly Ile Arg Leu Arg Asn Glu Asp Leu Gly Leu Pro Pro Leu Phe
                 965                 970                 975

Pro Pro Arg Glu Ala Phe Ala Glu Gln Phe Leu Arg Gly Ser Asp Tyr
                 980                 985                 990

Ala Ile Arg Leu Ala Ala Gln Ser  Thr Leu Ser Phe Tyr  Gln Arg Arg
                 995                1000                1005

Arg Phe  Ser Pro Asp Asp Ser  Ala Gly Ala Ser Ala  Leu Leu Arg
    1010                1015                1020

Ser Gly  Pro Tyr Met Pro Gln  Cys Asp Ala Phe Gly  Ser Trp Glu
    1025                1030                1035

Pro Val  Gln Cys His Ala Gly  Thr Gly His Cys Trp  Cys Val Asp
    1040                1045                1050

Glu Lys  Gly Gly Phe Ile Pro  Gly Ser Leu Thr Ala  Arg Ser Leu
    1055                1060                1065

Gln Ile  Pro Gln Cys Pro Thr  Thr Cys Glu Lys Ser  Arg Thr Ser
    1070                1075                1080

Gly Leu  Leu Ser Ser Trp Lys  Gln Ala Arg Ser Gln  Glu Asn Pro
    1085                1090                1095

Ser Pro  Lys Asp Leu Phe Val  Pro Ala Cys Leu Glu  Thr Gly Glu
    1100                1105                1110

Tyr Ala  Arg Leu Gln Ala Ser  Gly Ala Gly Thr Trp  Cys Val Asp
    1115                1120                1125

Pro Ala  Ser Gly Glu Glu Leu  Arg Pro Gly Ser Ser  Ser Ser Ala
    1130                1135                1140

Gln Cys  Pro Ser Leu Cys Asn  Val Leu Lys Ser Gly  Val Leu Ser
    1145                1150                1155

Arg Arg  Val Ser Pro Gly Tyr  Val Pro Ala Cys Arg  Ala Glu Asp
    1160                1165                1170

Gly Gly  Phe Ser Pro Val Gln  Cys Asp Gln Ala Gln  Gly Ser Cys
    1175                1180                1185

Trp Cys  Val Met Asp Ser Gly  Glu Glu Val Pro Gly  Thr Arg Val
    1190                1195                1200

Thr Gly  Gly Gln Pro Ala Cys  Glu Ser Pro Arg Cys  Pro Leu Pro
    1205                1210                1215

Phe Asn  Ala Ser Glu Val Val  Gly Gly Thr Ile Leu  Cys Glu Thr
    1220                1225                1230

Ile Ser  Gly Pro Thr Gly Ser  Ala Met Gln Gln Cys  Gln Leu Leu
```

-continued

```
          1235                1240                1245
Cys Arg Gln Gly Ser Trp Ser Val Phe Pro Pro Gly Pro Leu Ile
    1250                1255                1260
Cys Ser Leu Glu Ser Gly Arg Trp Glu Ser Gln Leu Pro Gln Pro
    1265                1270                1275
Arg Ala Cys Gln Arg Pro Gln Leu Trp Gln Thr Ile Gln Thr Gln
    1280                1285                1290
Gly His Phe Gln Leu Gln Leu Pro Pro Gly Lys Met Cys Ser Ala
    1295                1300                1305
Asp Tyr Ala Asp Leu Leu Gln Thr Phe Gln Val Phe Ile Leu Asp
    1310                1315                1320
Glu Leu Thr Ala Arg Gly Phe Cys Gln Ile Gln Val Lys Thr Phe
    1325                1330                1335
Gly Thr Leu Val Ser Ile Pro Val Cys Asn Asn Ser Ser Val Gln
    1340                1345                1350
Val Gly Cys Leu Thr Arg Glu Arg Leu Gly Val Asn Val Thr Trp
    1355                1360                1365
Lys Ser Arg Leu Glu Asp Ile Pro Val Ala Ser Leu Pro Asp Leu
    1370                1375                1380
His Asp Ile Glu Arg Ala Leu Val Gly Lys Asp Leu Leu Gly Arg
    1385                1390                1395
Phe Thr Asp Leu Ile Gln Ser Gly Ser Phe Gln Leu His Leu Asp
    1400                1405                1410
Ser Lys Thr Phe Pro Ala Glu Thr Ile Arg Phe Leu Gln Gly Asp
    1415                1420                1425
His Phe Gly Thr Ser Pro Arg Thr Trp Phe Gly Cys Ser Glu Gly
    1430                1435                1440
Phe Tyr Gln Val Leu Thr Ser Glu Ala Ser Gln Asp Gly Leu Gly
    1445                1450                1455
Cys Val Lys Cys Pro Glu Gly Ser Tyr Ser Gln Asp Glu Glu Cys
    1460                1465                1470
Ile Pro Cys Pro Val Gly Phe Tyr Gln Glu Gln Ala Gly Ser Leu
    1475                1480                1485
Ala Cys Val Pro Cys Pro Val Gly Arg Thr Thr Ile Ser Ala Gly
    1490                1495                1500
Ala Phe Ser Gln Thr His Cys Val Thr Asp Cys Gln Arg Asn Glu
    1505                1510                1515
Ala Gly Leu Gln Cys Asp Gln Asn Gly Gln Tyr Arg Ala Ser Gln
    1520                1525                1530
Lys Asp Arg Gly Ser Gly Lys Ala Phe Cys Val Asp Gly Glu Gly
    1535                1540                1545
Arg Arg Leu Pro Trp Trp Glu Thr Glu Ala Pro Leu Glu Asp Ser
    1550                1555                1560
Gln Cys Leu Met Met Gln Lys Phe Glu Lys Val Pro Glu Ser Lys
    1565                1570                1575
Val Ile Phe Asp Ala Asn Ala Pro Val Ala Val Arg Ser Lys Val
    1580                1585                1590
Pro Asp Ser Glu Phe Pro Val Met Gln Cys Leu Thr Asp Cys Thr
    1595                1600                1605
Glu Asp Glu Ala Cys Ser Phe Phe Thr Val Ser Thr Thr Glu Pro
    1610                1615                1620
Glu Ile Ser Cys Asp Phe Tyr Ala Trp Thr Ser Asp Asn Val Ala
    1625                1630                1635
```

```
Cys Met Thr Ser Asp Gln Lys Arg Asp Ala Leu Gly Asn Ser Lys
    1640                1645                1650

Ala Thr Ser Phe Gly Ser Leu Arg Cys Gln Val Lys Val Arg Ser
    1655                1660                1665

His Gly Gln Asp Ser Pro Ala Val Tyr Leu Lys Lys Gly Gln Gly
    1670                1675                1680

Ser Thr Thr Thr Leu Gln Lys Arg Phe Glu Pro Thr Gly Phe Gln
    1685                1690                1695

Asn Met Leu Ser Gly Leu Tyr Asn Pro Ile Val Phe Ser Ala Ser
    1700                1705                1710

Gly Ala Asn Leu Thr Asp Ala His Leu Phe Cys Leu Leu Ala Cys
    1715                1720                1725

Asp Arg Asp Leu Cys Cys Asp Gly Phe Val Leu Thr Gln Val Gln
    1730                1735                1740

Gly Gly Ala Ile Ile Cys Gly Leu Leu Ser Ser Pro Ser Val Leu
    1745                1750                1755

Leu Cys Asn Val Lys Asp Trp Met Asp Pro Ser Glu Ala Trp Ala
    1760                1765                1770

Asn Ala Thr Cys Pro Gly Val Thr Tyr Asp Gln Glu Ser His Gln
    1775                1780                1785

Val Ile Leu Arg Leu Gly Asp Gln Glu Phe Ile Lys Ser Leu Thr
    1790                1795                1800

Pro Leu Glu Gly Thr Gln Asp Thr Phe Thr Asn Phe Gln Gln Val
    1805                1810                1815

Tyr Leu Trp Lys Asp Ser Asp Met Gly Ser Arg Pro Glu Ser Met
    1820                1825                1830

Gly Cys Arg Lys Asp Thr Val Pro Arg Pro Ala Ser Pro Thr Glu
    1835                1840                1845

Ala Gly Leu Thr Thr Glu Leu Phe Ser Pro Val Asp Leu Asn Gln
    1850                1855                1860

Val Ile Val Asn Gly Asn Gln Ser Leu Ser Ser Gln Lys His Trp
    1865                1870                1875

Leu Phe Lys His Leu Phe Ser Ala Gln Gln Ala Asn Leu Trp Cys
    1880                1885                1890

Leu Ser Arg Cys Val Gln Glu His Ser Phe Cys Gln Leu Ala Glu
    1895                1900                1905

Ile Thr Glu Ser Ala Ser Leu Tyr Phe Thr Cys Thr Leu Tyr Pro
    1910                1915                1920

Glu Ala Gln Val Cys Asp Asp Ile Met Glu Ser Asn Ala Gln Gly
    1925                1930                1935

Cys Arg Leu Ile Leu Pro Gln Met Pro Lys Ala Leu Phe Arg Lys
    1940                1945                1950

Lys Val Ile Leu Glu Asp Lys Val Lys Asn Phe Tyr Thr Arg Leu
    1955                1960                1965

Pro Phe Gln Lys Leu Met Gly Ile Ser Ile Arg Asn Lys Val Pro
    1970                1975                1980

Met Ser Glu Lys Ser Ile Ser Asn Gly Phe Phe Glu Cys Glu Arg
    1985                1990                1995

Arg Cys Asp Ala Asp Pro Cys Cys Thr Gly Phe Gly Phe Leu Asn
    2000                2005                2010

Val Ser Gln Leu Lys Gly Gly Glu Val Thr Cys Leu Thr Leu Asn
    2015                2020                2025
```

```
Ser  Leu  Gly  Ile  Gln  Met  Cys  Ser  Glu  Glu  Asn  Gly  Gly  Ala  Trp
     2030                     2035                     2040

Arg  Ile  Leu  Asp  Cys  Gly  Ser  Pro  Asp  Ile  Glu  Val  His  Thr  Tyr
     2045                     2050                     2055

Pro  Phe  Gly  Trp  Tyr  Gln  Lys  Pro  Ile  Ala  Gln  Asn  Asn  Ala  Pro
     2060                     2065                     2070

Ser  Phe  Cys  Pro  Leu  Val  Val  Leu  Pro  Ser  Leu  Thr  Glu  Lys  Val
     2075                     2080                     2085

Ser  Leu  Asp  Ser  Trp  Gln  Ser  Leu  Ala  Leu  Ser  Ser  Val  Val  Val
     2090                     2095                     2100

Asp  Pro  Ser  Ile  Arg  His  Phe  Asp  Val  Ala  His  Val  Ser  Thr  Ala
     2105                     2110                     2115

Ala  Thr  Ser  Asn  Phe  Ser  Ala  Val  Arg  Asp  Leu  Cys  Leu  Ser  Glu
     2120                     2125                     2130

Cys  Ser  Gln  His  Glu  Ala  Cys  Leu  Ile  Thr  Thr  Leu  Gln  Thr  Gln
     2135                     2140                     2145

Pro  Gly  Ala  Val  Arg  Cys  Met  Phe  Tyr  Ala  Asp  Thr  Gln  Ser  Cys
     2150                     2155                     2160

Thr  His  Ser  Leu  Gln  Gly  Gln  Asn  Cys  Arg  Leu  Leu  Leu  Arg  Glu
     2165                     2170                     2175

Glu  Ala  Thr  His  Ile  Tyr  Arg  Lys  Pro  Gly  Ile  Ser  Leu  Leu  Ser
     2180                     2185                     2190

Tyr  Glu  Ala  Ser  Val  Pro  Ser  Val  Pro  Ile  Ser  Thr  His  Gly  Arg
     2195                     2200                     2205

Leu  Leu  Gly  Arg  Ser  Gln  Ala  Ile  Gln  Val  Gly  Thr  Ser  Trp  Lys
     2210                     2215                     2220

Gln  Val  Asp  Gln  Phe  Leu  Gly  Val  Pro  Tyr  Ala  Ala  Pro  Pro  Leu
     2225                     2230                     2235

Ala  Glu  Arg  Arg  Phe  Gln  Ala  Pro  Glu  Pro  Leu  Asn  Trp  Thr  Gly
     2240                     2245                     2250

Ser  Trp  Asp  Ala  Ser  Lys  Pro  Arg  Ala  Ser  Cys  Trp  Gln  Pro  Gly
     2255                     2260                     2265

Thr  Arg  Thr  Ser  Thr  Ser  Pro  Gly  Val  Ser  Glu  Asp  Cys  Leu  Tyr
     2270                     2275                     2280

Leu  Asn  Val  Phe  Ile  Pro  Gln  Asn  Val  Ala  Pro  Asn  Ala  Ser  Val
     2285                     2290                     2295

Leu  Val  Phe  Phe  His  Asn  Thr  Met  Asp  Arg  Glu  Glu  Ser  Glu  Gly
     2300                     2305                     2310

Trp  Pro  Ala  Ile  Asp  Gly  Ser  Phe  Leu  Ala  Ala  Val  Gly  Asn  Leu
     2315                     2320                     2325

Ile  Val  Val  Thr  Ala  Ser  Tyr  Arg  Val  Gly  Val  Phe  Gly  Phe  Leu
     2330                     2335                     2340

Ser  Ser  Gly  Ser  Gly  Glu  Val  Ser  Gly  Asn  Trp  Gly  Leu  Leu  Asp
     2345                     2350                     2355

Gln  Val  Ala  Ala  Leu  Thr  Trp  Val  Gln  Thr  His  Ile  Arg  Gly  Phe
     2360                     2365                     2370

Gly  Gly  Asp  Pro  Arg  Arg  Val  Ser  Leu  Ala  Ala  Asp  Arg  Gly  Gly
     2375                     2380                     2385

Ala  Asp  Val  Ala  Ser  Ile  His  Leu  Leu  Thr  Ala  Arg  Ala  Thr  Asn
     2390                     2395                     2400

Ser  Gln  Leu  Phe  Arg  Arg  Ala  Val  Leu  Met  Gly  Gly  Ser  Ala  Leu
     2405                     2410                     2415

Ser  Pro  Ala  Ala  Val  Ile  Ser  His  Glu  Arg  Ala  Gln  Gln  Gln  Ala
```

```
            2420                2425                2430
Ile Ala Leu Ala Lys Glu Val Ser Cys Pro Met Ser Ser Ser Gln
    2435                2440                2445

Glu Val Val Ser Cys Leu Arg Gln Lys Pro Ala Asn Val Leu Asn
    2450                2455                2460

Asp Ala Gln Thr Lys Leu Leu Ala Val Ser Gly Pro Phe His Tyr
    2465                2470                2475

Trp Gly Pro Val Ile Asp Gly His Phe Leu Arg Glu Pro Pro Ala
    2480                2485                2490

Arg Ala Leu Lys Arg Ser Leu Trp Val Glu Val Asp Leu Leu Ile
    2495                2500                2505

Gly Ser Ser Gln Asp Asp Gly Leu Ile Asn Arg Ala Lys Ala Val
    2510                2515                2520

Lys Gln Phe Glu Glu Ser Arg Gly Arg Thr Ser Ser Lys Thr Ala
    2525                2530                2535

Phe Tyr Gln Ala Leu Gln Asn Ser Leu Gly Gly Glu Asp Ser Asp
    2540                2545                2550

Ala Arg Val Glu Ala Ala Thr Trp Tyr Tyr Ser Leu Glu His
    2555                2560                2565

Ser Thr Asp Asp Tyr Ala Ser Phe Ser Arg Ala Leu Glu Asn Ala
    2570                2575                2580

Thr Arg Asp Tyr Phe Ile Ile Cys Pro Ile Ile Asp Met Ala Ser
    2585                2590                2595

Ala Trp Ala Lys Arg Ala Arg Gly Asn Val Phe Met Tyr His Ala
    2600                2605                2610

Pro Glu Asn Tyr Gly His Gly Ser Leu Glu Leu Leu Ala Asp Val
    2615                2620                2625

Gln Phe Ala Leu Gly Leu Pro Phe Tyr Pro Ala Tyr Glu Gly Gln
    2630                2635                2640

Phe Ser Leu Glu Glu Lys Ser Leu Ser Leu Lys Ile Met Gln Tyr
    2645                2650                2655

Phe Ser His Phe Ile Arg Ser Gly Asn Pro Asn Tyr Pro Tyr Glu
    2660                2665                2670

Phe Ser Arg Lys Val Pro Thr Phe Ala Thr Pro Trp Pro Asp Phe
    2675                2680                2685

Val Pro Arg Ala Gly Gly Glu Asn Tyr Lys Glu Phe Ser Glu Leu
    2690                2695                2700

Leu Pro Asn Arg Gln Gly Leu Lys Lys Ala Asp Cys Ser Phe Trp
    2705                2710                2715

Ser Lys Tyr Ile Ser Ser Leu Lys Thr Ser Ala Asp Gly Ala Lys
    2720                2725                2730

Gly Gly Gln Ser Ala Glu Ser Glu Glu Glu Leu Thr Ala Gly
    2735                2740                2745

Ser Gly Leu Arg Glu Asp Leu Leu Ser Leu Gln Glu Pro Gly Ser
    2750                2755                2760

Lys Thr Tyr Ser Lys
    2765

<210> SEQ ID NO 2
<211> LENGTH: 447
<212> TYPE: PRT
<213> ORGANISM: Homo sapiens

<400> SEQUENCE: 2
```

-continued

```
Met Ser Asn Asn Gly Leu Asp Ile Gln Asp Lys Pro Ala Pro Pro
1               5                   10                  15

Met Arg Asn Thr Ser Thr Met Ile Gly Ala Gly Ser Lys Asp Ala Gly
                20                  25                  30

Thr Leu Asn His Gly Ser Lys Pro Leu Pro Asn Pro Glu Glu Lys
                35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                    85                  90                  95

Thr Gly Met Pro Glu Gln Trp Ala Arg Leu Leu Gln Thr Ser Asn Ile
                100                 105                 110

Thr Lys Ser Glu Gln Lys Lys Asn Pro Gln Ala Val Leu Asp Val Leu
                115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Val Ser Glu Asp
                165                 170                 175

Glu Asp Asp Asp Asp Asp Ala Thr Pro Pro Val Ile Ala Pro
                180                 185                 190

Arg Pro Glu His Thr Lys Ser Val Tyr Thr Arg Ser Val Ile Glu Pro
                195                 200                 205

Leu Pro Val Thr Pro Thr Arg Asp Val Ala Thr Ser Pro Ile Ser Pro
    210                 215                 220

Thr Glu Asn Asn Thr Thr Pro Pro Asp Ala Leu Thr Arg Asn Thr Glu
225                 230                 235                 240

Lys Gln Lys Lys Lys Pro Lys Met Ser Asp Glu Glu Ile Leu Glu Lys
                245                 250                 255

Leu Arg Ser Ile Val Ser Val Gly Asp Pro Lys Lys Lys Tyr Thr Arg
                260                 265                 270

Phe Glu Lys Ile Gly Gln Gly Ala Ser Gly Thr Val Tyr Thr Ala Met
    275                 280                 285

Asp Val Ala Thr Gly Gln Glu Val Ala Ile Lys Gln Met Asn Leu Gln
                290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
                340                 345                 350

Thr Asp Val Val Thr Glu Thr Cys Met Asp Gly Gln Ile Ala Ala
                355                 360                 365

Val Cys Arg Glu Cys Leu Gln Ala Leu Glu Phe Leu His Ser Asn Gln
    370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
```

```
                    420                 425                 430
Pro Glu Val Val Thr Arg Lys Ala Tyr Gly Pro Lys Val Asp Ile
    435                 440                 445

<210> SEQ ID NO 3
<211> LENGTH: 354
<212> TYPE: PRT
<213> ORGANISM: Homo sapiens

<400> SEQUENCE: 3

Met Cys Gly Arg Thr Ser Cys His Leu Pro Arg Asp Val Leu Thr Arg
1               5                   10                  15

Ala Cys Ala Tyr Gln Asp Arg Gly Gln Gln Arg Leu Pro Glu Trp
            20                  25                  30

Arg Asp Pro Asp Lys Tyr Cys Pro Ser Tyr Asn Lys Ser Pro Gln Ser
        35                  40                  45

Asn Ser Pro Val Leu Leu Ser Arg Leu His Phe Glu Lys Asp Ala Asp
    50                  55                  60

Ser Ser Glu Arg Ile Ile Ala Pro Met Arg Trp Gly Leu Val Pro Ser
65                  70                  75                  80

Trp Phe Lys Glu Ser Asp Pro Ser Lys Leu Gln Phe Asn Thr Thr Asn
                85                  90                  95

Cys Arg Ser Asp Thr Val Met Glu Lys Arg Ser Phe Lys Val Pro Leu
            100                 105                 110

Gly Lys Gly Arg Arg Cys Val Val Leu Ala Asp Gly Phe Tyr Glu Trp
        115                 120                 125

Gln Arg Cys Gln Gly Thr Asn Gln Arg Gln Pro Tyr Phe Ile Tyr Phe
    130                 135                 140

Pro Gln Ile Lys Thr Glu Lys Ser Gly Ser Ile Gly Ala Ala Asp Ser
145                 150                 155                 160

Pro Glu Asn Trp Glu Lys Val Trp Asp Asn Trp Arg Leu Leu Thr Met
                165                 170                 175

Ala Gly Ile Phe Asp Cys Trp Glu Pro Pro Glu Gly Gly Asp Val Leu
            180                 185                 190

Tyr Ser Tyr Thr Ile Ile Thr Val Asp Ser Cys Lys Gly Leu Ser Asp
        195                 200                 205

Ile His His Arg Met Pro Ala Ile Leu Asp Gly Glu Glu Ala Val Ser
    210                 215                 220

Lys Trp Leu Asp Phe Gly Glu Val Ser Thr Gln Glu Ala Leu Lys Leu
225                 230                 235                 240

Ile His Pro Thr Glu Asn Ile Thr Phe His Ala Val Ser Ser Val Val
                245                 250                 255

Asn Asn Ser Arg Asn Asn Thr Pro Glu Cys Leu Ala Pro Val Asp Leu
            260                 265                 270

Val Val Lys Lys Glu Leu Arg Ala Ser Gly Ser Ser Gln Arg Met Leu
        275                 280                 285

Gln Trp Leu Ala Thr Lys Ser Pro Lys Lys Glu Asp Ser Lys Thr Pro
    290                 295                 300

Gln Lys Glu Glu Ser Asp Val Pro Gln Trp Ser Ser Gln Phe Leu Gln
305                 310                 315                 320

Lys Ser Pro Leu Pro Thr Lys Arg Gly Thr Ala Gly Leu Leu Glu Gln
                325                 330                 335

Trp Leu Lys Arg Glu Lys Glu Glu Pro Val Ala Lys Arg Pro Tyr
            340                 345                 350
```

Ser Gln

<210> SEQ ID NO 4
<211> LENGTH: 505
<212> TYPE: PRT
<213> ORGANISM: Homo sapiens

<400> SEQUENCE: 4

```
Met Ser Asp Lys Asp Asp Ile Glu Thr Pro Leu Leu Thr Glu Ala Ala
1               5                   10                  15

Pro Ile Leu Glu Asp Gly Asn Cys Glu Pro Ala Lys Asn Ser Glu Ser
            20                  25                  30

Val Asp Gln Gly Ala Lys Pro Glu Ser Lys Ser Glu Pro Val Val Ser
        35                  40                  45

Thr Arg Lys Arg Pro Glu Thr Lys Pro Ser Ser Asp Leu Glu Thr Ser
    50                  55                  60

Lys Val Leu Pro Ile Gln Asp Asn Val Ser Lys Asp Val Pro Gln Thr
65                  70                  75                  80

Arg Trp Gly Tyr Trp Gly Ser Trp Gly Lys Ser Ile Leu Ser Ser Ala
                85                  90                  95

Ser Ala Thr Val Ala Thr Val Gly Gln Gly Ile Ser Asn Val Ile Glu
            100                 105                 110

Lys Ala Glu Thr Ser Leu Gly Ile Pro Ser Pro Ser Glu Ile Ser Thr
        115                 120                 125

Glu Val Lys Tyr Val Ala Gly Glu Thr Asn Ala Lys Glu Asn Glu Asn
    130                 135                 140

Ser Ser Pro Val Ala Gly Ala Phe Gly Val Phe Ser Thr Ile Ser Thr
145                 150                 155                 160

Ala Val Gln Ser Thr Gly Lys Ser Val Ile Ser Gly Gly Leu Asp Ala
                165                 170                 175

Leu Glu Phe Ile Gly Lys Lys Thr Met Asp Val Ile Ala Glu Gly Asp
            180                 185                 190

Pro Gly Phe Lys Arg Thr Lys Gly Leu Met Asn Arg Asn Ala Thr Leu
        195                 200                 205

Ser Gln Val Leu Arg Glu Ala Lys Glu Lys Glu Ile Arg Thr Ser
    210                 215                 220

Asn Glu Val Thr Val Glu Thr Asp Lys Lys Thr His Tyr Gly Leu Leu
225                 230                 235                 240

Phe Asp Glu Phe Gln Gly Leu Ser His Leu Glu Ala Leu Glu Met Leu
                245                 250                 255

Ser Gln Glu Ser Glu Ile Lys Val Lys Ser Ile Leu Asn Ser Leu Ser
            260                 265                 270

Gly Glu Glu Leu Glu Thr Leu Lys Val Glu Leu Glu Gln Leu Lys Glu
        275                 280                 285

Thr Phe Ser Leu Ala Glu Phe Cys Glu Glu Glu Glu Glu Lys Lys
    290                 295                 300

Gly Asp Glu Asp Phe Thr Lys Asp Ile Thr Glu Leu Phe Ser Gln Leu
305                 310                 315                 320

His Val Ser Ser Lys Pro Glu Lys Leu Ala Arg Ala Arg Asn Thr Ala
                325                 330                 335

His Glu Trp Ile Arg Lys Ser Leu Thr Lys Pro Leu Ala Glu Asn Glu
            340                 345                 350

Glu Gly Glu Lys Gln Ser Glu Ala Glu Asn Thr Glu Gln Val Asn Lys
        355                 360                 365
```

```
Asn Ser Ile Glu Asp Ile His Ala Phe Ala Ile Arg Ser Leu Ala Glu
    370                 375                 380
Leu Thr Ala Cys Ser Ile Glu Leu Phe His Lys Thr Ala Ala Leu Val
385                 390                 395                 400
Leu His Gly Arg Lys Gln Glu Val Thr Ala Ile Glu Arg Ser Gln Thr
                405                 410                 415
Leu Ser Gln Met Thr Ile Val Leu Cys Lys Glu Leu Ser Ser Leu Ser
            420                 425                 430
Lys Glu Phe Thr Thr Cys Leu Thr Ala Gly Val Lys Glu Met Ala
                435                 440                 445
Asp Val Leu Asn Pro Leu Ile Thr Ala Val Phe Leu Glu Ala Ser Asn
450                 455                 460
Ser Ala Ser Tyr Ile Gln Asp Ala Phe Gln Leu Leu Pro Val Leu
465                 470                 475                 480
Glu Ile Ser Leu Ile Glu Asn Lys Ile Glu Ser His Arg His Glu Leu
                485                 490                 495
Gln Gly Gln Lys Pro Leu Leu Glu His
                500                 505

<210> SEQ ID NO 5
<211> LENGTH: 546
<212> TYPE: PRT
<213> ORGANISM: Homo sapiens

<400> SEQUENCE: 5

Asp Arg Gly Ser Gly Ala Phe Ser Leu Glu Thr Ile Ala Glu Ser Ser
1               5                   10                  15
Ala Gln Ser Pro Gly Cys Gln Leu Leu Val Glu Thr Leu Gly Val Pro
                20                  25                  30
Leu Gln Glu Ala Thr Glu Leu Gly Asp Pro Thr Gln Ala Asp Ser Ala
            35                  40                  45
Arg Pro Glu Gln Ser Ser Gln Ser Pro Val Gln Ala Val Pro Gly Ser
        50                  55                  60
Gly Asp Ser Gln Pro Asp Asp Pro Asp Arg Gly Thr Gly Leu Ser
65                  70                  75                  80
Ala Ser Gln Arg Ala Ser Gln Asp His Leu Ser Glu Gln Gly Ala Asp
                85                  90                  95
Asp Ser Lys Pro Glu Thr Asp Arg Val Pro Gly Asp Gly Gln Lys
                100                 105                 110
Glu His Leu Pro Ser Ile Asp Ser Glu Gly Glu Lys Pro Asp Arg Gly
            115                 120                 125
Ala Pro Gln Glu Gly Gly Ala Gln Arg Thr Ala Gly Ala Gly Leu Pro
        130                 135                 140
Arg Gly Pro Gln Glu Gly Asp Gly Val Pro Cys Thr Pro Ala Ser
145                 150                 155                 160
Ala Pro Thr Ser Gly Pro Ala Pro Gly Leu Gly Pro Ala Ser Trp Cys
                165                 170                 175
Leu Glu Pro Gly Ser Val Ala Gln Gly Ser Pro Asp Pro Gln Gln Thr
            180                 185                 190
Pro Ser Arg Met Gly Arg Glu Gly Glu Gly Thr His Ser Ser Leu Gly
        195                 200                 205
Cys Ser Ser Leu Gly Met Val Val Ile Ala Asp Leu Ser Thr Asp Pro
210                 215                 220
Thr Glu Leu Glu Glu Arg Ala Leu Glu Val Ala Gly Pro Asp Gly Gln
225                 230                 235                 240
```

```
Ala Ser Ala Ile Ser Pro Ala Ser Pro Arg Arg Lys Ala Ala Asp Gly
            245                 250                 255

Gly His Arg Arg Ala Leu Pro Gly Cys Thr Ser Leu Thr Gly Glu Thr
        260                 265                 270

Thr Gly Glu Ser Gly Glu Ala Gly Gln Asp Gly Lys Pro Pro Gly Asp
    275                 280                 285

Val Leu Val Gly Pro Thr Ala Ser Leu Ala Leu Ala Pro Gly Ser Gly
        290                 295                 300

Glu Ser Met Met Gly Ala Gly Asp Ser Gly His Ala Ser Pro Asp Thr
305                 310                 315                 320

Gly Pro Cys Val Asn Gln Lys Gln Glu Pro Gly Pro Ala Gln Glu Glu
                325                 330                 335

Ala Glu Leu Gly Gly Gln Asn Leu Glu Arg Asp Leu Glu Gly Phe Arg
            340                 345                 350

Val Ser Pro Gln Ala Ser Val Val Leu Glu His Arg Glu Ile Ala Asp
        355                 360                 365

Asp Pro Leu Gln Glu Pro Gly Ala Gln Arg Gly Ile Pro Asp Thr Thr
    370                 375                 380

Ser Glu Leu Ala Gly Gln Arg Asp His Leu Pro His Ser Ala Asp Gln
385                 390                 395                 400

Gly Thr Trp Ala Asp Ser Leu Ala Val Glu Leu Asp Phe Leu Leu Asp
                405                 410                 415

Ser Gln Ile Gln Asp Ala Leu Asp Ala Ser Asp Phe Glu Ala Pro Pro
            420                 425                 430

Glu Gln Leu Phe Pro Ser Gly Asn Lys Pro Gly Pro Cys Trp Pro Gly
        435                 440                 445

Pro Ser Ser His Ala Asn Gly Asp Pro Val Ala Val Ala Lys Ala Gln
    450                 455                 460

Pro Arg Thr Phe Val Gly Ile Gln Ala Ser Glu Ala Ser Arg Met Glu
465                 470                 475                 480

Asp Ala Thr Asn Val Val Arg Gly Leu Ile Val Glu Leu Ser Asn Leu
                485                 490                 495

Asn Arg Leu Ile Met Gly Thr His Arg Asp Leu Glu Ala Phe Lys Arg
            500                 505                 510

Leu Asn Tyr Arg Lys Thr Lys Leu Gly Gly Lys Ala Pro Leu Pro Tyr
        515                 520                 525

Pro Ser Lys Gly Pro Gly Asn Ile Pro Arg Gly Asp Pro Pro Trp Arg
    530                 535                 540

Glu Leu
545

<210> SEQ ID NO 6
<211> LENGTH: 204
<212> TYPE: PRT
<213> ORGANISM: Homo sapiens

<400> SEQUENCE: 6

Met Glu Pro Lys Ala Ser Cys Pro Ala Ala Pro Leu Met Glu Arg
1               5                   10                  15

Lys Phe His Val Leu Gly Val Thr Gly Ser Val Ala Ala Leu Lys
            20                  25                  30

Leu Pro Leu Leu Val Ser Lys Leu Leu Asp Ile Pro Gly Leu Glu Val
        35                  40                  45

Ala Val Val Thr Thr Glu Arg Ala Lys His Phe Tyr Ser Pro Gln Asp
```

```
              50                  55                  60
Ile Pro Val Thr Leu Tyr Ser Asp Ala Asp Glu Trp Glu Met Trp Lys
 65                  70                  75                  80

Ser Arg Ser Asp Pro Val Leu His Ile Asp Leu Arg Arg Trp Ala Asp
                 85                  90                  95

Leu Leu Leu Val Ala Pro Leu Asp Ala Asn Thr Leu Gly Lys Val Ala
            100                 105                 110

Ser Gly Ile Cys Asp Asn Leu Leu Thr Cys Val Met Arg Ala Trp Asp
            115                 120                 125

Arg Ser Lys Pro Leu Leu Phe Cys Pro Ala Met Asn Thr Ala Met Trp
        130                 135                 140

Glu His Pro Ile Thr Ala Gln Gln Val Asp Gln Leu Lys Ala Phe Gly
145                 150                 155                 160

Tyr Val Glu Ile Pro Cys Val Ala Lys Lys Leu Val Cys Gly Asp Glu
                165                 170                 175

Gly Leu Gly Ala Met Ala Glu Val Gly Thr Ile Val Asp Lys Val Lys
            180                 185                 190

Glu Val Leu Phe Gln His Ser Gly Phe Gln Gln Ser
        195                 200

<210> SEQ ID NO 7
<211> LENGTH: 510
<212> TYPE: PRT
<213> ORGANISM: Homo sapiens

<400> SEQUENCE: 7

Met Asp Glu Lys Thr Lys Lys Ala Glu Glu Met Ala Leu Ser Leu Thr
 1               5                  10                  15

Arg Ala Val Ala Gly Gly Asp Glu Gln Val Ala Met Lys Cys Ala Ile
             20                  25                  30

Trp Leu Ala Glu Gln Arg Val Pro Leu Ser Val Gln Leu Lys Pro Glu
         35                  40                  45

Val Ser Pro Thr Gln Asp Ile Arg Leu Trp Val Ser Val Glu Asp Ala
 50                  55                  60

Gln Met His Thr Val Thr Ile Trp Leu Thr Val Arg Pro Asp Met Thr
 65                  70                  75                  80

Val Ala Ser Leu Lys Asp Met Val Phe Leu Asp Tyr Gly Phe Pro Pro
                 85                  90                  95

Val Leu Gln Gln Trp Val Ile Gly Gln Arg Leu Ala Arg Asp Gln Glu
            100                 105                 110

Thr Leu His Ser His Gly Val Arg Gln Asn Gly Asp Ser Ala Tyr Leu
            115                 120                 125

Tyr Leu Leu Ser Ala Arg Asn Thr Ser Leu Asn Pro Gln Glu Leu Gln
        130                 135                 140

Arg Glu Arg Gln Leu Arg Met Leu Glu Asp Leu Gly Phe Lys Asp Leu
145                 150                 155                 160

Thr Leu Gln Pro Arg Gly Pro Leu Glu Pro Gly Pro Pro Lys Pro Gly
                165                 170                 175

Val Pro Gln Glu Pro Gly Arg Gly Gln Pro Asp Ala Val Pro Glu Pro
            180                 185                 190

Pro Pro Val Gly Trp Gln Cys Pro Gly Cys Thr Phe Ile Asn Lys Pro
            195                 200                 205

Thr Arg Pro Gly Cys Glu Met Cys Cys Arg Ala Arg Pro Glu Ala Tyr
        210                 215                 220
```

```
Gln Val Pro Ala Ser Tyr Gln Pro Asp Glu Glu Arg Ala Arg Leu
225                 230                 235                 240

Ala Gly Glu Glu Glu Ala Leu Arg Gln Tyr Gln Gln Arg Lys Gln Gln
                245                 250                 255

Gln Gln Glu Gly Asn Tyr Leu Gln His Val Gln Leu Asp Gln Arg Ser
            260                 265                 270

Leu Val Leu Asn Thr Glu Pro Ala Glu Cys Pro Val Cys Tyr Ser Val
        275                 280                 285

Leu Ala Pro Gly Glu Ala Val Leu Arg Glu Cys Leu His Thr Phe
290                 295                 300

Cys Arg Glu Cys Leu Gln Gly Thr Ile Arg Asn Ser Gln Glu Ala Glu
305                 310                 315                 320

Val Ser Cys Pro Phe Ile Asp Asn Thr Tyr Ser Cys Ser Gly Lys Leu
                325                 330                 335

Leu Glu Arg Glu Ile Lys Ala Leu Leu Thr Pro Glu Asp Tyr Gln Arg
            340                 345                 350

Phe Leu Asp Leu Gly Ile Ser Ile Ala Glu Asn Arg Ser Ala Phe Ser
        355                 360                 365

Tyr His Cys Lys Thr Pro Asp Cys Lys Gly Trp Cys Phe Phe Glu Asp
370                 375                 380

Asp Val Asn Glu Phe Thr Cys Pro Val Cys Phe His Val Asn Cys Leu
385                 390                 395                 400

Leu Cys Lys Ala Ile His Glu Gln Met Asn Cys Lys Glu Tyr Gln Glu
                405                 410                 415

Asp Leu Ala Leu Arg Ala Gln Asn Asp Val Ala Ala Arg Gln Thr Thr
            420                 425                 430

Glu Met Leu Lys Val Met Leu Gln Gln Gly Glu Ala Met Arg Cys Pro
        435                 440                 445

Gln Cys Gln Ile Val Val Gln Lys Lys Asp Gly Cys Asp Trp Ile Arg
    450                 455                 460

Cys Thr Val Cys His Thr Glu Ile Cys Trp Val Thr Lys Gly Pro Arg
465                 470                 475                 480

Trp Gly Pro Gly Gly Pro Gly Asp Thr Ser Gly Gly Cys Arg Cys Arg
                485                 490                 495

Val Asn Gly Ile Pro Cys His Pro Ser Cys Gln Asn Cys His
            500                 505                 510

<210> SEQ ID NO 8
<211> LENGTH: 583
<212> TYPE: PRT
<213> ORGANISM: Homo sapiens

<400> SEQUENCE: 8

Met Ala Leu Lys Lys Ser Ser Pro Ser Leu Asp Ser Gly Asp Ser Asp
1               5                   10                  15

Ser Glu Glu Leu Pro Thr Phe Ala Phe Leu Lys Lys Glu Pro Ser Ser
            20                  25                  30

Thr Lys Arg Arg Gln Pro Glu Arg Glu Glu Lys Ile Val Val Val Asp
        35                  40                  45

Ile Ser Asp Cys Glu Ala Ser Cys Pro Ala Pro Glu Leu Phe Ser
    50                  55                  60

Pro Pro Val Pro Asp Ile Ala Glu Thr Val Thr Gln Thr Gln Pro Val
65                  70                  75                  80

Arg Leu Leu Ser Ser Glu Ser Glu Asp Glu Glu Glu Phe Ile Pro Leu
                85                  90                  95
```

-continued

Ala Gln Arg Leu Thr Cys Lys Phe Leu Thr His Lys Gln Leu Ser Pro
            100                 105                 110

Glu Asp Ser Ser Pro Val Lys Ser Val Leu Asp His Gln Asn Asn
            115                 120                 125

Glu Gly Ala Ser Cys Asp Trp Lys Lys Pro Phe Pro Lys Ile Pro Glu
130                 135                 140

Val Pro Leu His Asp Thr Pro Glu Arg Ser Ala Ala Asp Asn Lys Asp
145                 150                 155                 160

Leu Ile Leu Asp Pro Cys Cys Gln Leu Pro Ala Tyr Leu Ser Thr Cys
                165                 170                 175

Pro Gly Gln Ser Ser Ser Leu Ala Val Thr Lys Thr Asn Ser Asp Ile
            180                 185                 190

Leu Pro Pro Gln Lys Lys Thr Lys Pro Ser Gln Lys Val Gln Gly Arg
            195                 200                 205

Gly Ser His Gly Cys Arg Gln Gln Arg Gln Ala Arg Gln Lys Glu Ser
210                 215                 220

Thr Leu Arg Arg Gln Glu Arg Lys Asn Ala Ala Leu Val Thr Arg Met
225                 230                 235                 240

Lys Ala Gln Arg Pro Glu Glu Cys Leu Lys His Ile Ile Val Val Leu
                245                 250                 255

Asp Pro Val Leu Leu Gln Met Glu Gly Gly Gln Leu Leu Gly Ala
            260                 265                 270

Leu Gln Thr Met Glu Cys Arg Cys Val Ile Glu Ala Gln Ala Val Pro
            275                 280                 285

Cys Ser Val Thr Trp Arg Arg Arg Ala Gly Pro Ser Glu Asp Arg Glu
290                 295                 300

Asp Trp Val Glu Glu Pro Thr Val Leu Val Leu Arg Ala Glu Ala
305                 310                 315                 320

Phe Val Ser Met Ile Asp Asn Gly Lys Gln Gly Ser Leu Asp Ser Thr
                325                 330                 335

Met Lys Gly Lys Glu Thr Leu Gln Gly Phe Val Thr Asp Ile Thr Ala
            340                 345                 350

Lys Thr Ala Gly Lys Ala Leu Ser Leu Val Ile Val Asp Gln Glu Lys
            355                 360                 365

Cys Phe Ser Leu Glu Leu Leu Phe Phe Asp Phe Leu Pro Cys Thr Ser
370                 375                 380

Ala Gln Asn Pro Pro Arg Arg Gly Lys Gln Gly Ala Asn Lys Gln Thr
385                 390                 395                 400

Lys Lys Gln Gln Gln Arg Gln Pro Glu Ala Ser Ile Gly Ser Met Val
                405                 410                 415

Ser Arg Val Asp Ala Glu Glu Ala Leu Val Asp Leu Gln Leu His Thr
            420                 425                 430

Glu Ala Gln Ala Gln Ile Val Gln Ser Trp Lys Glu Leu Ala Asp Phe
            435                 440                 445

Thr Cys Ala Phe Thr Lys Ala Val Ala Glu Ala Pro Phe Lys Lys Leu
            450                 455                 460

Arg Asp Glu Thr Thr Phe Ser Phe Cys Leu Glu Ser Asp Trp Ala Gly
465                 470                 475                 480

Gly Val Lys Val Asp Leu Ala Gly Arg Gly Leu Ala Leu Val Trp Arg
                485                 490                 495

Arg Gln Ile Gln Gln Leu Asn Arg Val Ser Leu Glu Met Ala Ser Ala
            500                 505                 510

```
Val Val Asn Ala Tyr Pro Ser Pro Gln Leu Leu Val Gln Ala Tyr Gln
            515                 520                 525

Gln Cys Phe Ser Asp Lys Glu Arg Gln Asn Leu Leu Ala Asp Ile Gln
        530                 535                 540

Val Arg Arg Gly Glu Gly Val Thr Ser Thr Ser Arg Arg Ile Gly Pro
545                 550                 555                 560

Glu Leu Ser Arg Arg Ile Tyr Leu Gln Met Thr Thr Leu Gln Pro His
                565                 570                 575

Leu Ser Leu Asp Ser Ala Asp
            580

<210> SEQ ID NO 9
<211> LENGTH: 158
<212> TYPE: PRT
<213> ORGANISM: Homo sapiens

<400> SEQUENCE: 9

Met Ala Ala Gln Gly Val Gly Pro Gly Ser Ala Ala Pro Pro
1               5                   10                  15

Gly Leu Glu Ala Ala Arg Gln Lys Leu Ala Leu Arg Arg Lys Lys Val
            20                  25                  30

Leu Ser Thr Glu Glu Met Glu Leu Tyr Glu Leu Ala Gln Ala Ala Gly
        35                  40                  45

Gly Gly Ile Asp Pro Asp Val Phe Lys Ile Leu Val Asp Leu Leu Lys
    50                  55                  60

Leu Asn Val Ala Pro Leu Ala Val Phe Gln Met Leu Lys Ser Met Cys
65                  70                  75                  80

Ala Gly Gln Arg Leu Ala Ser Glu Pro Gln Asp Pro Ala Ala Val Ser
                85                  90                  95

Leu Pro Thr Ser Ser Val Pro Glu Thr Arg Gly Arg Asp Lys Gly Ser
            100                 105                 110

Ala Ala Leu Gly Gly Val Leu Ala Leu Ala Glu Arg Ser Asn His Glu
        115                 120                 125

Gly Ser Ser Gln Arg Met Pro Arg Gln Pro Ser Ala Thr Arg Leu Pro
    130                 135                 140

Lys Gly Gly Gly Pro Gly Lys Ser Pro Thr Gln Gly Ser Thr
145                 150                 155

<210> SEQ ID NO 10
<211> LENGTH: 209
<212> TYPE: PRT
<213> ORGANISM: Homo sapiens

<400> SEQUENCE: 10

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95
```

```
Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
            195                 200                 205

Ser

<210> SEQ ID NO 11
<211> LENGTH: 235
<212> TYPE: PRT
<213> ORGANISM: Homo sapiens

<400> SEQUENCE: 11

Gln Arg Ala Cys Val Ala Ala Cys Thr Val Ala Ala Arg Cys Pro
1               5                   10                  15

Gly Arg Gly Val Gly Asp Arg Ser Gln Ser Gly Ala Ser Tyr Arg Pro
                20                  25                  30

Ile Cys Gly Pro Lys Val Gly Pro Thr Glu Met Leu Arg Gly Met
            35                  40                  45

Tyr Leu Thr Arg Asn Gly Asn Leu Gln Arg Arg His Thr Met Lys Glu
    50                  55                  60

Ala Lys Asp Met Lys Asn Lys Leu Gly Ile Phe Arg Arg Asn Glu
65                  70                  75                  80

Ser Pro Gly Ala Pro Pro Ala Gly Lys Ala Asp Lys Met Met Lys Ser
                85                  90                  95

Phe Lys Pro Thr Ser Glu Glu Ala Leu Lys Trp Gly Glu Ser Leu Glu
            100                 105                 110

Lys Leu Leu Val His Lys Tyr Gly Leu Ala Val Phe Gln Ala Phe Leu
        115                 120                 125

Arg Thr Glu Phe Ser Glu Glu Asn Leu Glu Phe Trp Leu Ala Cys Glu
    130                 135                 140

Asp Phe Lys Lys Val Lys Ser Gln Ser Lys Met Ala Ser Lys Ala Lys
145                 150                 155                 160

Lys Ile Phe Ala Glu Tyr Ile Ala Ile Gln Ala Cys Lys Glu Val Asn
                165                 170                 175

Leu Asp Ser Tyr Thr Arg Glu His Thr Lys Asp Asn Leu Gln Ser Val
            180                 185                 190

Thr Arg Gly Cys Phe Asp Leu Ala Gln Lys Arg Ile Phe Gly Leu Met
        195                 200                 205

Glu Lys Asp Ser Tyr Pro Arg Phe Leu Arg Ser Asp Leu Tyr Leu Asp
    210                 215                 220

Leu Ile Asn Gln Lys Lys Met Ser Pro Pro Leu
225                 230                 235

<210> SEQ ID NO 12
<211> LENGTH: 359
```

<212> TYPE: PRT
<213> ORGANISM: Homo sapiens

<400> SEQUENCE: 12

Met Pro Leu Glu Leu Glu Leu Cys Pro Gly Arg Trp Val Gly Gly Gln
1               5                   10                  15

His Pro Cys Phe Ile Ile Ala Glu Ile Gly Gln Asn His Gln Gly Asp
            20                  25                  30

Leu Asp Val Ala Lys Arg Met Ile Arg Met Ala Lys Glu Cys Gly Ala
        35                  40                  45

Asp Cys Ala Lys Phe Gln Lys Ser Glu Leu Glu Phe Lys Phe Asn Arg
    50                  55                  60

Lys Ala Leu Asp Arg Pro Tyr Thr Ser Lys His Ser Trp Gly Lys Thr
65                  70                  75                  80

Tyr Gly Glu His Lys Arg His Leu Glu Phe Ser His Asp Gln Tyr Arg
                85                  90                  95

Glu Leu Gln Arg Tyr Ala Glu Glu Val Gly Ile Phe Phe Thr Ala Ser
            100                 105                 110

Gly Met Asp Glu Met Ala Val Glu Phe Leu His Glu Leu Asn Val Pro
        115                 120                 125

Phe Phe Lys Val Gly Ser Gly Asp Thr Asn Asn Phe Pro Tyr Leu Glu
    130                 135                 140

Lys Thr Ala Lys Lys Gly Arg Pro Met Val Ile Ser Ser Gly Met Gln
145                 150                 155                 160

Ser Met Asp Thr Met Lys Gln Val Tyr Gln Ile Val Lys Pro Leu Asn
                165                 170                 175

Pro Asn Phe Cys Phe Leu Gln Cys Thr Ser Ala Tyr Pro Leu Gln Pro
            180                 185                 190

Glu Asp Val Asn Leu Arg Val Ile Ser Glu Tyr Gln Lys Leu Phe Pro
        195                 200                 205

Asp Ile Pro Ile Gly Tyr Ser Gly His Glu Thr Gly Ile Ala Ile Ser
    210                 215                 220

Val Ala Ala Val Ala Leu Gly Ala Lys Val Leu Glu Arg His Ile Thr
225                 230                 235                 240

Leu Asp Lys Thr Trp Lys Gly Ser Asp His Ser Ala Ser Leu Glu Pro
                245                 250                 255

Gly Glu Leu Ala Glu Leu Val Arg Ser Val Arg Leu Val Glu Arg Ala
            260                 265                 270

Leu Gly Ser Pro Thr Lys Gln Leu Leu Pro Cys Glu Met Ala Cys Asn
        275                 280                 285

Glu Lys Leu Gly Lys Ser Val Val Ala Lys Val Lys Ile Pro Glu Gly
    290                 295                 300

Thr Ile Leu Thr Met Asp Met Leu Thr Val Lys Val Gly Glu Pro Lys
305                 310                 315                 320

Gly Tyr Pro Pro Glu Asp Ile Phe Asn Leu Val Gly Lys Lys Val Leu
                325                 330                 335

Val Thr Val Glu Glu Asp Asp Thr Ile Met Glu Glu Leu Val Asp Asn
            340                 345                 350

His Gly Lys Lys Ile Lys Ser
        355

<210> SEQ ID NO 13
<211> LENGTH: 91
<212> TYPE: PRT
<213> ORGANISM: Homo sapiens

<400> SEQUENCE: 13

Met Cys Met Asp Pro Lys Cys Glu Lys Leu Ala Ile Thr Arg Ser Leu
1               5                   10                  15

Ala Ser Ala Gln Ser Leu Ser Tyr His Gln Asn Gln Gly His Arg Gly
            20                  25                  30

Arg Leu Thr Ala Ser Leu Asn Thr Leu Arg Glu Ala Asp Leu Gly Gln
        35                  40                  45

Val Thr Arg Val Tyr Lys Ser Gln Asp Ser Arg Leu Gly Leu Val His
50                  55                  60

Gly Arg Thr Asp Glu Gln Leu His Ser Cys Ser Arg Thr Asp Gln Asp
65                  70                  75                  80

Lys Ala Met Leu Glu Leu Gly Pro His Ile Cys
                85                  90

<210> SEQ ID NO 14
<211> LENGTH: 470
<212> TYPE: PRT
<213> ORGANISM: Homo sapiens

<400> SEQUENCE: 14

Met Ser Val Thr Asp Gln Ala Phe Val Thr Leu Ala Thr Asn Asp Ile
1               5                   10                  15

Tyr Cys Gln Gly Ala Leu Val Leu Gly Gln Ser Leu Arg Arg His Arg
            20                  25                  30

Leu Thr Arg Lys Leu Val Val Leu Ile Thr Pro Gln Val Ser Ser Leu
        35                  40                  45

Leu Arg Val Ile Leu Ser Lys Val Phe Asp Glu Val Ile Glu Val Asn
50                  55                  60

Leu Ile Asp Ser Ala Asp Tyr Ile His Leu Ala Phe Leu Lys Arg Pro
65                  70                  75                  80

Glu Leu Gly Leu Thr Leu Thr Lys Leu His Cys Trp Thr Leu Thr His
                85                  90                  95

Tyr Ser Lys Cys Val Phe Leu Asp Ala Asp Thr Leu Val Leu Ser Asn
            100                 105                 110

Val Asp Glu Leu Phe Asp Arg Gly Glu Phe Ser Ala Ala Pro Asp Pro
        115                 120                 125

Gly Trp Pro Asp Cys Phe Asn Ser Gly Val Phe Val Phe Gln Pro Ser
    130                 135                 140

Leu His Thr His Lys Leu Leu Leu Gln His Ala Met Glu His Gly Ser
145                 150                 155                 160

Phe Asp Gly Ala Asp Gln Gly Leu Leu Asn Ser Phe Phe Arg Asn Trp
                165                 170                 175

Ser Thr Thr Asp Ile His Lys His Leu Pro Phe Ile Tyr Asn Leu Ser
            180                 185                 190

Ser Asn Thr Met Tyr Thr Tyr Ser Pro Ala Phe Lys Gln Phe Gly Ser
        195                 200                 205

Ser Ala Lys Val Val His Phe Leu Gly Ser Met Lys Pro Trp Asn Tyr
    210                 215                 220

Lys Tyr Asn Pro Gln Ser Gly Ser Val Leu Glu Gln Gly Ser Val Ser
225                 230                 235                 240

Ser Ser Gln His Gln Ala Ala Phe Leu His Leu Trp Trp Thr Val Tyr
                245                 250                 255

Gln Asn Asn Val Leu Pro Leu Tyr Lys Ser Val Gln Ala Gly Glu Ala
            260                 265                 270

-continued

```
Arg Ala Ser Pro Gly His Thr Leu Cys Arg Ser Asp Val Gly Gly Pro
        275                 280                 285

Cys Ala Asp Ser Ala Ser Gly Val Gly Glu Pro Cys Glu Asn Ser Thr
290                 295                 300

Pro Ser Ala Gly Val Pro Cys Ala Asn Ser Pro Leu Gly Ser Asn Gln
305                 310                 315                 320

Pro Ala Gln Gly Leu Pro Glu Pro Thr Gln Ile Val Asp Glu Thr Leu
                325                 330                 335

Ser Leu Pro Glu Gly Arg Arg Ser Glu Asp Met Ile Ala Cys Pro Glu
                340                 345                 350

Thr Glu Thr Pro Ala Val Ile Thr Cys Asp Pro Leu Ser Gln Pro Ser
        355                 360                 365

Pro Gln Pro Ala Asp Phe Thr Glu Thr Glu Thr Ile Leu Gln Pro Ala
370                 375                 380

Asn Lys Val Glu Ser Val Ser Ser Glu Glu Thr Phe Glu Pro Ser Gln
385                 390                 395                 400

Glu Leu Pro Ala Glu Ala Leu Arg Asp Pro Ser Leu Gln Asp Ala Leu
                405                 410                 415

Glu Val Asp Leu Ala Val Ser Val Ser Gln Ile Ser Ile Glu Glu Lys
                420                 425                 430

Val Lys Glu Leu Ser Pro Glu Glu Glu Arg Arg Lys Trp Glu Glu Gly
        435                 440                 445

Arg Ile Asp Tyr Met Gly Lys Asp Ala Phe Ala Arg Ile Gln Glu Lys
450                 455                 460

Leu Asp Arg Phe Leu Gln
465                 470

<210> SEQ ID NO 15
<211> LENGTH: 209
<212> TYPE: PRT
<213> ORGANISM: Homo sapiens

<400> SEQUENCE: 15

Met Lys Phe Lys Leu His Val Asn Ser Ala Arg Gln Tyr Lys Asp Leu
1               5                   10                  15

Trp Asn Met Ser Asp Asp Lys Pro Phe Leu Cys Thr Ala Pro Gly Cys
                20                  25                  30

Gly Gln Arg Phe Thr Asn Glu Asp His Leu Ala Val His Lys His Lys
            35                  40                  45

His Glu Met Thr Leu Lys Phe Gly Pro Ala Arg Asn Asp Ser Val Ile
    50                  55                  60

Val Ala Asp Gln Thr Pro Thr Pro Thr Arg Phe Leu Lys Asn Cys Glu
65                  70                  75                  80

Glu Val Gly Leu Phe Asn Glu Leu Ala Ser Pro Phe Glu Asn Glu Phe
                85                  90                  95

Lys Lys Ala Ser Glu Asp Asp Ile Lys Lys Met Pro Leu Asp Leu Ser
                100                 105                 110

Pro Leu Ala Thr Pro Ile Ile Arg Ser Lys Ile Glu Glu Pro Ser Val
            115                 120                 125

Val Glu Thr Thr His Gln Asp Ser Pro Leu Pro His Pro Glu Ser Thr
    130                 135                 140

Thr Ser Asp Glu Lys Glu Val Pro Leu Ala Gln Thr Ala Gln Pro Thr
145                 150                 155                 160

Ser Ala Ile Val Arg Pro Ala Ser Leu Gln Val Pro Asn Val Leu Leu
```

```
                        165                 170                 175
Thr Ser Ser Asp Ser Ser Val Ile Ile Gln Gln Ala Val Pro Ser Pro
            180                 185                 190
Thr Ser Ser Thr Val Ile Thr Gln Ala Pro Ser Ser Asn Arg Pro Ile
        195                 200                 205
Val

<210> SEQ ID NO 16
<211> LENGTH: 292
<212> TYPE: PRT
<213> ORGANISM: Homo sapiens

<400> SEQUENCE: 16

Met Gly Asn Gln Leu Asp Arg Ile Thr His Leu Asn Tyr Ser Glu Leu
1               5                   10                  15
Pro Thr Gly Asp Pro Ser Gly Ile Glu Lys Asp Glu Leu Arg Val Gly
            20                  25                  30
Val Ala Tyr Phe Phe Ser Asp Asp Glu Asp Leu Asp Glu Arg Gly
        35                  40                  45
Gln Pro Asp Lys Phe Gly Val Lys Ala Pro Pro Gly Cys Thr Pro Cys
    50                  55                  60
Pro Glu Ser Pro Ser Arg His His His Leu Leu His Gln Leu Val
65                  70                  75                  80
Leu Asn Glu Thr Gln Phe Ser Ala Phe Arg Gly Gln Glu Cys Ile Phe
                85                  90                  95
Ser Lys Val Ser Gly Gly Pro Gln Gly Ala Asp Leu Ser Val Tyr Ala
            100                 105                 110
Val Thr Ala Leu Pro Ala Leu Cys Glu Pro Gly Asp Leu Leu Glu Leu
        115                 120                 125
Leu Trp Leu Gln His Ala Pro Glu Pro Pro Ala Pro Ala Pro His Trp
    130                 135                 140
Ala Val Tyr Val Gly Gly Gly Gln Ile Ile His Leu His Gln Gly Glu
145                 150                 155                 160
Ile Arg Gln Asp Ser Leu Tyr Glu Ala Gly Ala Ala Asn Val Gly Arg
                165                 170                 175
Val Val Asn Ser Trp Tyr Arg Tyr Arg Pro Leu Val Ala Glu Leu Val
            180                 185                 190
Val Gln Asn Ala Cys Gly His Leu Gly Leu Lys Ser Glu Glu Ile Cys
        195                 200                 205
Trp Thr Asn Ser Glu Ser Phe Ala Ala Trp Cys Arg Phe Gly Lys Arg
    210                 215                 220
Glu Phe Lys Ala Gly Gly Glu Val Pro Ala Gly Thr Gln Pro Pro Gln
225                 230                 235                 240
Gln Gln Tyr Tyr Leu Lys Val His Leu Gly Glu Asn Lys Val His Thr
                245                 250                 255
Ala Arg Phe His Ser Leu Glu Asp Leu Ile Arg Glu Lys Arg Arg Ile
            260                 265                 270
Asp Ala Ser Gly Arg Leu Arg Val Leu Gln Glu Leu Ala Asp Leu Val
        275                 280                 285
Asp Asp Lys Glu
    290

<210> SEQ ID NO 17
<211> LENGTH: 279
<212> TYPE: PRT
```

-continued

<213> ORGANISM: Homo sapiens

<400> SEQUENCE: 17

Met Ser Val Ala Gly Leu Lys Lys Gln Phe His Lys Ala Thr Gln Lys
1               5                   10                  15

Val Ser Glu Lys Val Gly Gly Ala Glu Gly Thr Lys Leu Asp Asp Asp
            20                  25                  30

Phe Lys Glu Met Glu Arg Lys Val Asp Val Thr Ser Arg Ala Val Met
        35                  40                  45

Glu Ile Met Thr Lys Thr Ile Glu Tyr Leu Gln Pro Asn Pro Ala Ser
    50                  55                  60

Arg Ala Lys Leu Ser Met Ile Asn Thr Met Ser Lys Ile Arg Gly Gln
65                  70                  75                  80

Glu Lys Gly Pro Gly Tyr Pro Gln Ala Glu Ala Leu Leu Ala Glu Ala
                85                  90                  95

Met Leu Lys Phe Gly Arg Glu Leu Gly Asp Asp Cys Asn Phe Gly Pro
            100                 105                 110

Ala Leu Gly Glu Val Gly Glu Ala Met Arg Glu Leu Ser Glu Val Lys
        115                 120                 125

Asp Ser Leu Asp Ile Glu Val Lys Gln Asn Phe Ile Asp Pro Leu Gln
    130                 135                 140

Asn Leu His Asp Lys Asp Leu Arg Glu Ile Gln His His Leu Lys Lys
145                 150                 155                 160

Leu Glu Gly Arg Arg Leu Asp Phe Asp Tyr Lys Lys Glu Arg Gln Gly
                165                 170                 175

Lys Ile Pro Asp Glu Glu Leu Arg Gln Ala Leu Glu Lys Phe Asp Glu
            180                 185                 190

Ser Lys Glu Ile Ala Glu Ser Ser Met Phe Asn Leu Leu Glu Met Asp
        195                 200                 205

Ile Glu Gln Val Ser Gln Leu Ser Ala Leu Val Gln Ala Gln Leu Glu
    210                 215                 220

Tyr His Lys Gln Ala Val Gln Ile Leu Gln Gln Val Thr Val Arg Leu
225                 230                 235                 240

Glu Glu Arg Ile Arg Gln Ala Ser Ser Gln Pro Arg Arg Glu Tyr Gln
                245                 250                 255

Pro Lys Pro Arg Met Ser Leu Glu Phe Pro Thr Gly Asp Ser Thr Gln
            260                 265                 270

Pro Asn Gly Gly Leu Ser His
        275

<210> SEQ ID NO 18
<211> LENGTH: 370
<212> TYPE: PRT
<213> ORGANISM: Homo sapiens

<400> SEQUENCE: 18

Met Glu Ser Ile Phe His Glu Lys Gln Glu Gly Ser Leu Cys Ala Gln
1               5                   10                  15

His Cys Leu Asn Asn Leu Leu Gln Gly Glu Tyr Phe Ser Pro Val Glu
            20                  25                  30

Leu Ser Ser Ile Ala His Gln Leu Asp Glu Glu Glu Arg Met Arg Met
        35                  40                  45

Ala Glu Gly Gly Val Thr Ser Glu Asp Tyr Arg Thr Phe Leu Gln Gln
    50                  55                  60

Pro Ser Gly Asn Met Asp Asp Ser Gly Phe Phe Ser Ile Gln Val Ile

```
            65                  70                  75                  80
    Ser Asn Ala Leu Lys Val Trp Gly Leu Glu Leu Ile Leu Phe Asn Ser
                    85                  90                  95

Pro Glu Tyr Gln Arg Leu Arg Ile Asp Pro Ile Asn Glu Arg Ser Phe
                100                 105                 110

Ile Cys Asn Tyr Lys Glu His Trp Phe Thr Val Arg Lys Leu Gly Lys
                115                 120                 125

Gln Trp Phe Asn Leu Asn Ser Leu Leu Thr Gly Pro Glu Leu Ile Ser
    130                 135                 140

Asp Thr Tyr Leu Ala Leu Phe Leu Ala Gln Leu Gln Gln Gly Tyr
    145                 150                 155                 160

Ser Ile Phe Val Val Lys Gly Asp Leu Pro Asp Cys Glu Ala Asp Gln
                    165                 170                 175

Leu Leu Gln Met Ile Arg Val Gln Gln Met His Arg Pro Lys Leu Ile
                    180                 185                 190

Gly Glu Glu Leu Ala Gln Leu Lys Glu Gln Arg Val His Lys Thr Asp
                195                 200                 205

Leu Glu Arg Val Leu Glu Ala Asn Asp Gly Ser Gly Met Leu Asp Glu
    210                 215                 220

Asp Glu Glu Asp Leu Gln Arg Ala Leu Ala Leu Ser Arg Gln Glu Ile
    225                 230                 235                 240

Asp Met Glu Asp Glu Gly Ala Asp Leu Arg Arg Ala Ile Gln Leu Ser
                    245                 250                 255

Met Gln Gly Ser Ser Arg Asn Ile Ser Gln Asp Met Thr Gln Thr Ser
                    260                 265                 270

Gly Thr Asn Leu Thr Ser Glu Glu Leu Arg Lys Arg Arg Glu Ala Tyr
                275                 280                 285

Phe Glu Lys Gln Gln Gln Lys Gln Gln Gln Gln Gln Gln Gln Gln Gln
                290                 295                 300

Gln Gln Gln Gln Gln Gln Gln Gln Gln Gly Asp Leu Ser Gly Gln
    305                 310                 315                 320

Ser Ser His Pro Cys Glu Arg Pro Ala Thr Ser Ser Gly Ala Leu Gly
                    325                 330                 335

Ser Asp Leu Gly Asp Ala Met Ser Glu Glu Asp Met Leu Gln Ala Ala
                    340                 345                 350

Val Thr Met Ser Leu Glu Thr Val Arg Asn Asp Leu Lys Thr Glu Gly
                355                 360                 365

Lys Lys
        370

<210> SEQ ID NO 19
<211> LENGTH: 467
<212> TYPE: PRT
<213> ORGANISM: Homo sapiens

<400> SEQUENCE: 19

Met Ala Thr Arg Ser Cys Arg Glu Lys Ala Gln Lys Leu Asn Glu Gln
    1               5                   10                  15

His Gln Leu Ile Leu Ser Lys Leu Leu Arg Glu Glu Asp Asn Lys Tyr
                20                  25                  30

Cys Ala Asp Cys Glu Ala Lys Gly Pro Arg Trp Ala Ser Trp Asn Ile
                35                  40                  45

Gly Val Phe Ile Cys Ile Arg Cys Ala Gly Ile His Arg Asn Leu Gly
            50                  55                  60
```

-continued

```
Val His Ile Ser Arg Val Lys Ser Val Asn Leu Asp Gln Trp Thr Ala
 65                  70                  75                  80

Glu Gln Ile Gln Cys Met Gln Asp Met Gly Asn Thr Lys Ala Arg Leu
                 85                  90                  95

Leu Tyr Glu Ala Asn Leu Pro Glu Asn Phe Arg Arg Pro Gln Thr Asp
            100                 105                 110

Gln Ala Val Glu Phe Phe Ile Arg Asp Lys Tyr Glu Lys Lys Lys Tyr
        115                 120                 125

Tyr Asp Lys Asn Ala Ile Ala Ile Thr Asn Ile Ser Ser Asp Ala
    130                 135                 140

Pro Leu Gln Pro Leu Val Ser Ser Pro Ser Leu Gln Ala Ala Val Asp
145                 150                 155                 160

Lys Asn Lys Leu Glu Lys Glu Lys Lys Lys Glu Glu Lys Lys
                165                 170                 175

Arg Glu Lys Glu Pro Glu Lys Pro Ala Lys Pro Leu Thr Ala Glu Lys
                180                 185                 190

Leu Gln Lys Lys Asp Gln Gln Leu Glu Pro Lys Lys Ser Thr Ser Pro
        195                 200                 205

Lys Lys Ala Ala Glu Pro Thr Val Asp Leu Leu Gly Leu Asp Gly Pro
210                 215                 220

Ala Val Ala Pro Val Thr Asn Gly Asn Thr Thr Val Pro Pro Leu Asn
225                 230                 235                 240

Asp Asp Leu Asp Ile Phe Gly Pro Met Ile Ser Asn Pro Leu Pro Ala
                245                 250                 255

Thr Val Met Pro Pro Ala Gln Gly Thr Pro Ser Ala Pro Ala Ala Ala
                260                 265                 270

Thr Leu Ser Thr Val Thr Ser Gly Asp Leu Asp Leu Phe Thr Glu Gln
        275                 280                 285

Thr Thr Lys Ser Glu Glu Val Ala Lys Lys Gln Leu Ser Lys Asp Ser
        290                 295                 300

Ile Leu Ser Leu Tyr Gly Thr Gly Thr Ile Gln Gln Ser Thr Pro
305                 310                 315                 320

Gly Val Phe Met Gly Pro Thr Asn Ile Pro Phe Thr Ser Gln Ala Pro
                325                 330                 335

Ala Ala Phe Gln Gly Phe Pro Ser Met Gly Val Pro Val Pro Ala Ala
                340                 345                 350

Pro Gly Leu Ile Gly Asn Val Met Gly Gln Ser Pro Ser Met Met Val
            355                 360                 365

Gly Met Pro Met Pro Asn Gly Phe Met Gly Asn Ala Gln Thr Gly Val
370                 375                 380

Met Pro Leu Pro Gln Asn Val Val Gly His Gln Gly Met Val Gly
385                 390                 395                 400

Gln Met Gly Ala Pro Gln Ser Lys Phe Gly Leu Pro Ala Gln Gln
                405                 410                 415

Pro Gln Trp Ser Leu Ser Gln Met Asn Gln Met Ala Gly Met Ser
                420                 425                 430

Ile Ser Ser Ala Thr Pro Thr Ala Gly Phe Gly Gln Pro Ser Ser Thr
            435                 440                 445

Thr Ala Gly Trp Ser Gly Ser Ser Gly Gln Thr Leu Ser Thr Gln
        450                 455                 460

Leu Trp Lys
465
```

<210> SEQ ID NO 20
<211> LENGTH: 514
<212> TYPE: PRT
<213> ORGANISM: Homo sapiens

<400> SEQUENCE: 20

| Met | Gly | Arg | Lys | Lys | Ile | Gln | Ile | Gln | Arg | Ile | Thr | Asp | Glu | Arg | Asn |
| 1 | | | | 5 | | | | | 10 | | | | | 15 | |

| Arg | Gln | Val | Thr | Phe | Thr | Lys | Arg | Lys | Phe | Gly | Leu | Met | Lys | Lys | Ala |
| | | | 20 | | | | | 25 | | | | | 30 | | |

| Tyr | Glu | Leu | Ser | Val | Leu | Cys | Asp | Cys | Glu | Ile | Ala | Leu | Ile | Ile | Phe |
| | | | 35 | | | | | 40 | | | | | 45 | | |

| Asn | His | Ser | Asn | Lys | Leu | Phe | Gln | Tyr | Ala | Ser | Thr | Asp | Met | Asp | Lys |
| | | 50 | | | | | 55 | | | | | 60 | | | |

| Val | Leu | Leu | Lys | Tyr | Thr | Glu | Tyr | Asn | Glu | Pro | His | Glu | Ser | Arg | Thr |
| 65 | | | | | 70 | | | | | 75 | | | | | 80 |

| Asn | Ala | Asp | Ile | Ile | Glu | Thr | Leu | Arg | Lys | Lys | Gly | Phe | Asn | Gly | Cys |
| | | | | 85 | | | | | 90 | | | | | 95 | |

| Asp | Ser | Pro | Glu | Pro | Asp | Gly | Glu | Asp | Ser | Leu | Glu | Gln | Ser | Pro | Leu |
| | | | 100 | | | | | 105 | | | | | 110 | | |

| Leu | Glu | Asp | Lys | Tyr | Arg | Arg | Ala | Ser | Glu | Glu | Leu | Asp | Gly | Leu | Phe |
| | | | 115 | | | | | 120 | | | | | 125 | | |

| Arg | Arg | Tyr | Gly | Ser | Thr | Val | Pro | Ala | Pro | Asn | Phe | Ala | Met | Pro | Val |
| | 130 | | | | | 135 | | | | | 140 | | | | |

| Thr | Val | Pro | Val | Ser | Asn | Gln | Ser | Ser | Leu | Gln | Phe | Ser | Asn | Pro | Ser |
| 145 | | | | | 150 | | | | | 155 | | | | | 160 |

| Gly | Ser | Leu | Val | Thr | Pro | Ser | Leu | Val | Thr | Ser | Ser | Leu | Thr | Asp | Pro |
| | | | | 165 | | | | | 170 | | | | | 175 | |

| Arg | Leu | Leu | Ser | Pro | Gln | Gln | Pro | Ala | Leu | Gln | Arg | Asn | Ser | Val | Ser |
| | | | 180 | | | | | 185 | | | | | 190 | | |

| Pro | Gly | Leu | Pro | Gln | Arg | Pro | Ala | Ser | Ala | Gly | Ala | Met | Leu | Gly | Gly |
| | | | 195 | | | | | 200 | | | | | 205 | | |

| Asp | Leu | Asn | Ser | Ala | Asn | Gly | Ala | Cys | Pro | Ser | Pro | Val | Gly | Asn | Gly |
| | 210 | | | | | 215 | | | | | 220 | | | | |

| Tyr | Val | Ser | Ala | Arg | Ala | Ser | Pro | Gly | Leu | Leu | Pro | Val | Ala | Asn | Gly |
| 225 | | | | | 230 | | | | | 235 | | | | | 240 |

| Asn | Ser | Leu | Asn | Lys | Val | Ile | Pro | Ala | Lys | Ser | Pro | Pro | Pro | Pro | Thr |
| | | | | 245 | | | | | 250 | | | | | 255 | |

| His | Ser | Thr | Gln | Leu | Gly | Ala | Pro | Ser | Arg | Lys | Pro | Asp | Leu | Arg | Val |
| | | | 260 | | | | | 265 | | | | | 270 | | |

| Ile | Thr | Ser | Gln | Ala | Gly | Lys | Gly | Leu | Met | His | His | Leu | Asn | Asn | Ala |
| | | | 275 | | | | | 280 | | | | | 285 | | |

| Gln | Arg | Leu | Gly | Val | Ser | Gln | Ser | Thr | His | Ser | Leu | Thr | Thr | Pro | Val |
| | 290 | | | | | 295 | | | | | 300 | | | | |

| Val | Ser | Val | Ala | Thr | Pro | Ser | Leu | Leu | Ser | Gln | Gly | Leu | Pro | Phe | Ser |
| 305 | | | | | 310 | | | | | 315 | | | | | 320 |

| Ser | Met | Pro | Thr | Ala | Tyr | Asn | Thr | Asp | Tyr | Gln | Leu | Thr | Ser | Ala | Glu |
| | | | | 325 | | | | | 330 | | | | | 335 | |

| Leu | Ser | Ser | Leu | Pro | Ala | Phe | Ser | Ser | Pro | Gly | Gly | Leu | Ser | Leu | Gly |
| | | | 340 | | | | | 345 | | | | | 350 | | |

| Asn | Val | Thr | Ala | Trp | Gln | Gln | Pro | Gln | Gln | Pro | Gln | Gln | Pro | Gln | Gln |
| | | | 355 | | | | | 360 | | | | | 365 | | |

| Pro | Gln | Pro | Pro | Gln | Gln | Pro | Pro | Gln | Pro | Gln | Gln | Pro | Gln | Pro |
| | 370 | | | | | 375 | | | | | 380 | | | | |

```
Gln Gln Pro Gln Gln Pro Gln Gln Pro Pro Gln Gln Ser His Leu
385                 390                 395                 400

Val Pro Val Ser Leu Ser Asn Leu Ile Pro Gly Ser Pro Leu Pro His
            405                 410                 415

Val Gly Ala Ala Leu Thr Val Thr Thr His Pro His Ile Ser Ile Lys
        420                 425                 430

Ser Glu Pro Val Ser Pro Ser Arg Glu Arg Ser Pro Ala Pro Pro Pro
    435                 440                 445

Pro Ala Val Phe Pro Ala Ala Arg Pro Glu Pro Gly Asp Gly Leu Ser
    450                 455                 460

Ser Pro Ala Gly Gly Ser Tyr Glu Thr Gly Asp Arg Asp Asp Gly Arg
465                 470                 475                 480

Gly Asp Phe Gly Pro Thr Leu Gly Leu Leu Arg Pro Ala Pro Glu Pro
            485                 490                 495

Glu Ala Glu Gly Ser Ala Val Lys Arg Met Arg Leu Asp Thr Trp Thr
            500                 505                 510

Leu Lys

<210> SEQ ID NO 21
<211> LENGTH: 447
<212> TYPE: PRT
<213> ORGANISM: Homo sapiens

<400> SEQUENCE: 21

Met Ser Asn Asn Gly Leu Asp Ile Gln Asp Lys Pro Pro Ala Pro Pro
1               5                   10                  15

Met Arg Asn Thr Ser Thr Met Ile Gly Ala Gly Ser Lys Asp Ala Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
            100                 105                 110

Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Pro Val Ile Ala Pro
            180                 185                 190

Arg Pro Glu His Thr Lys Ser Val Tyr Thr Arg Ser Val Ile Glu Pro
        195                 200                 205

Leu Pro Val Thr Pro Thr Arg Asp Val Ala Thr Ser Pro Ile Ser Pro
    210                 215                 220

Thr Glu Asn Asn Thr Thr Pro Pro Asp Ala Leu Thr Arg Asn Thr Glu
225                 230                 235                 240
```

Lys Gln Lys Lys Lys Pro Lys Met Ser Asp Glu Glu Ile Leu Glu Lys
                245                 250                 255

Leu Arg Ser Ile Val Ser Val Gly Asp Pro Lys Lys Tyr Thr Arg
        260                 265                 270

Phe Glu Lys Ile Gly Gln Gly Ala Ser Gly Thr Val Tyr Thr Ala Met
            275                 280                 285

Asp Val Ala Thr Gly Gln Glu Val Ala Ile Lys Gln Met Asn Leu Gln
290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
            340                 345                 350

Thr Asp Val Val Thr Glu Thr Cys Met Asp Glu Gly Gln Ile Ala Ala
        355                 360                 365

Val Cys Arg Glu Cys Leu Gln Ala Leu Glu Phe Leu His Ser Asn Gln
    370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
            420                 425                 430

Pro Glu Val Val Thr Arg Lys Ala Tyr Gly Pro Lys Val Asp Ile
        435                 440                 445

<210> SEQ ID NO 22
<211> LENGTH: 383
<212> TYPE: PRT
<213> ORGANISM: Homo sapiens

<400> SEQUENCE: 22

Met Glu Arg Leu Gln Lys Gln Pro Leu Thr Ser Pro Gly Ser Val Ser
1               5                   10                  15

Pro Ser Arg Asp Ser Ser Val Pro Gly Ser Pro Ser Ser Ile Val Ala
                20                  25                  30

Lys Met Asp Asn Gln Val Leu Gly Tyr Lys Asp Leu Ala Ala Ile Pro
            35                  40                  45

Lys Asp Lys Ala Ile Leu Asp Ile Glu Arg Pro Asp Leu Met Ile Tyr
        50                  55                  60

Glu Pro His Phe Thr Tyr Ser Leu Leu Glu His Val Glu Leu Pro Arg
65                  70                  75                  80

Ser Arg Glu Arg Ser Leu Ser Pro Lys Ser Thr Ser Pro Pro Pro Ser
                85                  90                  95

Pro Glu Val Trp Ala Asp Ser Arg Ser Pro Gly Ile Ile Ser Gln Ala
            100                 105                 110

Ser Ala Pro Arg Thr Thr Gly Thr Pro Arg Thr Ser Leu Pro His Phe
        115                 120                 125

His His Pro Glu Thr Ser Arg Pro Asp Ser Asn Ile Tyr Lys Lys Pro
    130                 135                 140

Pro Ile Tyr Lys Gln Arg Glu Ser Val Gly Gly Ser Pro Gln Thr Lys
145                 150                 155                 160

His Leu Ile Glu Asp Leu Ile Ile Glu Ser Ser Lys Phe Pro Ala Ala
                165                 170                 175

Gln Pro Pro Asp Pro Asn Gln Pro Ala Lys Ile Glu Thr Asp Tyr Trp
            180                 185                 190

Pro Cys Pro Pro Ser Leu Ala Val Val Glu Thr Glu Trp Arg Lys Arg
            195                 200                 205

Lys Ala Ser Arg Arg Gly Ala Glu Glu Glu Glu Glu Glu Glu Asp Asp
210                 215                 220

Asp Ser Gly Glu Glu Met Lys Ala Leu Arg Glu Arg Gln Arg Glu Glu
225                 230                 235                 240

Leu Ser Lys Val Thr Ser Asn Leu Gly Lys Met Ile Leu Lys Glu Glu
            245                 250                 255

Met Glu Lys Ser Leu Pro Ile Arg Arg Lys Thr Arg Ser Leu Pro Asp
            260                 265                 270

Arg Thr Pro Phe His Thr Ser Leu His Gln Gly Thr Ser Lys Ser Ser
            275                 280                 285

Ser Leu Pro Ala Tyr Gly Arg Thr Thr Leu Ser Arg Leu Gln Ser Thr
            290                 295                 300

Glu Phe Ser Pro Ser Gly Ser Glu Thr Gly Ser Pro Gly Leu Gln Ile
305                 310                 315                 320

Tyr Pro Tyr Glu Met Leu Val Val Thr Asn Lys Gly Arg Thr Lys Leu
            325                 330                 335

Pro Pro Gly Val Asp Arg Met Arg Leu Glu Arg His Leu Ser Ala Glu
            340                 345                 350

Asp Phe Ser Arg Val Phe Ala Met Ser Pro Glu Glu Phe Gly Lys Leu
            355                 360                 365

Ala Leu Trp Lys Arg Asn Glu Leu Lys Lys Lys Ala Ser Leu Phe
            370                 375                 380

<210> SEQ ID NO 23
<211> LENGTH: 226
<212> TYPE: PRT
<213> ORGANISM: Homo sapiens

<400> SEQUENCE: 23

Met Ser Arg Ile Tyr His Asp Gly Ala Leu Arg Asn Lys Ala Val Gln
1               5                   10                  15

Ser Val Arg Leu Pro Gly Ala Trp Asp Pro Ala Ala His Gln Gly Gly
            20                  25                  30

Asn Gly Val Leu Leu Glu Gly Glu Leu Ile Asp Val Ser Arg His Ser
        35                  40                  45

Ile Leu Asp Thr His Gly Arg Lys Glu Arg Tyr Tyr Val Leu Tyr Ile
    50                  55                  60

Arg Pro Ser His Ile His Arg Arg Lys Phe Asp Ala Lys Gly Asn Glu
65                  70                  75                  80

Ile Glu Pro Asn Phe Ser Ala Thr Arg Lys Val Asn Thr Gly Phe Leu
            85                  90                  95

Met Ser Ser Tyr Lys Val Glu Ala Lys Gly Asp Thr Arg Leu Thr
            100                 105                 110

Pro Glu Ala Leu Lys Gly Leu Val Asn Lys Pro Glu Leu Leu Ala Leu
            115                 120                 125

Thr Glu Ser Leu Thr Pro Asp His Thr Val Ala Phe Trp Met Pro Glu
            130                 135                 140

Ser Glu Met Glu Val Met Glu Leu Glu Leu Gly Ala Gly Val Arg Leu
145                 150                 155                 160

Lys Thr Arg Gly Asp Gly Pro Phe Leu Asp Ser Leu Ala Lys Leu Glu

```
                    165                 170                 175
Ala Gly Thr Val Thr Lys Cys Asn Phe Thr Gly Asp Gly Lys Thr Gly
                180                 185                 190

Ala Ser Trp Thr Asp Asn Ile Met Ala Gln Lys Cys Ser Lys Gly Ala
            195                 200                 205

Ala Ala Glu Ile Arg Glu Gln Gly Asp Gly Ala Glu Asp Glu Glu Trp
        210                 215                 220

Asp Asp
225

<210> SEQ ID NO 24
<211> LENGTH: 253
<212> TYPE: PRT
<213> ORGANISM: Homo sapiens

<400> SEQUENCE: 24

Met Glu Pro Leu Gln Gln Gln Gln Gln Gln Gln Gln Gln Gln Gln Lys
1               5                   10                  15

Gln Pro His Leu Ala Pro Leu Gln Met Asp Ala Arg Glu Lys Gln Gly
            20                  25                  30

Gln Gln Met Arg Glu Ala Gln Phe Leu Tyr Ala Gln Lys Leu Val Thr
        35                  40                  45

Gln Pro Thr Leu Leu Ser Ala Thr Ala Gly Arg Pro Ser Gly Ser Thr
    50                  55                  60

Pro Leu Gly Pro Leu Ala Arg Val Pro Thr Ala Ala Val Ala Gln
65                  70                  75                  80

Val Phe Glu Arg Gly Asn Met Asn Ser Glu Pro Glu Glu Glu Asp Gly
                85                  90                  95

Gly Leu Glu Asp Glu Asp Gly Asp Glu Val Ala Glu Val Ala Glu
            100                 105                 110

Lys Glu Thr Gln Ala Ala Ser Lys Tyr Phe His Val Gln Lys Val Ala
        115                 120                 125

Arg Gln Asp Pro Arg Val Ala Pro Met Ser Asn Leu Leu Pro Ala Pro
    130                 135                 140

Gly Leu Pro Pro His Gly Gln Gln Ala Lys Glu Asp His Thr Lys Asp
145                 150                 155                 160

Ala Ser Lys Ala Ser Pro Ser Val Ser Thr Ala Gly Gln Pro Asn Trp
                165                 170                 175

Asn Leu Asp Glu Gln Leu Lys Gln Asn Gly Gly Leu Ala Trp Ser Asp
            180                 185                 190

Asp Ala Asp Gly Gly Arg Gly Arg Glu Ile Ser Arg Asp Phe Ala Lys
        195                 200                 205

Leu Tyr Glu Leu Asp Gly Asp Pro Glu Arg Lys Glu Phe Leu Asp Asp
    210                 215                 220

Leu Phe Val Phe Met Gln Lys Arg Gly Glu Cys Ala Ser Thr His His
225                 230                 235                 240

Ser Asn Ser Gly Asn Thr Asp Arg Val Pro Thr Val Cys
                245                 250

<210> SEQ ID NO 25
<211> LENGTH: 585
<212> TYPE: PRT
<213> ORGANISM: Homo sapiens

<400> SEQUENCE: 25

Met Lys Lys Gln Ala Asn Lys Thr Ala Ser Ser Gly Ser Ser Asp Lys
```

-continued

```
1               5                   10                  15
Asp Ser Ser Ala Glu Ser Ser Ala Pro Glu Glu Gly Glu Val Ser Asp
                20                  25                  30
Ser Asp Ser Asn Ser Ser Ser Ser Ser Asp Ser Asp Ser Ser Ser
                35                  40                  45
Glu Asp Glu Glu Phe His Asp Gly Tyr Gly Glu Asp Leu Met Gly Asp
    50                      55                  60
Glu Glu Asp Arg Ala Arg Leu Glu Gln Met Thr Glu Lys Glu Arg Glu
65              70                      75                  80
Gln Glu Leu Phe Asn Arg Ile Glu Lys Arg Glu Val Leu Lys Arg Arg
                85                  90                  95
Phe Glu Ile Lys Lys Lys Leu Lys Thr Ala Lys Lys Glu Lys Lys
                100                 105                 110
Glu Lys Lys Lys Gln Glu Glu Gln Lys Lys Lys Leu Thr
                115                 120                 125
Gln Ile Gln Glu Ser Gln Val Thr Ser His Asn Lys Glu Arg Arg Ser
    130                     135                 140
Lys Arg Asp Glu Lys Leu Asp Lys Lys Ser Gln Ala Met Glu Glu Leu
145                 150                 155                 160
Lys Ala Glu Arg Glu Lys Arg Lys Asn Arg Thr Ala Glu Leu Leu Ala
                165                 170                 175
Lys Lys Gln Pro Leu Lys Thr Ser Glu Val Tyr Ser Asp Asp Glu Glu
                180                 185                 190
Glu Glu Glu Asp Asp Lys Ser Ser Glu Lys Ser Asp Arg Ser Ser Arg
                195                 200                 205
Thr Ser Ser Ser Asp Glu Glu Glu Lys Glu Glu Ile Pro Pro Lys
    210                     215                 220
Ser Gln Pro Val Ser Leu Pro Glu Glu Leu Asn Arg Val Arg Leu Ser
225                 230                 235                 240
Arg His Lys Leu Glu Arg Trp Cys His Met Pro Phe Phe Ala Lys Thr
                245                 250                 255
Val Thr Gly Cys Phe Val Arg Ile Gly Ile Gly Asn His Asn Ser Lys
                260                 265                 270
Pro Val Tyr Arg Val Ala Glu Ile Thr Gly Val Val Glu Thr Ala Lys
                275                 280                 285
Val Tyr Gln Leu Gly Gly Thr Arg Thr Asn Lys Gly Leu Gln Leu Arg
                290                 295                 300
His Gly Asn Asp Gln Arg Val Phe Arg Leu Glu Phe Val Ser Asn Gln
305                 310                 315                 320
Glu Phe Thr Glu Ser Glu Phe Met Lys Trp Lys Glu Ala Met Phe Ser
                325                 330                 335
Ala Gly Met Gln Leu Pro Thr Leu Asp Glu Ile Asn Lys Lys Glu Leu
                340                 345                 350
Ser Ile Lys Glu Ala Leu Asn Tyr Lys Phe Asn Asp Gln Asp Ile Glu
                355                 360                 365
Glu Ile Val Lys Glu Lys Glu Arg Phe Arg Lys Ala Pro Pro Asn Tyr
                370                 375                 380
Ala Met Lys Lys Thr Gln Leu Leu Lys Glu Lys Ala Met Ala Glu Asp
385                 390                 395                 400
Leu Gly Asp Gln Asp Lys Ala Lys Gln Ile Gln Asp Gln Leu Asn Glu
                405                 410                 415
Leu Glu Glu Arg Ala Glu Ala Leu Asp Arg Gln Arg Thr Lys Asn Ile
                420                 425                 430
```

-continued

```
Ser Ala Ile Ser Tyr Ile Asn Gln Arg Asn Arg Glu Trp Asn Ile Val
            435                 440                 445

Glu Ser Glu Lys Ala Leu Val Ala Glu Ser His Asn Met Lys Asn Gln
450                 455                 460

Gln Met Asp Pro Phe Thr Arg Arg Gln Cys Lys Pro Thr Ile Val Ser
465                 470                 475                 480

Asn Ser Arg Asp Pro Ala Val Gln Ala Ala Ile Leu Ala Gln Leu Asn
                485                 490                 495

Ala Lys Tyr Gly Ser Gly Val Leu Pro Asp Ala Pro Lys Glu Met Ser
            500                 505                 510

Lys Gly Gln Gly Lys Asp Lys Asp Leu Asn Ser Lys Ser Ala Ser Asp
            515                 520                 525

Leu Ser Glu Asp Leu Phe Lys Val His Asp Phe Asp Val Lys Ile Asp
530                 535                 540

Leu Gln Val Pro Ser Ser Glu Ser Lys Ala Leu Ala Ile Thr Ser Lys
545                 550                 555                 560

Ala Pro Pro Ala Lys Asp Gly Ala Pro Arg Arg Ser Leu Asn Leu Glu
                565                 570                 575

Asp Tyr Lys Lys Arg Arg Gly Leu Ile
            580                 585

<210> SEQ ID NO 26
<211> LENGTH: 129
<212> TYPE: PRT
<213> ORGANISM: Homo sapiens

<400> SEQUENCE: 26

Met Ala Asp Ser Gly Asp Ala Gly Ser Ser Gly Pro Trp Trp Lys Ser
1               5                   10                  15

Leu Thr Asn Ser Arg Lys Lys Ser Lys Glu Ala Ala Val Gly Val Pro
                20                  25                  30

Pro Pro Ala Gln Pro Ala Pro Gly Glu Pro Thr Pro Pro Ala Pro Pro
            35                  40                  45

Ser Pro Asp Trp Thr Ser Ser Ser Arg Glu Asn Gln His Pro Asn Leu
50                  55                  60

Leu Gly Gly Ala Gly Glu Pro Pro Lys Pro Asp Lys Leu Tyr Gly Asp
65                  70                  75                  80

Lys Ser Gly Ser Ser Arg Arg Asn Leu Lys Ile Ser Arg Ser Gly Arg
                85                  90                  95

Phe Lys Glu Lys Arg Lys Val Arg Ala Thr Leu Leu Pro Glu Ala Gly
            100                 105                 110

Arg Ser Pro Glu Glu Ala Gly Phe Pro Gly Asp Pro His Glu Asp Lys
            115                 120                 125

Gln

<210> SEQ ID NO 27
<211> LENGTH: 173
<212> TYPE: PRT
<213> ORGANISM: Homo sapiens

<400> SEQUENCE: 27

Met Asp Val Thr Ile Gln His Pro Trp Phe Lys Arg Thr Leu Gly Pro
1               5                   10                  15

Phe Tyr Pro Ser Arg Leu Phe Asp Gln Phe Phe Gly Glu Gly Leu Phe
                20                  25                  30
```

-continued

Glu Tyr Asp Leu Leu Pro Phe Leu Ser Ser Thr Ile Ser Pro Tyr Tyr
            35                  40                  45

Arg Gln Ser Leu Phe Arg Thr Val Leu Asp Ser Gly Ile Ser Glu Val
 50                  55                  60

Arg Ser Asp Arg Asp Lys Phe Val Ile Phe Leu Asp Val Lys His Phe
 65                  70                  75                  80

Ser Pro Glu Asp Leu Thr Val Lys Val Gln Asp Asp Phe Val Glu Ile
                85                  90                  95

His Gly Lys His Asn Glu Arg Gln Asp Asp His Gly Tyr Ile Ser Arg
            100                 105                 110

Glu Phe His Arg Tyr Arg Leu Pro Ser Asn Val Asp Gln Ser Ala
            115                 120                 125

Leu Ser Cys Ser Leu Ser Ala Asp Gly Met Leu Thr Phe Cys Gly Pro
            130                 135                 140

Lys Ile Gln Thr Gly Leu Asp Ala Thr His Ala Glu Arg Ala Ile Pro
145                 150                 155                 160

Val Ser Arg Glu Glu Lys Pro Thr Ser Ala Pro Ser Ser
                165                 170

<210> SEQ ID NO 28
<211> LENGTH: 598
<212> TYPE: PRT
<213> ORGANISM: Homo sapiens

<400> SEQUENCE: 28

Met Val Gln Lys Thr Ser Met Ser Arg Gly Pro Tyr Pro Pro Ser Gln
 1               5                  10                  15

Glu Ile Pro Met Glu Val Phe Asp Pro Ser Pro Gln Gly Lys Tyr Ser
                20                  25                  30

Lys Arg Lys Gly Arg Phe Lys Arg Ser Asp Gly Ser Thr Ser Ser Asp
            35                  40                  45

Thr Thr Ser Asn Ser Phe Val Arg Gln Gly Ser Ala Glu Ser Tyr Thr
 50                  55                  60

Ser Arg Pro Ser Asp Ser Asp Val Ser Leu Glu Glu Asp Arg Glu Ala
 65                  70                  75                  80

Leu Arg Lys Glu Ala Glu Arg Gln Ala Leu Ala Gln Leu Glu Lys Ala
                85                  90                  95

Lys Thr Lys Pro Val Ala Phe Ala Val Arg Thr Asn Val Gly Tyr Asn
            100                 105                 110

Pro Ser Pro Gly Asp Glu Val Pro Val Gln Gly Val Ala Ile Thr Phe
            115                 120                 125

Glu Pro Lys Asp Phe Leu His Ile Lys Glu Lys Tyr Asn Asn Asp Trp
            130                 135                 140

Trp Ile Gly Arg Leu Val Lys Glu Gly Cys Glu Val Gly Phe Ile Pro
145                 150                 155                 160

Ser Pro Val Lys Leu Asp Ser Leu Arg Leu Leu Gln Glu Gln Lys Leu
                165                 170                 175

Arg Gln Asn Arg Leu Gly Ser Ser Lys Ser Gly Asp Asn Ser Ser Ser
            180                 185                 190

Ser Leu Gly Asp Val Val Thr Gly Thr Arg Arg Pro Thr Pro Pro Ala
            195                 200                 205

Ser Ala Lys Gln Lys Gln Lys Ser Thr Glu His Val Pro Pro Tyr Asp
            210                 215                 220

Val Val Pro Ser Met Arg Pro Ile Ile Leu Val Gly Pro Ser Leu Lys
225                 230                 235                 240

Gly Tyr Glu Val Thr Asp Met Met Gln Lys Ala Leu Phe Asp Phe Leu
                245                 250                 255

Lys His Arg Phe Asp Gly Arg Ile Ser Ile Thr Arg Val Thr Ala Asp
            260                 265                 270

Ile Ser Leu Ala Lys Arg Ser Val Leu Asn Asn Pro Ser Lys His Ile
        275                 280                 285

Ile Ile Glu Arg Ser Asn Thr Arg Ser Ser Leu Ala Glu Val Gln Ser
    290                 295                 300

Glu Ile Glu Arg Ile Phe Glu Leu Ala Arg Thr Leu Gln Leu Val Ala
305                 310                 315                 320

Leu Asp Ala Asp Thr Ile Asn His Pro Ala Gln Leu Ser Lys Thr Ser
                325                 330                 335

Leu Ala Pro Ile Ile Val Tyr Ile Lys Ile Thr Ser Pro Lys Val Leu
            340                 345                 350

Gln Arg Leu Ile Lys Ser Arg Gly Lys Ser Gln Ser Lys His Leu Asn
        355                 360                 365

Val Gln Ile Ala Ala Ser Glu Lys Leu Ala Gln Cys Pro Pro Glu Met
    370                 375                 380

Phe Asp Ile Ile Leu Asp Glu Asn Gln Leu Glu Asp Ala Cys Glu His
385                 390                 395                 400

Leu Ala Glu Tyr Leu Glu Ala Tyr Trp Lys Ala Thr His Pro Pro Ser
                405                 410                 415

Ser Thr Pro Pro Asn Pro Leu Leu Asn Arg Thr Met Ala Thr Ala Ala
            420                 425                 430

Leu Ala Ala Ser Pro Ala Pro Val Ser Asn Leu Gln Gly Pro Tyr Leu
        435                 440                 445

Ala Ser Gly Asp Gln Pro Leu Glu Arg Ala Thr Gly Glu His Ala Ser
    450                 455                 460

Met His Glu Tyr Pro Gly Glu Leu Gly Gln Pro Gly Leu Tyr Pro
465                 470                 475                 480

Ser Ser His Pro Pro Gly Arg Ala Gly Thr Leu Arg Ala Leu Ser Arg
                485                 490                 495

Gln Asp Thr Phe Asp Ala Asp Thr Pro Gly Ser Arg Asn Ser Ala Tyr
            500                 505                 510

Thr Glu Leu Gly Asp Ser Cys Val Asp Met Glu Thr Asp Pro Ser Glu
        515                 520                 525

Gly Pro Gly Leu Gly Asp Pro Ala Gly Gly Thr Pro Pro Ala Arg
530                 535                 540

Gln Gly Ser Trp Glu Asp Glu Glu Asp Tyr Glu Glu Leu Thr
545                 550                 555                 560

Asp Asn Arg Asn Arg Gly Arg Asn Lys Ala Arg Tyr Cys Ala Glu Gly
                565                 570                 575

Gly Gly Pro Val Leu Gly Arg Asn Lys Asn Glu Leu Glu Gly Trp Gly
            580                 585                 590

Arg Gly Val Tyr Ile Arg
        595

<210> SEQ ID NO 29
<211> LENGTH: 134
<212> TYPE: PRT
<213> ORGANISM: Homo sapiens

<400> SEQUENCE: 29

Met Asp Phe Val Met Lys Gln Ala Leu Gly Gly Ala Thr Lys Asp Met

-continued

```
              1               5              10              15
            Gly Lys Met Leu Gly Gly Glu Glu Lys Asp Pro Asp Ala Gln Lys
                             20                  25                  30

Lys Glu Glu Glu Arg Gln Glu Ala Leu Arg Gln Gln Glu Glu Arg
                             35                  40                  45

Lys Ala Lys His Ala Arg Met Glu Ala Glu Arg Glu Lys Val Arg Gln
                 50                      55                  60

Gln Ile Arg Asp Lys Tyr Gly Leu Lys Lys Glu Glu Lys Glu Ala
             65                  70                  75                  80

Glu Glu Lys Ala Ala Leu Glu Gln Pro Cys Glu Gly Ser Leu Thr Arg
                             85                  90                  95

Pro Lys Lys Ala Ile Pro Ala Gly Cys Gly Asp Glu Glu Glu Glu
                             100                 105                 110

Glu Glu Ser Ile Leu Asp Thr Val Leu Lys Tyr Leu Pro Gly Pro Leu
                             115                 120                 125

Gln Asp Met Phe Lys Lys
                             130
```

<210> SEQ ID NO 30
<211> LENGTH: 512
<212> TYPE: PRT
<213> ORGANISM: Homo sapiens

<400> SEQUENCE: 30

```
            Met Thr Ala Pro Trp Val Ala Leu Ala Leu Leu Trp Gly Ser Leu Trp
             1               5                  10                  15

Pro Gly Ser Gly Arg Gly Glu Ala Glu Thr Arg Glu Cys Ile Tyr Tyr
                             20                  25                  30

Asn Ala Asn Trp Glu Leu Glu Arg Thr Asn Gln Ser Gly Leu Glu Arg
                             35                  40                  45

Cys Glu Gly Glu Gln Asp Lys Arg Leu His Cys Tyr Ala Ser Trp Ala
                 50                      55                  60

Asn Ser Ser Gly Thr Ile Glu Leu Val Lys Lys Gly Cys Trp Leu Asp
             65                  70                  75                  80

Asp Phe Asn Cys Tyr Asp Arg Gln Glu Cys Val Ala Thr Glu Glu Asn
                             85                  90                  95

Pro Gln Val Tyr Phe Cys Cys Cys Glu Gly Asn Phe Cys Asn Glu Arg
                             100                 105                 110

Phe Thr His Leu Pro Glu Ala Gly Gly Pro Glu Val Thr Tyr Glu Pro
                             115                 120                 125

Pro Pro Thr Ala Pro Thr Leu Leu Thr Val Leu Ala Tyr Ser Leu Leu
                 130                     135                 140

Pro Ile Gly Gly Leu Ser Leu Ile Val Leu Leu Ala Phe Trp Met Tyr
            145                  150                 155                 160

Arg His Arg Lys Pro Pro Tyr Gly His Val Asp Ile His Glu Asp Pro
                             165                 170                 175

Gly Pro Pro Pro Pro Ser Pro Leu Val Gly Leu Lys Pro Leu Gln Leu
                             180                 185                 190

Leu Glu Ile Lys Ala Arg Gly Arg Phe Gly Cys Val Trp Lys Ala Gln
                             195                 200                 205

Leu Met Asn Asp Phe Val Ala Val Lys Ile Phe Pro Leu Gln Asp Lys
                 210                     215                 220

Gln Ser Trp Gln Ser Glu Arg Glu Ile Phe Ser Thr Pro Gly Met Lys
            225                  230                 235                 240
```

```
His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Leu Gln Glu Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 31
<211> LENGTH: 206
<212> TYPE: PRT
<213> ORGANISM: Homo sapiens

<400> SEQUENCE: 31

Ser Lys Cys Pro Lys Cys Asp Lys Thr Val Tyr Phe Ala Glu Lys Val
1               5                   10                  15

Ser Ser Leu Gly Lys Asp Trp His Lys Phe Cys Leu Lys Cys Glu Arg
            20                  25                  30

Cys Ser Lys Thr Leu Thr Pro Gly Gly His Ala Glu His Asp Gly Lys
        35                  40                  45

Pro Phe Cys His Lys Pro Cys Tyr Ala Thr Leu Phe Gly Pro Lys Gly
    50                  55                  60

Val Asn Ile Gly Gly Ala Gly Ser Tyr Ile Tyr Glu Lys Pro Leu Ala
65                  70                  75                  80

Glu Gly Pro Gln Val Thr Gly Pro Ile Glu Val Pro Ala Ala Arg Ala
                85                  90                  95

Glu Glu Arg Lys Ala Ser Gly Pro Pro Lys Gly Pro Ser Arg Ala Ser
            100                 105                 110
```

Ser Val Thr Thr Phe Thr Gly Glu Pro Asn Thr Cys Pro Arg Cys Ser
            115                 120                 125

Lys Lys Val Tyr Phe Ala Glu Lys Val Thr Ser Leu Gly Lys Asp Trp
    130                 135                 140

His Arg Pro Cys Leu Arg Cys Glu Arg Cys Gly Lys Thr Leu Thr Pro
145                 150                 155                 160

Gly Gly His Ala Glu His Asp Gly Gln Pro Tyr Cys His Lys Pro Cys
                165                 170                 175

Tyr Gly Ile Leu Phe Gly Pro Lys Gly Val Asn Thr Gly Ala Val Gly
            180                 185                 190

Ser Tyr Ile Tyr Asp Arg Asp Pro Glu Gly Lys Val Gln Pro
            195                 200                 205

<210> SEQ ID NO 32
<211> LENGTH: 76
<212> TYPE: PRT
<213> ORGANISM: Homo sapiens

<400> SEQUENCE: 32

Met Ala Glu Thr Asp Pro Lys Thr Val Gln Asp Leu Thr Ser Val Val
1               5                   10                  15

Gln Thr Leu Leu Gln Gln Met Gln Asp Lys Phe Gln Thr Met Ser Asp
            20                  25                  30

Gln Ile Ile Gly Arg Ile Asp Asp Met Ser Ser Arg Ile Asp Asp Leu
        35                  40                  45

Glu Lys Asn Ile Ala Asp Leu Met Thr Gln Ala Gly Val Glu Glu Leu
    50                  55                  60

Glu Ser Glu Asn Lys Ile Pro Ala Thr Gln Lys Ser
65                  70                  75

<210> SEQ ID NO 33
<211> LENGTH: 672
<212> TYPE: PRT
<213> ORGANISM: Homo sapiens

<400> SEQUENCE: 33

Met Ala Asp Val Phe Pro Gly Asn Asp Ser Thr Ala Ser Gln Asp Val
1               5                   10                  15

Ala Asn Arg Phe Ala Arg Lys Gly Ala Leu Arg Gln Lys Asn Val His
            20                  25                  30

Glu Val Lys Asp His Lys Phe Ile Ala Arg Phe Phe Lys Gln Pro Thr
        35                  40                  45

Phe Cys Ser His Cys Thr Asp Phe Ile Trp Gly Phe Gly Lys Gln Gly
    50                  55                  60

Phe Gln Cys Gln Val Cys Cys Phe Val Val His Lys Arg Cys His Glu
65                  70                  75                  80

Phe Val Thr Phe Ser Cys Pro Gly Ala Asp Lys Gly Pro Asp Thr Asp
            85                  90                  95

Asp Pro Arg Ser Lys His Lys Phe Lys Ile His Thr Tyr Gly Ser Pro
            100                 105                 110

Thr Phe Cys Asp His Cys Gly Ser Leu Leu Tyr Gly Leu Ile His Gln
            115                 120                 125

Gly Met Lys Cys Asp Thr Cys Asp Met Asn Val His Lys Gln Cys Val
        130                 135                 140

Ile Asn Val Pro Ser Leu Cys Gly Met Asp His Thr Glu Lys Arg Gly
145                 150                 155                 160

```
Arg Ile Tyr Leu Lys Ala Glu Val Ala Asp Glu Lys Leu His Val Thr
                165                 170                 175

Val Arg Asp Ala Lys Asn Leu Ile Pro Met Asp Pro Asn Gly Leu Ser
            180                 185                 190

Asp Pro Tyr Val Lys Leu Lys Leu Ile Pro Asp Pro Lys Asn Glu Ser
        195                 200                 205

Lys Gln Lys Thr Lys Thr Ile Arg Ser Thr Leu Asn Pro Gln Trp Asn
    210                 215                 220

Glu Ser Phe Thr Phe Lys Leu Lys Pro Ser Asp Lys Asp Arg Arg Leu
225                 230                 235                 240

Ser Val Glu Ile Trp Asp Trp Asp Arg Thr Thr Arg Asn Asp Phe Met
                245                 250                 255

Gly Ser Leu Ser Phe Gly Val Ser Glu Leu Met Lys Met Pro Ala Ser
            260                 265                 270

Gly Trp Tyr Lys Leu Leu Asn Gln Glu Glu Gly Glu Tyr Tyr Asn Val
        275                 280                 285

Pro Ile Pro Glu Gly Asp Glu Gly Asn Met Glu Leu Arg Gln Lys
    290                 295                 300

Phe Glu Lys Ala Lys Leu Gly Pro Ala Gly Asn Lys Val Ile Ser Pro
305                 310                 315                 320

Ser Glu Asp Arg Lys Gln Pro Ser Asn Asn Leu Asp Arg Val Lys Leu
                325                 330                 335

Thr Asp Phe Asn Phe Leu Met Val Leu Gly Lys Gly Ser Phe Gly Lys
            340                 345                 350

Val Met Leu Ala Asp Arg Lys Gly Thr Glu Glu Leu Tyr Ala Ile Lys
        355                 360                 365

Ile Leu Lys Lys Asp Val Val Ile Gln Asp Asp Val Glu Cys Thr
    370                 375                 380

Met Val Glu Lys Arg Val Leu Ala Leu Leu Asp Lys Pro Pro Phe Leu
385                 390                 395                 400

Thr Gln Leu His Ser Cys Phe Gln Thr Val Asp Arg Leu Tyr Phe Val
                405                 410                 415

Met Glu Tyr Val Asn Gly Gly Asp Leu Met Tyr His Ile Gln Gln Val
            420                 425                 430

Gly Lys Phe Lys Glu Pro Gln Ala Val Phe Tyr Ala Ala Glu Ile Ser
        435                 440                 445

Ile Gly Leu Phe Phe Leu His Lys Arg Gly Ile Ile Tyr Arg Asp Leu
    450                 455                 460

Lys Leu Asp Asn Val Met Leu Asp Ser Glu Gly His Ile Lys Ile Ala
465                 470                 475                 480

Asp Phe Gly Met Cys Lys Glu His Met Met Asp Gly Val Thr Thr Arg
                485                 490                 495

Thr Phe Cys Gly Thr Pro Asp Tyr Ile Ala Pro Glu Ile Ile Ala Tyr
            500                 505                 510

Gln Pro Tyr Gly Lys Ser Val Asp Trp Trp Ala Tyr Gly Val Leu Leu
        515                 520                 525

Tyr Glu Met Leu Ala Gly Gln Pro Pro Phe Asp Gly Glu Asp Glu Asp
530                 535                 540

Glu Leu Phe Gln Ser Ile Met Glu His Asn Val Ser Tyr Pro Lys Ser
545                 550                 555                 560

Leu Ser Lys Glu Ala Val Ser Ile Cys Lys Gly Leu Met Thr Lys His
                565                 570                 575
```

-continued

```
Pro Ala Lys Arg Leu Gly Cys Gly Pro Glu Gly Glu Arg Asp Val Arg
                580                 585                 590

Glu His Ala Phe Phe Arg Arg Ile Asp Trp Glu Lys Leu Glu Asn Arg
            595                 600                 605

Glu Ile Gln Pro Pro Phe Lys Pro Lys Val Cys Gly Lys Gly Ala Glu
        610                 615                 620

Asn Phe Asp Lys Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
                645                 650                 655

Ser Tyr Val Asn Pro Gln Phe Val His Pro Ile Leu Gln Ser Ala Val
            660                 665                 670
```

<210> SEQ ID NO 34
<211> LENGTH: 596
<212> TYPE: PRT
<213> ORGANISM: Homo sapiens

<400> SEQUENCE: 34

```
Met Pro Thr Gln Arg Asp Ser Ser Thr Met Ser His Thr Val Ala Gly
1               5                   10                  15

Gly Gly Ser Gly Asp His Ser His Gln Val Arg Val Lys Ala Tyr Tyr
            20                  25                  30

Arg Gly Asp Ile Met Ile Thr His Phe Glu Pro Ser Ile Ser Phe Glu
        35                  40                  45

Gly Leu Cys Asn Glu Val Arg Asp Met Cys Ser Phe Asp Asn Glu Gln
    50                  55                  60

Leu Phe Thr Met Lys Trp Ile Asp Glu Glu Gly Asp Pro Cys Thr Val
65                  70                  75                  80

Ser Ser Gln Leu Glu Leu Glu Glu Ala Phe Arg Leu Tyr Glu Leu Asn
                85                  90                  95

Lys Asp Ser Glu Leu Leu Ile His Val Phe Pro Cys Val Pro Glu Arg
            100                 105                 110

Pro Gly Met Pro Cys Pro Gly Glu Asp Lys Ser Ile Tyr Arg Arg Gly
        115                 120                 125

Ala Arg Arg Trp Arg Lys Leu Tyr Cys Ala Asn Gly His Thr Phe Gln
    130                 135                 140

Ala Lys Arg Phe Asn Arg Arg Ala His Cys Ala Ile Cys Thr Asp Arg
145                 150                 155                 160

Ile Trp Gly Leu Gly Arg Gln Gly Tyr Lys Cys Ile Asn Cys Lys Leu
                165                 170                 175

Leu Val His Lys Lys Cys His Lys Leu Val Thr Ile Glu Cys Gly Arg
            180                 185                 190

His Ser Leu Pro Gln Glu Pro Val Met Pro Met Asp Gln Ser Ser Met
        195                 200                 205

His Ser Asp His Ala Gln Thr Val Ile Pro Tyr Asn Pro Ser Ser His
    210                 215                 220

Glu Ser Leu Asp Gln Val Gly Glu Glu Lys Glu Ala Met Asn Thr Arg
225                 230                 235                 240

Glu Ser Gly Lys Ala Ser Ser Ser Leu Gly Leu Gln Asp Phe Asp Leu
                245                 250                 255

Leu Arg Val Ile Gly Arg Gly Ser Tyr Ala Lys Val Leu Leu Val Arg
            260                 265                 270

Leu Lys Lys Thr Asp Arg Ile Tyr Ala Met Lys Val Val Lys Lys Glu
        275                 280                 285
```

Leu Val Asn Asp Asp Glu Asp Ile Asp Trp Val Gln Thr Glu Lys His
        290                 295                 300

Val Phe Glu Gln Ala Ser Asn His Pro Phe Leu Val Gly Leu His Ser
305                 310                 315                 320

Cys Phe Gln Thr Glu Ser Arg Leu Phe Phe Val Ile Glu Tyr Val Asn
                325                 330                 335

Gly Gly Asp Leu Met Phe His Met Gln Arg Gln Arg Lys Leu Pro Glu
            340                 345                 350

Glu His Ala Arg Phe Tyr Ser Ala Glu Ile Ser Leu Ala Leu Asn Tyr
        355                 360                 365

Leu His Glu Arg Gly Ile Ile Tyr Arg Asp Leu Lys Leu Asp Asn Val
    370                 375                 380

Leu Leu Asp Ser Glu Gly His Ile Lys Leu Thr Asp Tyr Gly Met Cys
385                 390                 395                 400

Lys Glu Gly Leu Arg Pro Gly Asp Thr Thr Ser Thr Phe Cys Gly Thr
                405                 410                 415

Pro Asn Tyr Ile Ala Pro Glu Ile Leu Arg Gly Glu Asp Tyr Gly Phe
            420                 425                 430

Ser Val Asp Trp Trp Ala Leu Gly Val Leu Met Phe Glu Met Met Ala
        435                 440                 445

Gly Arg Ser Pro Phe Asp Ile Val Gly Ser Ser Asp Asn Pro Asp Gln
    450                 455                 460

Asn Thr Glu Asp Tyr Leu Phe Gln Val Ile Leu Glu Lys Gln Ile Arg
465                 470                 475                 480

Ile Pro Arg Ser Leu Ser Val Lys Ala Ala Ser Val Leu Lys Ser Phe
                485                 490                 495

Leu Asn Lys Asp Pro Lys Glu Arg Leu Gly Cys His Pro Gln Thr Gly
            500                 505                 510

Phe Ala Asp Ile Gln Gly His Pro Phe Phe Arg Asn Val Asp Trp Asp
        515                 520                 525

Met Met Glu Gln Lys Gln Val Val Pro Pro Phe Lys Pro Asn Ile Ser
    530                 535                 540

Gly Glu Phe Gly Leu Asp Asn Phe Asp Ser Gln Phe Thr Asn Glu Pro
545                 550                 555                 560

Val Gln Leu Thr Pro Asp Asp Asp Ile Val Arg Lys Ile Asp Gln
                565                 570                 575

Ser Glu Phe Glu Gly Phe Glu Tyr Ile Asn Pro Leu Leu Met Ser Ala
            580                 585                 590

Glu Glu Cys Val
        595

<210> SEQ ID NO 35
<211> LENGTH: 592
<212> TYPE: PRT
<213> ORGANISM: Homo sapiens

<400> SEQUENCE: 35

Met Pro Ser Arg Thr Gly Pro Lys Met Glu Gly Ser Gly Gly Arg Val
1               5                   10                  15

Arg Leu Lys Ala His Tyr Gly Gly Asp Ile Phe Ile Thr Ser Val Asp
            20                  25                  30

Ala Ala Thr Thr Phe Glu Glu Leu Cys Glu Glu Val Arg Asp Met Cys
        35                  40                  45

Arg Leu His Gln Gln His Pro Leu Thr Leu Lys Trp Val Asp Ser Glu

-continued

```
                50                  55                  60
Gly Asp Pro Cys Thr Val Ser Ser Gln Met Glu Leu Glu Ala Phe
 65                  70                  75                  80

Arg Leu Ala Arg Gln Cys Arg Asp Glu Gly Leu Ile Ile His Val Phe
                 85                  90                  95

Pro Ser Thr Pro Glu Gln Pro Gly Leu Pro Cys Pro Gly Glu Asp Lys
                100                 105                 110

Ser Ile Tyr Arg Arg Gly Ala Arg Arg Trp Arg Lys Leu Tyr Arg Ala
                115                 120                 125

Asn Gly His Leu Phe Gln Ala Lys Arg Phe Asn Arg Arg Ala Tyr Cys
                130                 135                 140

Gly Gln Cys Ser Glu Arg Ile Trp Gly Leu Ala Arg Gln Gly Tyr Arg
145                 150                 155                 160

Cys Ile Asn Cys Lys Leu Leu Val His Lys Arg Cys His Gly Leu Val
                165                 170                 175

Pro Leu Thr Cys Arg Lys His Met Asp Ser Val Met Pro Ser Gln Glu
                180                 185                 190

Pro Pro Val Asp Asp Lys Asn Glu Asp Ala Asp Leu Pro Ser Glu Glu
                195                 200                 205

Thr Asp Gly Ile Ala Tyr Ile Ser Ser Ser Arg Lys His Asp Ser Ile
210                 215                 220

Lys Asp Asp Ser Glu Asp Leu Lys Pro Val Ile Asp Gly Met Asp Gly
225                 230                 235                 240

Ile Lys Ile Ser Gln Gly Leu Gly Leu Gln Asp Phe Asp Leu Ile Arg
                245                 250                 255

Val Ile Gly Arg Gly Ser Tyr Ala Lys Val Leu Leu Val Arg Leu Lys
                260                 265                 270

Lys Asn Asp Gln Ile Tyr Ala Met Lys Val Val Lys Lys Glu Leu Val
                275                 280                 285

His Asp Asp Glu Asp Ile Asp Trp Val Gln Thr Glu Lys His Val Phe
                290                 295                 300

Glu Gln Ala Ser Ser Asn Pro Phe Leu Val Gly Leu His Ser Cys Phe
305                 310                 315                 320

Gln Thr Thr Ser Arg Leu Phe Leu Val Ile Glu Tyr Val Asn Gly Gly
                325                 330                 335

Asp Leu Met Phe His Met Gln Arg Gln Arg Lys Leu Pro Glu Glu His
                340                 345                 350

Ala Arg Phe Tyr Ala Ala Glu Ile Cys Ile Ala Leu Asn Phe Leu His
                355                 360                 365

Glu Arg Gly Ile Ile Tyr Arg Asp Leu Lys Leu Asp Asn Val Leu Leu
                370                 375                 380

Asp Ala Asp Gly His Ile Lys Leu Thr Asp Tyr Gly Met Cys Lys Glu
385                 390                 395                 400

Gly Leu Gly Pro Gly Asp Thr Thr Ser Thr Phe Cys Gly Thr Pro Asn
                405                 410                 415

Tyr Ile Ala Pro Glu Ile Leu Arg Gly Glu Glu Tyr Gly Phe Ser Val
                420                 425                 430

Asp Trp Trp Ala Leu Gly Val Leu Met Phe Glu Met Met Ala Gly Arg
                435                 440                 445

Ser Pro Phe Asp Ile Ile Thr Asp Asn Pro Asp Met Asn Thr Glu Asp
                450                 455                 460

Tyr Leu Phe Gln Val Ile Leu Glu Lys Pro Ile Arg Ile Pro Arg Phe
465                 470                 475                 480
```

```
Leu Ser Val Lys Ala Ser His Val Leu Lys Gly Phe Leu Asn Lys Asp
                485                 490                 495

Pro Lys Glu Arg Leu Gly Cys Arg Pro Gln Thr Gly Phe Ser Asp Ile
            500                 505                 510

Lys Ser His Ala Phe Phe Arg Ser Ile Asp Trp Asp Leu Leu Glu Lys
        515                 520                 525

Lys Gln Ala Leu Pro Pro Phe Gln Pro Gln Ile Thr Asp Asp Tyr Gly
    530                 535                 540

Leu Asp Asn Phe Asp Thr Gln Phe Thr Ser Glu Pro Val Gln Leu Thr
545                 550                 555                 560

Pro Asp Asp Glu Asp Ala Ile Lys Arg Ile Asp Gln Ser Glu Phe Glu
                565                 570                 575

Gly Phe Glu Tyr Ile Asn Pro Leu Leu Leu Ser Thr Glu Glu Ser Val
            580                 585                 590
```

<210> SEQ ID NO 36
<211> LENGTH: 721
<212> TYPE: PRT
<213> ORGANISM: Homo sapiens

<400> SEQUENCE: 36

```
Met Ala Ala Pro Val Ala Pro Pro Gly Val Val Ser Arg Ala
1               5                   10                  15

Asn Lys Arg Ser Gly Ala Gly Pro Gly Ser Gly Gly Gly Ala
                20                  25                  30

Arg Gly Ala Glu Glu Pro Pro Pro Leu Gln Ala Val Leu Val
            35                  40                  45

Ala Asp Ser Phe Asp Arg Arg Phe Phe Pro Ile Ser Lys Asp Gln Pro
    50                  55                  60

Arg Val Leu Leu Pro Leu Ala Asn Val Ala Leu Ile Asp Tyr Thr Leu
65                  70                  75                  80

Glu Phe Leu Thr Ala Thr Gly Val Gln Glu Thr Phe Val Phe Cys Cys
                85                  90                  95

Trp Lys Ala Ala Gln Ile Lys Glu His Leu Leu Lys Ser Lys Trp Cys
                100                 105                 110

Arg Pro Thr Ser Leu Asn Val Val Arg Ile Ile Thr Ser Glu Leu Tyr
            115                 120                 125

Arg Ser Leu Gly Asp Val Leu Arg Asp Val Asp Ala Lys Ala Leu Val
        130                 135                 140

Arg Ser Asp Phe Leu Leu Val Tyr Gly Asp Val Ile Ser Asn Ile Asn
145                 150                 155                 160

Ile Thr Arg Ala Leu Glu Glu His Arg Leu Arg Arg Lys Leu Glu Lys
                165                 170                 175

Asn Val Ser Val Met Thr Met Ile Phe Lys Glu Ser Ser Pro Ser His
                180                 185                 190

Pro Thr Arg Cys His Glu Asp Asn Val Val Ala Val Asp Ser Thr
            195                 200                 205

Thr Asn Arg Val Leu His Phe Gln Lys Thr Gln Gly Leu Arg Arg Phe
        210                 215                 220

Ala Phe Pro Leu Ser Leu Phe Gln Gly Ser Asp Gly Val Glu Val
225                 230                 235                 240

Arg Tyr Asp Leu Leu Asp Cys His Ile Ser Ile Cys Ser Pro Gln Val
                245                 250                 255

Ala Gln Leu Phe Thr Asp Asn Phe Asp Tyr Gln Thr Arg Asp Asp Phe
```

```
                    260                 265                 270
Val Arg Gly Leu Leu Val Asn Glu Glu Ile Leu Gly Asn Gln Ile His
            275                 280                 285
Met His Val Thr Ala Lys Glu Tyr Gly Ala Arg Val Ser Asn Leu His
            290                 295                 300
Met Tyr Ser Ala Val Cys Ala Asp Val Ile Arg Arg Trp Val Tyr Pro
305                 310                 315                 320
Leu Thr Pro Glu Ala Asn Phe Thr Asp Ser Thr Thr Gln Ser Cys Thr
                325                 330                 335
His Ser Arg His Asn Ile Tyr Arg Gly Pro Glu Val Ser Leu Gly His
            340                 345                 350
Gly Ser Ile Leu Glu Glu Asn Val Leu Leu Gly Ser Gly Thr Val Ile
            355                 360                 365
Gly Ser Asn Cys Phe Ile Thr Asn Ser Val Ile Gly Pro Gly Cys His
            370                 375                 380
Ile Gly Asp Asn Val Val Leu Asp Gln Thr Tyr Leu Trp Gln Gly Val
385                 390                 395                 400
Arg Val Ala Ala Gly Ala Gln Ile His Gln Ser Leu Leu Cys Asp Asn
                405                 410                 415
Ala Glu Val Lys Glu Arg Val Thr Leu Lys Pro Arg Ser Val Leu Thr
            420                 425                 430
Ser Gln Val Val Val Gly Pro Asn Ile Thr Leu Pro Glu Gly Ser Val
            435                 440                 445
Ile Ser Leu His Pro Pro Asp Ala Glu Glu Asp Glu Asp Gly Glu
450                 455                 460
Phe Ser Asp Asp Ser Gly Ala Asp Gln Glu Lys Asp Lys Val Lys Met
465                 470                 475                 480
Lys Gly Tyr Asn Pro Ala Glu Val Gly Ala Ala Gly Lys Gly Tyr Leu
                485                 490                 495
Trp Lys Ala Ala Gly Met Asn Met Glu Glu Glu Glu Leu Gln Gln
            500                 505                 510
Asn Leu Trp Gly Leu Lys Ile Asn Met Glu Glu Glu Ser Glu Ser Glu
            515                 520                 525
Ser Glu Gln Ser Met Asp Ser Glu Glu Pro Asp Ser Arg Gly Gly Ser
            530                 535                 540
Pro Gln Met Asp Asp Ile Lys Val Phe Gln Asn Glu Val Leu Gly Thr
545                 550                 555                 560
Leu Gln Arg Gly Lys Glu Glu Asn Ile Ser Cys Asp Asn Leu Val Leu
                565                 570                 575
Glu Ile Asn Ser Leu Lys Tyr Ala Tyr Asn Val Ser Leu Lys Glu Val
            580                 585                 590
Met Gln Val Leu Ser His Val Val Leu Glu Phe Pro Leu Gln Gln Met
            595                 600                 605
Asp Ser Pro Leu Asp Ser Ser Arg Tyr Cys Ala Leu Leu Leu Pro Leu
            610                 615                 620
Leu Lys Ala Trp Ser Pro Val Phe Arg Asn Tyr Ile Lys Arg Ala Ala
625                 630                 635                 640
Asp His Leu Glu Ala Leu Ala Ala Ile Glu Asp Phe Phe Leu Glu His
                645                 650                 655
Glu Ala Leu Gly Ile Ser Met Ala Lys Val Leu Met Ala Phe Tyr Gln
            660                 665                 670
Leu Glu Ile Leu Ala Glu Glu Thr Ile Leu Ser Trp Phe Ser Gln Arg
            675                 680                 685
```

```
Asp Thr Thr Asp Lys Gly Gln Gln Leu Arg Lys Asn Gln Gln Leu Gln
    690                 695                 700

Arg Phe Ile Gln Trp Leu Lys Glu Ala Glu Glu Ser Ser Glu Asp
705                 710                 715                 720

Asp
```

<210> SEQ ID NO 37
<211> LENGTH: 143
<212> TYPE: PRT
<213> ORGANISM: Homo sapiens

<400> SEQUENCE: 37

```
Met Pro Lys Val Lys Arg Ser Arg Lys Ala Pro Asp Gly Trp Glu
1               5                   10                  15

Leu Ile Glu Pro Thr Leu Asp Glu Leu Asp Gln Lys Met Arg Glu Ala
                20                  25                  30

Glu Thr Glu Pro His Glu Gly Lys Arg Lys Val Glu Ser Leu Trp Pro
            35                  40                  45

Ile Phe Arg Ile His His Gln Lys Thr Arg Tyr Ile Phe Asp Leu Phe
    50                  55                  60

Tyr Lys Arg Lys Ala Ile Ser Arg Glu Leu Tyr Glu Tyr Cys Ile Lys
65                  70                  75                  80

Glu Gly Tyr Ala Asp Lys Asn Leu Ile Ala Lys Trp Lys Lys Gln Gly
                85                  90                  95

Tyr Glu Asn Leu Cys Cys Leu Arg Cys Ile Gln Thr Arg Asp Thr Asn
            100                 105                 110

Phe Gly Thr Asn Cys Ile Cys Arg Val Pro Lys Ser Lys Leu Glu Val
        115                 120                 125

Gly Arg Ile Ile Glu Cys Thr His Cys Gly Cys Arg Gly Cys Ser
    130                 135                 140
```

<210> SEQ ID NO 38
<211> LENGTH: 198
<212> TYPE: PRT
<213> ORGANISM: Homo sapiens

<400> SEQUENCE: 38

```
Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
                20                  25                  30

Phe Gly Pro Val Asp His Glu Glu Leu Thr Arg Asp Leu Glu Lys His
            35                  40                  45

Cys Arg Asp Met Glu Glu Ala Ser Gln Arg Lys Trp Asn Phe Asp Phe
    50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
    130                 135                 140
```

```
Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
            195

<210> SEQ ID NO 39
<211> LENGTH: 102
<212> TYPE: PRT
<213> ORGANISM: Homo sapiens

<400> SEQUENCE: 39

Met Ser Ser Pro Pro Glu Gly Lys Leu Glu Thr Lys Ala Gly His Pro
1               5                   10                  15

Pro Ala Val Lys Ala Gly Gly Met Arg Ile Val Gln Lys His Pro His
                20                  25                  30

Thr Gly Asp Thr Lys Glu Glu Lys Asp Lys Asp Gln Glu Trp Glu
            35                  40                  45

Ser Pro Ser Pro Lys Pro Thr Val Phe Ile Ser Gly Val Ile Ala
50                  55                  60

Arg Gly Asp Lys Asp Phe Pro Pro Ala Ala Gln Val Ala His Gln
65                  70                  75                  80

Lys Pro His Ala Ser Met Asp Lys His Pro Ser Pro Arg Thr Gln His
                85                  90                  95

Ile Gln Gln Pro Arg Lys
            100

<210> SEQ ID NO 40
<211> LENGTH: 369
<212> TYPE: PRT
<213> ORGANISM: Homo sapiens

<400> SEQUENCE: 40

Met Pro Val Val Thr Thr Asp Ala Glu Ser Glu Thr Gly Ile Pro Lys
1               5                   10                  15

Ser Leu Ser Asn Glu Pro Pro Ser Glu Thr Met Glu Glu Ile Glu His
                20                  25                  30

Thr Cys Pro Gln Pro Arg Leu Thr Leu Thr Ala Pro Ala Pro Phe Ala
            35                  40                  45

Asp Glu Thr Asn Cys Gln Cys Gln Ala Pro His Glu Lys Leu Thr Ile
50                  55                  60

Ala Gln Ala Arg Leu Gly Thr Pro Ala Asp Arg Pro Val Arg Val Tyr
65                  70                  75                  80

Ala Asp Gly Ile Phe Asp Leu Phe His Ser Gly His Ala Arg Ala Leu
                85                  90                  95

Met Gln Ala Lys Thr Leu Phe Pro Asn Ser Tyr Leu Leu Val Gly Val
            100                 105                 110

Cys Ser Asp Asp Leu Thr His Lys Phe Lys Gly Phe Thr Val Met Asn
        115                 120                 125

Glu Ala Glu Arg Tyr Glu Ala Leu Arg His Cys Arg Tyr Val Asp Glu
        130                 135                 140

Val Ile Arg Asp Ala Pro Trp Thr Leu Thr Pro Glu Phe Leu Glu Lys
145                 150                 155                 160
```

```
His Lys Ile Asp Phe Val Ala His Asp Asp Ile Pro Tyr Ser Ser Ala
                165                 170                 175
Gly Ser Asp Asp Val Tyr Lys His Ile Lys Glu Ala Gly Met Phe Val
            180                 185                 190
Pro Thr Gln Arg Thr Glu Gly Ile Ser Thr Ser Asp Ile Ile Thr Arg
        195                 200                 205
Ile Val Arg Asp Tyr Asp Val Tyr Ala Arg Arg Asn Leu Gln Arg Gly
    210                 215                 220
Tyr Thr Ala Lys Glu Leu Asn Val Ser Phe Ile Asn Glu Lys Arg Tyr
225                 230                 235                 240
Arg Phe Gln Asn Gln Val Asp Lys Met Lys Glu Lys Val Lys Asn Val
                245                 250                 255
Glu Glu Arg Ser Lys Glu Phe Val Asn Arg Val Glu Glu Lys Ser His
            260                 265                 270
Asp Leu Ile Gln Lys Trp Glu Lys Ser Arg Glu Phe Ile Gly Asn
        275                 280                 285
Phe Leu Glu Leu Phe Gly Pro Asp Gly Ala Trp Lys Gln Met Phe Gln
    290                 295                 300
Glu Arg Ser Ser Arg Met Leu Gln Ala Leu Ser Pro Lys Gln Ser Pro
305                 310                 315                 320
Val Ser Ser Pro Thr Arg Ser Arg Ser Pro Ser Arg Ser Pro Ser Pro
                325                 330                 335
Thr Phe Ser Trp Leu Pro Leu Lys Thr Ser Pro Pro Ser Ser Pro Lys
            340                 345                 350
Ala Ala Ser Ala Ser Ile Ser Ser Met Ser Glu Gly Asp Glu Asp Glu
        355                 360                 365
Lys

<210> SEQ ID NO 41
<211> LENGTH: 100
<212> TYPE: PRT
<213> ORGANISM: Homo sapiens

<400> SEQUENCE: 41

Met Pro Lys Arg Lys Val Ser Ser Ala Glu Gly Ala Ala Lys Glu Glu
1               5                   10                  15
Pro Lys Arg Arg Ser Ala Arg Leu Ser Ala Lys Pro Ala Lys Val
            20                  25                  30
Glu Ala Lys Pro Lys Lys Ala Ala Ala Lys Asp Lys Ser Ser Asp Lys
        35                  40                  45
Lys Val Gln Thr Lys Gly Lys Arg Gly Ala Lys Gly Lys Gln Ala Glu
    50                  55                  60
Val Ala Asn Gln Glu Thr Lys Glu Asp Leu Pro Ala Glu Asn Gly Glu
65                  70                  75                  80
Thr Lys Thr Glu Glu Ser Pro Ala Ser Asp Glu Ala Gly Glu Lys Glu
                85                  90                  95
Ala Lys Ser Asp
            100

<210> SEQ ID NO 42
<211> LENGTH: 603
<212> TYPE: PRT
<213> ORGANISM: Homo sapiens

<400> SEQUENCE: 42

Met Ser Ala Ala Val Thr Ala Gly Lys Leu Ala Arg Ala Pro Ala Asp
```

-continued

```
  1               5              10              15
Pro Gly Lys Ala Gly Val Pro Gly Val Ala Ala Pro Gly Ala Pro Ala
                 20              25              30

Ala Ala Pro Ala Lys Glu Ile Pro Glu Val Leu Val Asp Pro Arg
             35              40              45

Ser Arg Arg Tyr Val Arg Gly Arg Phe Leu Lys Gly Gly Phe
 50              55              60

Ala Lys Cys Phe Glu Ile Ser Asp Ala Asp Thr Lys Glu Val Phe Ala
 65              70              75              80

Gly Lys Ile Val Pro Lys Ser Leu Leu Leu Lys Pro His Gln Arg Glu
                 85              90              95

Lys Met Ser Met Glu Ile Ser Ile His Arg Ser Leu Ala His Gln His
                100             105             110

Val Val Gly Phe His Gly Phe Phe Glu Asp Asn Asp Phe Val Phe Val
                115             120             125

Val Leu Glu Leu Cys Arg Arg Arg Ser Leu Leu Glu Leu His Lys Arg
                130             135             140

Arg Lys Ala Leu Thr Glu Pro Glu Ala Arg Tyr Tyr Leu Arg Gln Ile
145             150             155             160

Val Leu Gly Cys Gln Tyr Leu His Arg Asn Arg Val Ile His Arg Asp
                165             170             175

Leu Lys Leu Gly Asn Leu Phe Leu Asn Glu Asp Leu Glu Val Lys Ile
                180             185             190

Gly Asp Phe Gly Leu Ala Thr Lys Val Glu Tyr Asp Gly Glu Arg Lys
                195             200             205

Lys Thr Leu Cys Gly Thr Pro Asn Tyr Ile Ala Pro Glu Val Leu Ser
                210             215             220

Lys Lys Gly His Ser Phe Glu Val Asp Val Trp Ser Ile Gly Cys Ile
225             230             235             240

Met Tyr Thr Leu Leu Val Gly Lys Pro Pro Phe Glu Thr Ser Cys Leu
                245             250             255

Lys Glu Thr Tyr Leu Arg Ile Lys Lys Asn Glu Tyr Ser Ile Pro Lys
                260             265             270

His Ile Asn Pro Val Ala Ala Ser Leu Ile Gln Lys Met Leu Gln Thr
                275             280             285

Asp Pro Thr Ala Arg Pro Thr Ile Asn Glu Leu Leu Asn Asp Glu Phe
                290             295             300

Phe Thr Ser Gly Tyr Ile Pro Ala Arg Leu Pro Ile Thr Cys Leu Thr
305             310             315             320

Ile Pro Pro Arg Phe Ser Ile Ala Pro Ser Ser Leu Asp Pro Ser Asn
                325             330             335

Arg Lys Pro Leu Thr Val Leu Asn Lys Gly Leu Glu Asn Pro Leu Pro
                340             345             350

Glu Arg Pro Arg Glu Lys Glu Pro Val Val Arg Glu Thr Gly Glu
                355             360             365

Val Val Asp Cys His Leu Ser Asp Met Leu Gln Gln Leu His Ser Val
                370             375             380

Asn Ala Ser Lys Pro Ser Glu Arg Gly Leu Val Arg Gln Glu Glu Ala
385             390             395             400

Glu Asp Pro Ala Cys Ile Pro Ile Phe Trp Val Ser Lys Trp Val Asp
                405             410             415

Tyr Ser Asp Lys Tyr Gly Leu Gly Tyr Gln Leu Cys Asp Asn Ser Val
                420             425             430
```

```
Gly Val Leu Phe Asn Asp Ser Thr Arg Leu Ile Leu Tyr Asn Asp Gly
            435                 440                 445

Asp Ser Leu Gln Tyr Ile Glu Arg Asp Gly Thr Glu Ser Tyr Leu Thr
    450                 455                 460

Val Ser Ser His Pro Asn Ser Leu Met Lys Lys Ile Thr Leu Leu Lys
465                 470                 475                 480

Tyr Phe Arg Asn Tyr Met Ser Glu His Leu Leu Lys Ala Gly Ala Asn
                485                 490                 495

Ile Thr Pro Arg Glu Gly Asp Glu Leu Ala Arg Leu Pro Tyr Leu Arg
                500                 505                 510

Thr Trp Phe Arg Thr Arg Ser Ala Ile Ile Leu His Leu Ser Asn Gly
            515                 520                 525

Ser Val Gln Ile Asn Phe Phe Gln Asp His Thr Lys Leu Ile Leu Cys
    530                 535                 540

Pro Leu Met Ala Ala Val Thr Tyr Ile Asp Glu Lys Arg Asp Phe Arg
545                 550                 555                 560

Thr Tyr Arg Leu Ser Leu Leu Glu Glu Tyr Gly Cys Cys Lys Glu Leu
                565                 570                 575

Ala Ser Arg Leu Arg Tyr Ala Arg Thr Met Val Asp Lys Leu Leu Ser
                580                 585                 590

Ser Arg Ser Ala Ser Asn Arg Leu Lys Ala Ser
            595                 600

<210> SEQ ID NO 43
<211> LENGTH: 822
<212> TYPE: PRT
<213> ORGANISM: Homo sapiens

<400> SEQUENCE: 43

Met Gly Phe Gly Ser Asp Leu Lys Asn Ser His Glu Ala Val Leu Lys
1               5                   10                  15

Leu Gln Asp Trp Glu Leu Arg Leu Leu Glu Thr Val Lys Lys Phe Met
            20                  25                  30

Ala Leu Arg Ile Lys Ser Asp Lys Glu Tyr Ala Ser Thr Leu Gln Asn
        35                  40                  45

Leu Cys Asn Gln Val Asp Lys Glu Ser Thr Val Gln Met Asn Tyr Val
    50                  55                  60

Ser Asn Val Ser Lys Ser Trp Leu Leu Met Ile Gln Gln Thr Glu Gln
65                  70                  75                  80

Leu Ser Arg Ile Met Lys Thr His Ala Glu Asp Leu Asn Ser Gly Pro
                85                  90                  95

Leu His Arg Leu Thr Met Met Ile Lys Asp Lys Gln Gln Val Lys Lys
            100                 105                 110

Ser Tyr Ile Gly Val His Gln Gln Ile Glu Ala Glu Met Ile Lys Val
        115                 120                 125

Thr Lys Thr Glu Leu Glu Lys Leu Lys Cys Ser Tyr Arg Gln Leu Ile
    130                 135                 140

Lys Glu Met Asn Ser Ala Lys Glu Lys Tyr Lys Glu Ala Leu Ala Lys
145                 150                 155                 160

Gly Lys Glu Thr Glu Lys Ala Lys Glu Arg Tyr Asp Lys Ala Thr Met
                165                 170                 175

Lys Leu His Met Leu His Asn Gln Tyr Val Leu Ala Leu Lys Gly Ala
            180                 185                 190

Gln Leu His Gln Asn Gln Tyr Tyr Asp Ile Thr Leu Pro Leu Leu Leu
```

```
                195                 200                 205
Asp Ser Leu Gln Lys Met Gln Glu Met Ile Lys Ala Leu Lys Gly
210                 215                 220

Ile Phe Asp Glu Tyr Ser Gln Ile Thr Ser Leu Val Thr Glu Ile
225                 230                 235                 240

Val Asn Val His Lys Glu Ile Gln Met Ser Val Glu Gln Ile Asp Pro
                245                 250                 255

Ser Thr Glu Tyr Asn Asn Phe Ile Asp Val His Arg Thr Thr Ala Ala
                260                 265                 270

Lys Glu Gln Glu Ile Glu Phe Asp Thr Ser Leu Leu Glu Glu Asn Glu
                275                 280                 285

Asn Leu Gln Ala Asn Glu Ile Met Trp Asn Asn Leu Thr Ala Glu Ser
290                 295                 300

Leu Gln Val Met Leu Lys Thr Leu Ala Glu Glu Leu Met Gln Thr Gln
305                 310                 315                 320

Gln Met Leu Leu Asn Lys Glu Glu Ala Val Leu Glu Leu Glu Lys Arg
                325                 330                 335

Ile Glu Glu Ser Ser Glu Thr Cys Glu Lys Lys Ser Asp Ile Val Leu
                340                 345                 350

Leu Leu Ser Gln Lys Gln Ala Leu Glu Glu Leu Lys Gln Ser Val Gln
            355                 360                 365

Gln Leu Arg Cys Thr Glu Ala Lys Phe Ser Ala Gln Lys Glu Leu Leu
370                 375                 380

Glu Gln Lys Val Gln Glu Asn Asp Gly Lys Glu Pro Pro Val Val
385                 390                 395                 400

Asn Tyr Glu Glu Asp Ala Arg Ser Val Thr Ser Met Glu Arg Lys Glu
                405                 410                 415

Arg Leu Ser Lys Phe Glu Ser Ile Arg His Ser Ile Ala Gly Ile Ile
                420                 425                 430

Arg Ser Pro Lys Ser Ala Val Gly Ser Ser Ala Leu Ser Asp Met Ile
            435                 440                 445

Ser Ile Ser Glu Lys Pro Leu Ala Glu Gln Asp Trp Tyr His Gly Ala
450                 455                 460

Ile Pro Arg Ile Glu Ala Gln Glu Leu Leu Lys Lys Gln Gly Asp Phe
465                 470                 475                 480

Leu Val Arg Glu Ser His Gly Lys Pro Gly Glu Tyr Val Leu Ser Val
                485                 490                 495

Tyr Ser Asp Gly Gln Arg Arg His Phe Ile Ile Gln Tyr Val Asp Asn
                500                 505                 510

Met Tyr Arg Phe Glu Gly Thr Gly Phe Ser Asn Ile Pro Gln Leu Ile
            515                 520                 525

Asp His His Tyr Thr Thr Lys Gln Val Ile Thr Lys Lys Ser Gly Val
            530                 535                 540

Val Leu Leu Asn Pro Ile Pro Lys Asp Lys Trp Ile Leu Ser His
545                 550                 555                 560

Glu Asp Val Ile Leu Gly Glu Leu Leu Gly Lys Gly Asn Phe Gly Glu
                565                 570                 575

Val Tyr Lys Gly Thr Leu Lys Asp Lys Thr Ser Val Ala Val Lys Thr
            580                 585                 590

Cys Lys Glu Asp Leu Pro Gln Glu Leu Lys Ile Lys Phe Leu Gln Glu
            595                 600                 605

Ala Lys Ile Leu Lys Gln Tyr Asp His Pro Asn Ile Val Lys Leu Ile
610                 615                 620
```

```
Gly Val Cys Thr Gln Arg Gln Pro Val Tyr Ile Ile Met Glu Leu Val
625                 630                 635                 640

Ser Gly Gly Asp Phe Leu Thr Phe Leu Arg Arg Lys Lys Asp Glu Leu
            645                 650                 655

Lys Leu Lys Gln Leu Val Lys Phe Ser Leu Asp Ala Ala Ala Gly Met
        660                 665                 670

Leu Tyr Leu Glu Ser Lys Asn Cys Ile His Arg Asp Leu Ala Ala Arg
    675                 680                 685

Asn Cys Leu Val Gly Glu Asn Val Leu Lys Ile Ser Asp Phe Gly
690                 695                 700

Met Ser Arg Gln Glu Asp Gly Val Tyr Ser Ser Gly Leu Lys
705                 710                 715                 720

Gln Ile Pro Ile Lys Trp Thr Ala Pro Glu Ala Leu Asn Tyr Gly Arg
            725                 730                 735

Tyr Ser Ser Glu Ser Asp Val Trp Ser Phe Gly Ile Leu Leu Trp Glu
                740                 745                 750

Thr Phe Ser Leu Gly Val Cys Pro Tyr Pro Gly Met Thr Asn Gln Gln
        755                 760                 765

Ala Arg Glu Gln Val Glu Arg Gly Tyr Arg Met Ser Ala Pro Gln His
    770                 775                 780

Cys Pro Glu Asp Ile Ser Lys Ile Met Met Lys Cys Trp Asp Tyr Lys
785                 790                 795                 800

Pro Glu Asn Arg Pro Lys Phe Ser Glu Leu Gln Lys Glu Leu Thr Ile
            805                 810                 815

Ile Lys Arg Lys Leu Thr
            820

<210> SEQ ID NO 44
<211> LENGTH: 213
<212> TYPE: PRT
<213> ORGANISM: Homo sapiens

<400> SEQUENCE: 44

Met Ala Gln Glu Thr Asn Gln Thr Pro Gly Pro Met Leu Cys Ser Thr
1               5                   10                  15

Gly Cys Gly Phe Tyr Gly Asn Pro Arg Thr Asn Gly Met Cys Ser Val
            20                  25                  30

Cys Tyr Lys Glu His Leu Gln Arg Gln Gln Asn Ser Gly Arg Met Ser
        35                  40                  45

Pro Met Gly Thr Ala Ser Gly Ser Asn Ser Pro Thr Ser Asp Ser Ala
    50                  55                  60

Ser Val Gln Arg Ala Asp Thr Ser Leu Asn Asn Cys Glu Gly Ala Ala
65                  70                  75                  80

Gly Ser Thr Ser Glu Lys Ser Arg Asn Val Pro Val Ala Ala Leu Pro
            85                  90                  95

Val Thr Gln Gln Met Thr Glu Met Ser Ile Ser Arg Glu Asp Lys Ile
            100                 105                 110

Thr Thr Pro Lys Thr Glu Val Ser Glu Pro Val Val Thr Gln Pro Ser
        115                 120                 125

Pro Ser Val Ser Gln Pro Ser Thr Ser Gln Ser Glu Glu Lys Ala Pro
    130                 135                 140

Glu Leu Pro Lys Pro Lys Lys Asn Arg Cys Phe Met Cys Arg Lys Lys
145                 150                 155                 160

Val Gly Leu Thr Gly Phe Asp Cys Arg Cys Gly Asn Leu Phe Cys Gly
```

```
                    165                 170                 175
Leu His Arg Tyr Ser Asp Lys His Asn Cys Pro Tyr Asp Tyr Lys Ala
            180                 185                 190

Glu Ala Ala Lys Ile Arg Lys Glu Asn Pro Val Val Ala Glu
            195                 200             205

Lys Ile Gln Arg Ile
        210

<210> SEQ ID NO 45
<211> LENGTH: 1068
<212> TYPE: PRT
<213> ORGANISM: Homo sapiens

<400> SEQUENCE: 45

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320
```

-continued

```
Glu Thr Ser Thr Lys Ser Leu Trp Val Ile Asn Ser Ala Leu Arg Ile
            325                 330                 335

Lys Ile Leu Cys Ala Thr Tyr Val Asn Val Asn Ile Arg Asp Ile Asp
        340                 345                 350

Lys Ile Tyr Val Arg Thr Gly Ile Tyr His Gly Gly Glu Pro Leu Cys
            355                 360                 365

Asp Asn Val Asn Thr Gln Arg Val Pro Cys Ser Asn Pro Arg Trp Asn
370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
```

```
                740                 745                 750
Ser Pro Leu Asn Pro Ala His Gln Leu Gly Asn Leu Arg Leu Glu Glu
            755                 760                 765

Cys Arg Ile Met Ser Ser Ala Lys Arg Pro Leu Trp Leu Asn Trp Glu
        770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn Leu Phe Ser Met Met Leu Gly Ser
        995                 1000                1005

Gly Met Pro Glu Leu Gln Ser Phe Asp Asp Ile Ala Tyr Ile Arg
    1010                1015                1020

Lys Thr Leu Ala Leu Asp Lys Thr Glu Gln Glu Ala Leu Glu Tyr
    1025                1030                1035

Phe Met Lys Gln Met Asn Asp Ala His His Gly Gly Trp Thr Thr
    1040                1045                1050

Lys Met Asp Trp Ile Phe His Thr Ile Lys Gln His Ala Leu Asn
    1055                1060                1065

<210> SEQ ID NO 46
<211> LENGTH: 112
<212> TYPE: PRT
<213> ORGANISM: Homo sapiens

<400> SEQUENCE: 46

Met Ser Ala Glu Val Pro Glu Ala Ala Ser Glu Glu Gln Lys Glu
1               5                   10                  15

Met Glu Asp Lys Val Thr Ser Pro Glu Lys Ala Glu Glu Ala Lys Leu
                20                  25                  30

Lys Ala Arg Tyr Pro His Leu Gly Gln Lys Pro Gly Gly Ser Asp Phe
            35                  40                  45
```

```
Leu Arg Lys Arg Leu Gln Lys Gly Gln Lys Tyr Phe Asp Ser Gly Asp
    50                  55                  60

Tyr Asn Met Ala Lys Ala Lys Met Lys Asn Lys Gln Leu Pro Thr Ala
65                  70                  75                  80

Ala Pro Asp Lys Thr Glu Val Thr Gly Asp His Ile Pro Thr Pro Gln
                85                  90                  95

Asp Leu Pro Gln Arg Lys Pro Ser Leu Val Ala Ser Lys Leu Ala Gly
                100                 105                 110

<210> SEQ ID NO 47
<211> LENGTH: 543
<212> TYPE: PRT
<213> ORGANISM: Homo sapiens

<400> SEQUENCE: 47

Met Glu Gln Val Asn Glu Leu Lys Glu Lys Gly Asn Lys Ala Leu Ser
1               5                   10                  15

Val Gly Asn Ile Asp Asp Ala Leu Gln Cys Tyr Ser Glu Ala Ile Lys
                20                  25                  30

Leu Asp Pro His Asn His Val Leu Tyr Ser Asn Arg Ser Ala Ala Tyr
            35                  40                  45

Ala Lys Lys Gly Asp Tyr Gln Lys Ala Tyr Glu Asp Gly Cys Lys Thr
    50                  55                  60

Val Asp Leu Lys Pro Asp Trp Gly Lys Gly Tyr Ser Arg Lys Ala Ala
65                  70                  75                  80

Ala Leu Glu Phe Leu Asn Arg Phe Glu Glu Ala Lys Arg Thr Tyr Glu
                85                  90                  95

Glu Gly Leu Lys His Glu Ala Asn Asn Pro Gln Leu Lys Glu Gly Leu
                100                 105                 110

Gln Asn Met Glu Ala Arg Leu Ala Glu Arg Lys Phe Met Asn Pro Phe
            115                 120                 125

Asn Met Pro Asn Leu Tyr Gln Lys Leu Glu Ser Asp Pro Arg Thr Arg
130                 135                 140

Thr Leu Leu Ser Asp Pro Thr Tyr Arg Glu Leu Ile Glu Gln Leu Arg
145                 150                 155                 160

Asn Lys Pro Ser Asp Leu Gly Thr Lys Leu Gln Asp Pro Arg Ile Met
                165                 170                 175

Thr Thr Leu Ser Val Leu Leu Gly Val Asp Leu Gly Ser Met Asp Glu
                180                 185                 190

Glu Glu Glu Ile Ala Thr Pro Pro Pro Pro Pro Lys Lys Glu
            195                 200                 205

Thr Lys Pro Glu Pro Met Glu Glu Asp Leu Pro Glu Asn Lys Lys Gln
    210                 215                 220

Ala Leu Lys Glu Lys Glu Leu Gly Asn Asp Ala Tyr Lys Lys Lys Asp
225                 230                 235                 240

Phe Asp Thr Ala Leu Lys His Tyr Asp Lys Ala Lys Glu Leu Asp Pro
                245                 250                 255

Thr Asn Met Thr Tyr Ile Thr Asn Gln Ala Ala Val Tyr Phe Glu Lys
                260                 265                 270

Gly Asp Tyr Asn Lys Cys Arg Glu Leu Cys Glu Lys Ala Ile Glu Val
            275                 280                 285

Gly Arg Glu Asn Arg Glu Asp Tyr Arg Gln Ile Ala Lys Ala Tyr Ala
    290                 295                 300

Arg Ile Gly Asn Ser Tyr Phe Lys Glu Glu Lys Tyr Lys Asp Ala Ile
305                 310                 315                 320
```

His Phe Tyr Asn Lys Ser Leu Ala Glu His Arg Thr Pro Asp Val Leu
                325                 330                 335

Lys Lys Cys Gln Gln Ala Glu Lys Ile Leu Lys Glu Gln Glu Arg Leu
            340                 345                 350

Ala Tyr Ile Asn Pro Asp Leu Ala Leu Glu Glu Lys Asn Lys Gly Asn
        355                 360                 365

Glu Cys Phe Gln Lys Gly Asp Tyr Pro Gln Ala Met Lys His Tyr Thr
    370                 375                 380

Glu Ala Ile Lys Arg Asn Pro Lys Asp Ala Lys Leu Tyr Ser Asn Arg
385                 390                 395                 400

Ala Ala Cys Tyr Thr Lys Leu Leu Glu Phe Gln Leu Ala Leu Lys Asp
                405                 410                 415

Cys Glu Glu Cys Ile Gln Leu Glu Pro Thr Phe Ile Lys Gly Tyr Thr
            420                 425                 430

Arg Lys Ala Ala Ala Leu Glu Ala Met Lys Asp Tyr Thr Lys Ala Met
        435                 440                 445

Asp Val Tyr Gln Lys Ala Leu Asp Leu Asp Ser Ser Cys Lys Glu Ala
    450                 455                 460

Ala Asp Gly Tyr Gln Arg Cys Met Met Ala Gln Tyr Asn Arg His Asp
465                 470                 475                 480

Ser Pro Glu Asp Val Lys Arg Arg Ala Met Ala Asp Pro Glu Val Gln
                485                 490                 495

Gln Ile Met Ser Asp Pro Ala Met Arg Leu Ile Leu Glu Gln Met Gln
            500                 505                 510

Lys Asp Pro Gln Ala Leu Ser Glu His Leu Lys Asn Pro Val Ile Ala
        515                 520                 525

Gln Lys Ile Gln Lys Leu Met Asp Val Gly Leu Ile Ala Ile Arg
    530                 535                 540

<210> SEQ ID NO 48
<211> LENGTH: 463
<212> TYPE: PRT
<213> ORGANISM: Homo sapiens

<400> SEQUENCE: 48

Met Gly Trp Ile Thr Glu Asp Leu Ile Arg Arg Asn Ala Glu His Asn
1               5                   10                  15

Asp Cys Val Ile Phe Ser Leu Glu Glu Leu Ser Leu His Gln Gln Glu
                20                  25                  30

Ile Glu Arg Leu Glu His Ile Asp Lys Trp Cys Arg Asp Leu Lys Ile
            35                  40                  45

Leu Tyr Leu Gln Asn Asn Leu Ile Gly Lys Ile Glu Asn Val Ser Lys
        50                  55                  60

Leu Lys Lys Leu Glu Tyr Leu Asn Leu Ala Leu Asn Asn Ile Glu Lys
65                  70                  75                  80

Ile Glu Asn Leu Glu Gly Cys Glu Glu Leu Ala Lys Leu Asp Leu Thr
                85                  90                  95

Val Asn Phe Ile Gly Glu Leu Ser Ser Ile Lys Asn Leu Gln His Asn
            100                 105                 110

Ile His Leu Lys Glu Leu Phe Leu Met Gly Asn Pro Cys Ala Ser Phe
        115                 120                 125

Asp His Tyr Arg Glu Phe Val Val Ala Thr Leu Pro Gln Leu Lys Trp
    130                 135                 140

Leu Asp Gly Lys Glu Ile Glu Pro Ser Glu Arg Ile Lys Ala Leu Gln

```
                145                 150                 155                 160
Asp Tyr Ser Val Ile Glu Pro Gln Ile Arg Glu Gln Glu Lys Asp His
                165                 170                 175

Cys Leu Lys Arg Ala Lys Leu Lys Glu Glu Ala Gln Arg Lys His Gln
                180                 185                 190

Glu Glu Asp Lys Asn Glu Asp Lys Arg Ser Asn Ala Gly Phe Asp Gly
                195                 200                 205

Arg Trp Tyr Thr Asp Ile Asn Ala Thr Leu Ser Ser Leu Glu Ser Lys
                210                 215                 220

Asp His Leu Gln Ala Pro Asp Ile Glu Glu His Asn Thr Lys Lys Leu
225                 230                 235                 240

Asp Asp Asp Leu Glu Phe Trp Asn Lys Pro Cys Leu Phe Thr Pro Glu
                245                 250                 255

Ser Arg Leu Glu Thr Leu Arg His Met Glu Lys Gln Arg Lys Lys Gln
                260                 265                 270

Glu Lys Leu Ser Glu Lys Lys Lys Val Lys Pro Arg Thr Leu
                275                 280                 285

Ile Thr Glu Asp Gly Lys Ala Leu Asn Val Asn Glu Pro Lys Ile Asp
                290                 295                 300

Phe Ser Leu Lys Asp Asn Glu Lys Gln Ile Ile Leu Asp Leu Ala Val
305                 310                 315                 320

Tyr Arg Tyr Met Asp Thr Ser Leu Ile Asp Val Asp Val Gln Pro Thr
                325                 330                 335

Tyr Val Arg Val Met Ile Lys Gly Lys Pro Phe Gln Leu Val Leu Pro
                340                 345                 350

Ala Glu Val Lys Pro Asp Ser Ser Ala Lys Arg Ser Gln Thr Thr
                355                 360                 365

Gly His Leu Val Ile Cys Met Pro Lys Val Gly Glu Val Ile Thr Gly
                370                 375                 380

Gly Gln Arg Ala Phe Lys Ser Met Lys Thr Thr Ser Asp Arg Ser Arg
385                 390                 395                 400

Glu Gln Thr Asn Thr Arg Ser Lys His Met Glu Lys Leu Glu Val Asp
                405                 410                 415

Pro Ser Lys His Ser Phe Pro Asp Val Thr Asn Ile Val Gln Glu Lys
                420                 425                 430

Lys His Thr Pro Arg Arg Pro Glu Pro Lys Ile Ile Pro Ser Glu
                435                 440                 445

Glu Asp Pro Thr Phe Glu Asp Asn Pro Glu Val Pro Pro Leu Ile
450                 455                 460

<210> SEQ ID NO 49
<211> LENGTH: 676
<212> TYPE: PRT
<213> ORGANISM: Homo sapiens

<400> SEQUENCE: 49

Met Asp Lys Tyr Asp Asp Leu Gly Leu Glu Ala Ser Lys Phe Ile Glu
1               5                   10                  15

Asp Leu Asn Met Tyr Glu Ala Ser Lys Asp Gly Leu Phe Arg Val Asp
                20                  25                  30

Lys Gly Ala Gly Asn Asn Pro Glu Phe Glu Glu Thr Arg Arg Val Phe
                35                  40                  45

Ala Thr Lys Met Ala Lys Ile His Leu Gln Gln Gln Gln Gln Gln Leu
                50                  55                  60
```

```
Leu Gln Glu Glu Thr Leu Pro Arg Gly Ser Arg Gly Pro Val Asn Gly
 65                  70                  75                  80

Gly Gly Arg Leu Gly Pro Gln Ala Arg Trp Glu Val Val Gly Ser Lys
                 85                  90                  95

Leu Thr Val Asp Gly Ala Ala Lys Pro Pro Leu Ala Ala Ser Thr Gly
            100                 105                 110

Ala Pro Gly Ala Val Thr Thr Leu Ala Ala Gly Gln Pro Pro Tyr Pro
        115                 120                 125

Pro Gln Glu Gln Arg Ser Arg Pro Tyr Leu His Gly Thr Arg His Gly
    130                 135                 140

Ser Gln Asp Cys Gly Ser Arg Glu Ser Leu Ala Thr Ser Glu Met Ser
145                 150                 155                 160

Ala Phe His Gln Pro Gly Pro Cys Glu Asp Pro Ser Cys Leu Thr His
                165                 170                 175

Gly Asp Tyr Tyr Asp Asn Leu Ser Leu Ala Ser Pro Lys Trp Gly Asp
            180                 185                 190

Lys Pro Gly Val Ser Pro Ser Ile Gly Leu Ser Val Gly Ser Gly Trp
        195                 200                 205

Pro Ser Ser Pro Gly Ser Asp Pro Pro Leu Pro Lys Pro Cys Gly Asp
210                 215                 220

His Pro Leu Asn His Arg Gln Leu Ser Leu Ser Ser Arg Ser Ser
225                 230                 235                 240

Glu Gly Ser Leu Gly Gly Gln Asn Ser Gly Ile Gly Gly Arg Ser Ser
                245                 250                 255

Glu Lys Pro Thr Gly Leu Trp Ser Thr Ala Ser Ser Gln Arg Val Ser
            260                 265                 270

Pro Gly Leu Pro Ser Pro Asn Leu Glu Asn Gly Ala Pro Ala Val Gly
        275                 280                 285

Pro Val Gln Pro Arg Thr Pro Ser Val Ser Ala Pro Leu Ala Leu Ser
    290                 295                 300

Cys Pro Arg Gln Gly Gly Leu Pro Arg Ser Asn Ser Gly Leu Gly Gly
305                 310                 315                 320

Glu Val Ser Gly Val Met Ser Lys Pro Asn Val Asp Pro Gln Pro Trp
                325                 330                 335

Phe Gln Asp Gly Pro Lys Ser Tyr Leu Ser Ser Ala Pro Ser Ser
            340                 345                 350

Ser Pro Ala Gly Leu Asp Gly Ser Gln Gln Gly Ala Val Pro Gly Leu
        355                 360                 365

Gly Pro Lys Pro Gly Cys Thr Asp Leu Gly Thr Gly Pro Lys Leu Ser
    370                 375                 380

Pro Thr Ser Leu Val His Pro Val Met Ser Thr Leu Pro Glu Leu Ser
385                 390                 395                 400

Cys Lys Glu Gly Pro Leu Gly Trp Ser Ser Asp Gly Ser Leu Gly Ser
                405                 410                 415

Val Leu Leu Asp Ser Pro Ser Ser Pro Arg Val Arg Leu Pro Cys Gln
            420                 425                 430

Pro Leu Val Pro Gly Pro Glu Leu Arg Pro Ser Ala Ala Glu Leu Lys
        435                 440                 445

Leu Glu Ala Leu Thr Gln Arg Leu Glu Arg Glu Met Asp Ala His Pro
    450                 455                 460

Lys Ala Asp Tyr Phe Gly Ala Cys Val Lys Cys Ser Lys Gly Val Phe
465                 470                 475                 480

Gly Ala Gly Gln Ala Cys Gln Ala Met Gly Asn Leu Tyr His Asp Thr
```

```
            485                 490                 495
Cys Phe Thr Cys Ala Ala Cys Ser Arg Lys Leu Arg Gly Lys Ala Phe
            500                 505                 510

Tyr Phe Val Asn Gly Lys Val Phe Cys Glu Glu Asp Phe Leu Tyr Ser
        515                 520                 525

Gly Phe Gln Gln Ser Ala Asp Arg Cys Phe Leu Cys Gly His Leu Ile
    530                 535                 540

Met Asp Met Ile Leu Gln Ala Leu Gly Lys Ser Tyr His Pro Gly Cys
545                 550                 555                 560

Phe Arg Cys Val Ile Cys Asn Glu Cys Leu Asp Gly Val Pro Phe Thr
                565                 570                 575

Val Asp Ser Glu Asn Lys Ile Tyr Cys Val Arg Asp Tyr His Lys Val
            580                 585                 590

Leu Ala Pro Lys Cys Ala Ala Cys Gly Leu Pro Ile Leu Pro Pro Glu
        595                 600                 605

Gly Ser Asp Glu Thr Ile Arg Val Val Ser Met Asp Arg Asp Tyr His
    610                 615                 620

Val Glu Cys Tyr His Cys Glu Asp Cys Gly Leu Glu Leu Asn Asp Glu
625                 630                 635                 640

Asp Gly His Arg Cys Tyr Pro Leu Glu Asp His Leu Phe Cys His Ser
                645                 650                 655

Cys His Val Lys Arg Leu Glu Lys Arg Pro Ser Ser Thr Ala Leu His
            660                 665                 670

Gln His His Phe
        675

<210> SEQ ID NO 50
<211> LENGTH: 113
<212> TYPE: PRT
<213> ORGANISM: Homo sapiens

<400> SEQUENCE: 50

Met Ala Asp Val Glu Asp Gly Glu Glu Thr Cys Ala Leu Ala Ser His
1               5                   10                  15

Ser Gly Ser Gly Ser Lys Ser Gly Gly Asp Lys Met Phe Ser Leu
            20                  25                  30

Lys Lys Trp Asn Ala Val Ala Met Trp Ser Trp Asp Val Glu Cys Asp
        35                  40                  45

Thr Cys Ala Ile Cys Arg Val Gln Val Met Asp Ala Cys Leu Arg Cys
    50                  55                  60

Gln Ala Glu Asn Lys Gln Glu Asp Cys Val Val Val Trp Gly Glu Cys
65                  70                  75                  80

Asn His Ser Phe His Asn Cys Cys Met Ser Leu Trp Val Lys Gln Asn
                85                  90                  95

Asn Arg Cys Pro Leu Cys Gln Gln Asp Trp Val Val Gln Arg Ile Gly
            100                 105                 110

Lys

<210> SEQ ID NO 51
    <211> LENGTH: 153
<212> TYPE: PRT
<213> ORGANISM: Homo sapiens

<400> SEQUENCE: 51

Met Thr Ser Glu Ser Thr Ser Pro Pro Val Val Pro Pro Leu His Ser
1               5                   10                  15
```

Pro Lys Ser Pro Val Trp Pro Thr Phe Pro Phe His Arg Glu Gly Ser
              20                  25                  30

Arg Val Trp Glu Arg Gly Gly Val Pro Pro Arg Asp Leu Pro Ser Pro
          35                  40                  45

Leu Pro Thr Lys Arg Thr Arg Thr Tyr Ser Ala Thr Ala Arg Ala Ser
 50                  55                  60

Ala Gly Pro Val Phe Lys Gly Val Cys Lys Gln Phe Ser Arg Ser Gln
 65                  70                  75                  80

Gly His Gly Phe Ile Thr Pro Glu Asn Gly Ser Glu Asp Ile Phe Val
                  85                  90                  95

His Val Ser Asp Ile Glu Gly Gly Tyr Val Pro Val Glu Gly Asp Glu
                 100                 105                 110

Val Thr Tyr Lys Met Cys Pro Ile Pro Pro Lys Asn Gln Lys Phe Gln
                 115                 120                 125

Ala Val Glu Val Val Leu Thr Gln Leu Ala Pro His Thr Pro His Glu
             130                 135                 140

Thr Trp Ser Gly Gln Val Val Gly Ser
145                 150

<210> SEQ ID NO 52
<211> LENGTH: 786
<212> TYPE: PRT
<213> ORGANISM: Homo sapiens

<400> SEQUENCE: 52

Met Val His Phe Cys Gly Leu Leu Thr Leu His Arg Glu Pro Val Pro
1               5                   10                  15

Leu Lys Ser Ile Ser Val Ser Val Asn Ile Tyr Glu Phe Val Ala Gly
              20                  25                  30

Val Ser Ala Thr Leu Asn Tyr Glu Asn Glu Glu Lys Val Pro Leu Glu
          35                  40                  45

Ala Phe Phe Val Phe Pro Met Asp Glu Asp Ser Ala Val Tyr Ser Phe
 50                  55                  60

Glu Ala Leu Val Asp Gly Lys Lys Ile Val Ala Glu Leu Gln Asp Lys
 65                  70                  75                  80

Met Lys Ala Arg Thr Asn Tyr Glu Lys Ala Ile Ser Gln Gly His Gln
                  85                  90                  95

Ala Phe Leu Leu Glu Gly Asp Ser Ser Arg Asp Val Phe Ser Cys
                 100                 105                 110

Asn Val Gly Asn Leu Gln Pro Gly Ser Lys Ala Ala Val Thr Leu Lys
                 115                 120                 125

Tyr Val Gln Glu Leu Pro Leu Glu Ala Asp Gly Ala Leu Arg Phe Val
             130                 135                 140

Leu Pro Ala Val Leu Asn Pro Arg Tyr Gln Phe Ser Gly Ser Ser Lys
145                 150                 155                 160

Asp Ser Cys Leu Asn Val Lys Thr Pro Ile Val Pro Val Glu Asp Leu
                 165                 170                 175

Pro Tyr Thr Leu Ser Met Val Ala Thr Ile Asp Ser Gln His Gly Ile
             180                 185                 190

Glu Lys Val Gln Ser Asn Cys Pro Leu Ser Pro Thr Glu Tyr Leu Gly
             195                 200                 205

Glu Asp Lys Thr Ser Ala Gln Val Ser Leu Ala Ala Gly His Lys Phe
        210                 215                 220

Asp Arg Asp Val Glu Leu Leu Ile Tyr Tyr Asn Glu Val His Thr Pro

```
            225                 230                 235                 240
Ser Val Val Leu Glu Met Gly Met Pro Asn Met Lys Pro Gly His Leu
                    245                 250                 255

Met Gly Asp Pro Ser Ala Met Val Ser Phe Tyr Pro Asn Ile Pro Glu
            260                 265                 270

Asp Gln Pro Ser Asn Thr Cys Gly Glu Phe Ile Phe Leu Met Asp Arg
            275                 280                 285

Ser Gly Ser Met Gln Ser Pro Met Ser Ser Gln Asp Thr Ser Gln Leu
            290                 295                 300

Arg Ile Gln Ala Ala Lys Glu Thr Leu Ile Leu Leu Lys Ser Leu
305                 310                 315                 320

Pro Ile Gly Cys Tyr Phe Asn Ile Tyr Gly Phe Gly Ser Ser Tyr Glu
                    325                 330                 335

Ala Cys Phe Pro Glu Ser Val Lys Tyr Thr Gln Thr Met Glu Glu
            340                 345                 350

Ala Leu Gly Arg Val Lys Leu Met Gln Ala Asp Leu Gly Gly Thr Glu
            355                 360                 365

Ile Leu Ala Pro Leu Gln Asn Ile Tyr Arg Gly Pro Ser Ile Pro Gly
370                 375                 380

His Pro Leu Gln Leu Phe Val Phe Thr Asp Gly Glu Val Thr Asp Thr
385                 390                 395                 400

Phe Ser Val Ile Lys Glu Val Arg Ile Asn Arg Gln Lys His Arg Cys
                    405                 410                 415

Phe Ser Phe Gly Ile Gly Glu Gly Thr Ser Thr Ser Leu Ile Lys Gly
                    420                 425                 430

Ile Ala Arg Ala Ser Gly Gly Thr Ser Glu Phe Ile Thr Gly Lys Asp
            435                 440                 445

Arg Met Gln Ser Lys Ala Leu Arg Thr Leu Lys Arg Ser Leu Gln Pro
            450                 455                 460

Val Val Glu Asp Val Ser Leu Ser Trp His Leu Pro Pro Gly Leu Ser
465                 470                 475                 480

Ala Lys Met Leu Ser Pro Glu Gln Thr Val Ile Phe Arg Gly Gln Arg
                    485                 490                 495

Leu Ile Ser Tyr Ala Gln Leu Thr Gly Arg Met Pro Ala Ala Glu Thr
            500                 505                 510

Thr Gly Glu Val Cys Leu Lys Tyr Thr Leu Gln Gly Lys Thr Phe Glu
            515                 520                 525

Asp Lys Val Thr Phe Pro Leu Gln Pro Lys Pro Asp Val Asn Leu Thr
            530                 535                 540

Ile His Arg Leu Ala Ala Lys Ser Leu Leu Gln Thr Lys Asp Met Gly
545                 550                 555                 560

Leu Arg Glu Thr Pro Ala Ser Asp Lys Lys Asp Ala Leu Asn Leu Ser
                    565                 570                 575

Leu Glu Ser Gly Val Ile Ser Ser Phe Thr Ala Phe Ile Ala Ile Asn
                    580                 585                 590

Lys Glu Leu Asn Lys Pro Val Gln Gly Pro Leu Ala His Arg Asp Val
            595                 600                 605

Pro Arg Pro Ile Leu Leu Gly Ala Ser Ala Pro Leu Lys Ile Lys Cys
            610                 615                 620

Gln Ser Gly Phe Arg Lys Ala Leu His Ser Asp Arg Pro Pro Ser Ala
625                 630                 635                 640

Ser Gln Pro Arg Gly Glu Leu Met Cys Tyr Lys Ala Lys Thr Phe Gln
                    645                 650                 655
```

```
Met Asp Asp Tyr Ser Leu Cys Gly Leu Ile Ser His Lys Asp Gln His
            660                 665                 670

Ser Pro Gly Phe Gly Glu Asn His Leu Val Gln Leu Ile Tyr His Gln
            675                 680                 685

Asn Ala Asn Gly Ser Trp Asp Leu Asn Glu Asp Leu Ala Lys Ile Leu
        690                 695                 700

Gly Met Ser Leu Glu Glu Ile Met Ala Ala Gln Pro Ala Glu Leu Val
705                 710                 715                 720

Asp Ser Ser Gly Trp Ala Thr Ile Leu Ala Val Ile Trp Leu His Ser
                725                 730                 735

Asn Gly Lys Asp Leu Lys Cys Glu Trp Glu Leu Leu Glu Arg Lys Ala
            740                 745                 750

Val Ala Trp Met Arg Ala His Ala Gly Ser Thr Met Pro Ser Val Val
            755                 760                 765

Lys Ala Ala Ile Thr Phe Leu Lys Ser Ser Val Asp Pro Ala Ile Phe
    770                 775                 780

Ala Phe
785

<210> SEQ ID NO 53
<211> LENGTH: 181
<212> TYPE: PRT
<213> ORGANISM: Homo sapiens

<400> SEQUENCE: 53

Met Pro Lys Gly Gly Arg Lys Gly Gly His Lys Gly Arg Ala Arg Gln
1               5                   10                  15

Tyr Thr Ser Pro Glu Glu Ile Asp Ala Gln Leu Gln Ala Glu Lys Gln
            20                  25                  30

Lys Ala Arg Glu Glu Glu Glu Gln Lys Glu Gly Gly Asp Gly Ala Ala
        35                  40                  45

Gly Asp Pro Lys Lys Glu Lys Lys Ser Leu Asp Ser Asp Glu Ser Glu
    50                  55                  60

Asp Glu Glu Asp Asp Tyr Gln Gln Lys Arg Lys Gly Val Glu Gly Leu
65                  70                  75                  80

Ile Asp Ile Glu Asn Pro Asn Arg Val Ala Gln Thr Thr Lys Lys Val
                85                  90                  95

Thr Gln Leu Asp Leu Asp Gly Pro Lys Glu Leu Ser Arg Arg Glu Arg
            100                 105                 110

Glu Glu Ile Glu Lys Gln Lys Ala Lys Glu Arg Tyr Met Lys Met His
        115                 120                 125

Leu Ala Gly Lys Thr Glu Gln Ala Lys Ala Asp Leu Ala Arg Leu Ala
    130                 135                 140

Ile Ile Arg Lys Gln Arg Glu Glu Ala Ala Arg Lys Lys Glu Glu Glu
145                 150                 155                 160

Arg Lys Ala Lys Asp Asp Ala Thr Leu Ser Gly Lys Arg Met Gln Ser
                165                 170                 175

Leu Ser Leu Asn Lys
            180

<210> SEQ ID NO 54
<211> LENGTH: 837
<212> TYPE: PRT
<213> ORGANISM: Homo sapiens

<400> SEQUENCE: 54
```

```
Met Ala Ser Lys Arg Lys Ser Thr Thr Pro Cys Met Val Arg Thr Ser
1               5                   10                  15

Gln Val Val Glu Gln Asp Val Pro Glu Val Asp Arg Ala Lys Glu
            20                  25                  30

Lys Gly Ile Gly Thr Pro Gln Pro Asp Val Ala Lys Asp Ser Trp Ala
                35                  40                  45

Ala Glu Leu Glu Asn Ser Ser Lys Glu Asn Glu Val Ile Glu Val Lys
        50                  55                  60

Ser Met Gly Glu Ser Gln Ser Lys Lys Leu Gln Gly Gly Tyr Glu Cys
65                  70                  75                  80

Lys Tyr Cys Pro Tyr Ser Thr Gln Asn Leu Asn Glu Phe Thr Glu His
                85                  90                  95

Val Asp Met Gln His Pro Asn Val Ile Leu Asn Pro Leu Tyr Val Cys
            100                 105                 110

Ala Glu Cys Asn Phe Thr Thr Lys Lys Tyr Asp Ser Leu Ser Asp His
            115                 120                 125

Asn Ser Lys Phe His Pro Gly Glu Ala Asn Phe Lys Leu Lys Leu Ile
130                 135                 140

Lys Arg Asn Asn Gln Thr Val Leu Glu Gln Ser Ile Glu Thr Thr Asn
145                 150                 155                 160

His Val Val Ser Ile Thr Thr Ser Gly Pro Gly Thr Gly Asp Ser Asp
                165                 170                 175

Ser Gly Ile Ser Val Ser Lys Thr Pro Ile Met Lys Pro Gly Lys Pro
                180                 185                 190

Lys Ala Asp Ala Lys Lys Val Pro Lys Lys Pro Glu Glu Ile Thr Pro
            195                 200                 205

Glu Asn His Val Glu Gly Thr Ala Arg Leu Val Thr Asp Thr Ala Glu
210                 215                 220

Ile Leu Ser Arg Leu Gly Gly Val Glu Leu Leu Gln Asp Thr Leu Gly
225                 230                 235                 240

His Val Met Pro Ser Val Gln Leu Pro Pro Asn Ile Asn Leu Val Pro
                245                 250                 255

Lys Val Pro Val Pro Leu Asn Thr Thr Lys Tyr Asn Ser Ala Leu Asp
                260                 265                 270

Thr Asn Ala Thr Met Ile Asn Ser Phe Asn Lys Phe Pro Tyr Pro Thr
                275                 280                 285

Gln Ala Glu Leu Ser Trp Leu Thr Ala Ala Ser Lys His Pro Glu Glu
        290                 295                 300

His Ile Arg Ile Trp Phe Ala Thr Gln Arg Leu Lys His Gly Ile Ser
305                 310                 315                 320

Trp Ser Pro Glu Glu Val Glu Glu Ala Arg Lys Lys Met Phe Asn Gly
                325                 330                 335

Thr Ile Gln Ser Val Pro Pro Thr Ile Thr Val Leu Pro Ala Gln Leu
            340                 345                 350

Ala Pro Thr Lys Val Thr Gln Pro Ile Leu Gln Thr Ala Leu Pro Cys
            355                 360                 365

Gln Ile Leu Gly Gln Thr Ser Leu Val Leu Thr Gln Val Ser Gly
        370                 375                 380

Ser Thr Thr Val Ser Cys Ser Pro Ile Thr Leu Ala Val Ala Gly Val
385                 390                 395                 400

Thr Asn His Gly Gln Lys Arg Pro Leu Val Thr Pro Gln Ala Ala Pro
                405                 410                 415
```

```
Glu Pro Lys Arg Pro His Ile Ala Gln Val Pro Glu Pro Pro Lys
            420                 425                 430

Val Ala Asn Pro Pro Leu Thr Pro Ala Ser Asp Arg Lys Lys Thr Lys
                435                 440                 445

Glu Gln Ile Ala His Leu Lys Ala Ser Phe Leu Gln Ser Gln Phe Pro
450                 455                 460

Asp Asp Ala Glu Val Tyr Arg Leu Ile Glu Val Thr Gly Leu Ala Arg
465                 470                 475                 480

Ser Glu Ile Lys Lys Trp Phe Ser Asp His Arg Tyr Arg Cys Gln Arg
                485                 490                 495

Gly Ile Val His Ile Thr Ser Glu Ser Leu Ala Lys Asp Gln Leu Ala
            500                 505                 510

Ile Ala Ala Ser Arg His Gly Arg Thr Tyr His Ala Tyr Pro Asp Phe
        515                 520                 525

Ala Pro Gln Lys Phe Lys Glu Lys Thr Gln Gly Gln Val Lys Ile Leu
    530                 535                 540

Glu Asp Ser Phe Leu Lys Ser Ser Phe Pro Thr Gln Ala Glu Leu Asp
545                 550                 555                 560

Arg Leu Arg Val Glu Thr Lys Leu Ser Arg Arg Glu Ile Asp Ser Trp
                565                 570                 575

Phe Ser Glu Arg Arg Lys Leu Arg Asp Ser Met Glu Gln Ala Val Leu
            580                 585                 590

Asp Ser Met Gly Ser Gly Lys Lys Gly Gln Asp Val Gly Ala Pro Asn
        595                 600                 605

Gly Ala Leu Ser Arg Leu Asp Gln Leu Ser Gly Ala Gln Leu Thr Ser
    610                 615                 620

Ser Leu Pro Ser Pro Ser Pro Ala Ile Ala Lys Ser Gln Glu Gln Val
625                 630                 635                 640

His Leu Leu Arg Ser Thr Phe Ala Arg Thr Gln Trp Pro Thr Pro Gln
                645                 650                 655

Glu Tyr Asp Gln Leu Ala Ala Lys Thr Gly Leu Val Arg Thr Glu Ile
            660                 665                 670

Val Arg Trp Phe Lys Glu Asn Arg Cys Leu Leu Lys Thr Gly Thr Val
        675                 680                 685

Lys Trp Met Glu Gln Tyr Gln His Gln Pro Met Ala Asp Asp His Gly
    690                 695                 700

Tyr Asp Ala Val Ala Arg Lys Ala Thr Lys Pro Met Ala Glu Ser Pro
705                 710                 715                 720

Lys Asn Gly Gly Asp Val Val Pro Gln Tyr Tyr Lys Asp Pro Lys Lys
                725                 730                 735

Leu Cys Glu Glu Asp Leu Glu Lys Leu Val Thr Arg Val Lys Val Gly
            740                 745                 750

Ser Glu Pro Ala Lys Asp Cys Leu Pro Ala Lys Pro Ser Glu Ala Thr
        755                 760                 765

Ser Asp Arg Ser Glu Gly Ser Arg Asp Gly Gln Gly Ser Asp Glu
    770                 775                 780

Asn Glu Glu Ser Ser Val Val Asp Tyr Val Glu Val Thr Val Gly Glu
785                 790                 795                 800

Glu Asp Ala Ile Ser Asp Arg Ser Asp Ser Trp Ser Gln Ala Ala Ala
                805                 810                 815

Glu Gly Val Ser Glu Leu Ala Glu Ser Asp Ser Asp Cys Val Pro Ala
            820                 825                 830

Glu Ala Gly Gln Ala
```

```
                835

<210> SEQ ID NO 55
<211> LENGTH: 803
<212> TYPE: PRT
<213> ORGANISM: Homo sapiens

<400> SEQUENCE: 55

Met Glu Val Lys Pro Val Gly Glu Pro Thr Gln Glu Val Ser Lys Phe
1               5                   10                  15

Lys Leu Ser Thr Lys Val Glu Ser Thr Gly His Trp Leu Val Glu Asp
                20                  25                  30

His Val Arg Ile Trp Glu Val Leu Lys Thr Glu Ser Ser Ile Gln
            35                  40                  45

Asp Trp Gly Glu Glu Val Glu Glu Gly Ala Val Tyr His Val Thr Leu
    50                  55                  60

Lys Arg Val Gln Ile Gln Gln Ala Ala Asn Lys Gly Ala Arg Trp Leu
65                  70                  75                  80

Gly Val Glu Gly Asp Gln Leu Pro Pro Gly His Thr Val Ser Gln Tyr
                85                  90                  95

Glu Thr Cys Lys Ile Arg Thr Ile Lys Ala Gly Thr Leu Glu Lys Leu
            100                 105                 110

Val Glu Asn Leu Leu Thr Ala Phe Gly Asp Asn Asp Phe Thr Tyr Ile
        115                 120                 125

Ser Ile Phe Leu Ser Thr Tyr Arg Gly Phe Ala Ser Thr Lys Glu Val
    130                 135                 140

Leu Glu Leu Leu Leu Asp Arg Tyr Gly Asn Leu Thr Ser Pro Asn Cys
145                 150                 155                 160

Glu Glu Asp Gly Ser Gln Ser Ser Glu Ser Lys Met Val Ile Arg
                165                 170                 175

Asn Ala Ile Ala Ser Ile Leu Arg Ala Trp Leu Asp Gln Cys Ala Glu
            180                 185                 190

Asp Phe Arg Glu Pro Pro His Phe Pro Cys Leu Gln Lys Leu Leu Asp
        195                 200                 205

Tyr Leu Thr Arg Met Met Pro Gly Ser Asp Pro Glu Arg Arg Ala Gln
    210                 215                 220

Asn Leu Leu Glu Gln Phe Gln Lys Gln Glu Val Glu Thr Asp Asn Gly
225                 230                 235                 240

Leu Pro Asn Thr Ile Ser Phe Ser Leu Glu Glu Glu Glu Leu Glu
                245                 250                 255

Gly Gly Glu Ser Ala Glu Phe Thr Cys Phe Ser Glu Asp Leu Val Ala
            260                 265                 270

Glu Gln Leu Thr Tyr Met Asp Ala Gln Leu Phe Lys Lys Val Val Pro
        275                 280                 285

His His Cys Leu Gly Cys Ile Trp Ser Arg Arg Asp Lys Lys Glu Asn
    290                 295                 300

Lys His Leu Ala Pro Thr Ile Arg Ala Thr Ile Ser Gln Phe Asn Thr
305                 310                 315                 320

Leu Thr Lys Cys Val Val Ser Thr Ile Leu Gly Gly Lys Glu Leu Lys
                325                 330                 335

Thr Gln Gln Arg Ala Lys Ile Ile Glu Lys Trp Ile Asn Ile Ala His
            340                 345                 350

Glu Cys Arg Leu Leu Lys Asn Phe Ser Ser Leu Arg Ala Ile Val Ser
        355                 360                 365
```

```
Ala Leu Gln Ser Asn Ser Ile Tyr Arg Leu Lys Lys Thr Trp Ala Ala
    370                 375                 380

Val Pro Arg Asp Arg Met Leu Met Phe Glu Glu Leu Ser Asp Ile Phe
385                 390                 395                 400

Ser Asp His Asn Asn His Leu Thr Ser Arg Glu Leu Leu Met Lys Glu
                405                 410                 415

Gly Thr Ser Lys Phe Ala Asn Leu Asp Ser Ser Val Lys Glu Asn Gln
            420                 425                 430

Lys Arg Thr Gln Arg Arg Leu Gln Leu Gln Lys Asp Met Gly Val Met
        435                 440                 445

Gln Gly Thr Val Pro Tyr Leu Gly Thr Phe Leu Thr Asp Leu Thr Met
    450                 455                 460

Leu Asp Thr Ala Leu Gln Asp Tyr Ile Glu Gly Leu Ile Asn Phe
465                 470                 475                 480

Glu Lys Arg Arg Arg Glu Phe Glu Val Ile Ala Gln Ile Lys Leu Leu
                485                 490                 495

Gln Ser Ala Cys Asn Ser Tyr Cys Met Thr Pro Asp Gln Lys Phe Ile
            500                 505                 510

Gln Trp Phe Gln Arg Gln Gln Leu Leu Thr Glu Glu Ser Tyr Ala
    515                 520                 525

Leu Ser Cys Glu Ile Glu Ala Ala Ala Asp Ala Ser Thr Thr Ser Pro
    530                 535                 540

Lys Pro Arg Lys Ser Met Val Lys Arg Leu Ser Leu Leu Phe Leu Gly
545                 550                 555                 560

Ser Asp Met Ile Thr Ser Pro Thr Pro Thr Lys Glu Gln Pro Lys Ser
                565                 570                 575

Thr Ala Ser Gly Ser Ser Gly Glu Ser Met Asp Ser Val Ser Val Ser
            580                 585                 590

Ser Cys Glu Ser Asn His Ser Glu Ala Glu Glu Gly Ser Ile Thr Pro
        595                 600                 605

Met Asp Thr Pro Asp Glu Pro Gln Lys Lys Leu Ser Glu Ser Ser Ser
    610                 615                 620

Ser Cys Ser Ser Ile His Ser Met Asp Thr Asn Ser Ser Gly Met Ser
625                 630                 635                 640

Ser Leu Ile Asn Pro Leu Ser Ser Pro Pro Ser Cys Asn Asn Asn Pro
                645                 650                 655

Lys Ile His Lys Arg Ser Val Ser Val Thr Ser Ile Thr Ser Thr Val
            660                 665                 670

Leu Pro Pro Val Tyr Asn Gln Gln Asn Glu Asp Thr Cys Ile Ile Arg
        675                 680                 685

Ile Ser Val Glu Asp Asn Asn Gly Asn Met Tyr Lys Ser Ile Met Leu
    690                 695                 700

Thr Ser Gln Asp Lys Thr Pro Ala Val Ile Gln Arg Ala Met Leu Lys
705                 710                 715                 720

His Asn Leu Asp Ser Asp Pro Ala Glu Glu Tyr Glu Leu Val Gln Val
                725                 730                 735

Ile Ser Glu Asp Lys Glu Leu Val Ile Pro Asp Ser Ala Asn Val Phe
            740                 745                 750

Tyr Ala Met Asn Ser Gln Val Asn Phe Asp Phe Ile Leu Arg Lys Lys
        755                 760                 765

Asn Ser Met Glu Glu Gln Val Lys Leu Arg Ser Arg Thr Ser Leu Thr
    770                 775                 780

Leu Pro Arg Thr Ala Lys Arg Gly Cys Trp Ser Tyr Arg His Ser Lys
```

```
                              785                 790                 795                 800
Ile Thr Leu

<210> SEQ ID NO 56
<211> LENGTH: 162
<212> TYPE: PRT
<213> ORGANISM: Homo sapiens

<400> SEQUENCE: 56

Met Ala Ser Ser Val Asp Glu Glu Ala Leu His Gln Leu Tyr Leu Trp
  1               5                  10                  15

Val Asp Asn Ile Pro Leu Ser Arg Pro Lys Arg Asn Leu Ser Arg Asp
             20                  25                  30

Phe Ser Asp Gly Val Leu Val Ala Glu Val Ile Lys Phe Tyr Phe Pro
         35                  40                  45

Lys Met Val Glu Met His Asn Tyr Val Pro Ala Asn Ser Leu Gln Gln
 50                  55                  60

Lys Leu Ser Asn Trp Gly His Leu Asn Arg Lys Val Leu Lys Arg Leu
 65                  70                  75                  80

Asn Phe Ser Val Pro Asp Asp Val Met Arg Lys Ile Ala Gln Cys Ala
             85                  90                  95

Pro Gly Val Val Glu Leu Val Leu Ile Pro Leu Arg Gln Arg Leu Glu
            100                 105                 110

Glu Arg Gln Arg Arg Lys Gln Gly Ala Gly Ser Leu Gln Glu Leu
            115                 120                 125

Ala Pro Gln Asp Gly Ser Gly Tyr Met Asp Val Gly Lys Val Ala Phe
130                 135                 140

Ser Ile Ser Pro Ser Arg Leu Glu Leu Ser Phe Cys Pro Ser Cys
145                 150                 155                 160

His Leu

<210> SEQ ID NO 57
<211> LENGTH: 275
<212> TYPE: PRT
<213> ORGANISM: Homo sapiens

<400> SEQUENCE: 57

Met Ala Thr Glu Leu Glu Tyr Glu Ser Val Leu Cys Val Lys Pro Asp
  1               5                  10                  15

Val Ser Val Tyr Arg Ile Pro Pro Arg Ala Ser Asn Arg Gly Tyr Arg
             20                  25                  30

Ala Ser Asp Trp Lys Leu Asp Gln Pro Asp Trp Thr Gly Arg Leu Arg
         35                  40                  45

Ile Thr Ser Lys Gly Lys Thr Ala Tyr Ile Lys Leu Glu Asp Lys Val
 50                  55                  60

Ser Gly Glu Leu Phe Ala Gln Ala Pro Val Glu Gln Tyr Pro Gly Ile
 65                  70                  75                  80

Ala Val Glu Thr Val Thr Asp Ser Ser Arg Tyr Phe Val Ile Arg Ile
             85                  90                  95

Gln Asp Gly Thr Gly Arg Ser Ala Phe Ile Gly Ile Gly Phe Thr Asp
            100                 105                 110

Arg Gly Asp Ala Phe Asp Phe Asn Val Ser Leu Gln Asp His Phe Lys
            115                 120                 125

Trp Val Lys Gln Glu Ser Glu Ile Ser Lys Glu Ser Gln Glu Met Asp
            130                 135                 140
```

```
Ala Arg Pro Lys Leu Asp Leu Gly Phe Lys Glu Gly Gln Thr Ile Lys
145                 150                 155                 160

Leu Cys Ile Gly Asn Ile Thr Asn Lys Gly Gly Ala Ser Lys Pro
            165                 170                 175

Arg Thr Ala Arg Gly Gly Gly Leu Ser Leu Leu Pro Pro Pro Pro Gly
            180                 185                 190

Gly Lys Val Thr Ile Pro Pro Ser Ser Ser Val Ala Ile Ser Asn
            195                 200                 205

His Val Thr Pro Pro Ile Pro Lys Ser Asn His Gly Gly Ser Asp
            210                 215                 220

Ala Asp Ile Leu Leu Asp Leu Asp Ser Pro Ala Pro Val Thr Thr Pro
225                 230                 235                 240

Ala Pro Thr Pro Val Ser Val Ser Asn Asp Leu Trp Gly Asp Phe Ser
                245                 250                 255

Thr Ala Ser Ser Ser Val Pro Asn Gln Ala Pro Gln Pro Ser Asn Trp
                260                 265                 270

Val Gln Phe
        275

<210> SEQ ID NO 58
<211> LENGTH: 76
<212> TYPE: PRT
<213> ORGANISM: Homo sapiens

<400> SEQUENCE: 58

Met Ala Arg Gly Gln Gln Lys Ile Gln Ser Gln Gln Lys Asn Ala Lys
1               5                   10                  15

Lys Gln Ala Gly Gln Lys Lys Gln Gly His Asp Gln Lys Ala Ala
            20                  25                  30

Ala Lys Ala Ala Leu Ile Tyr Thr Cys Thr Val Cys Arg Thr Gln Met
            35                  40                  45

Pro Asp Pro Lys Thr Phe Lys Gln His Phe Glu Ser Lys His Pro Lys
        50                  55                  60

Thr Pro Leu Pro Pro Glu Leu Ala Asp Val Gln Ala
65                  70                  75

<210> SEQ ID NO 59
<211> LENGTH: 289
<212> TYPE: PRT
<213> ORGANISM: Homo sapiens

<400> SEQUENCE: 59

Met Pro Val Val Arg Lys Ile Phe Arg Arg Arg Gly Asp Ser Glu
1               5                   10                  15

Ser Glu Glu Asp Glu Gln Asp Ser Glu Glu Val Arg Leu Lys Leu Glu
            20                  25                  30

Glu Thr Arg Glu Val Gln Asn Leu Arg Lys Arg Pro Asn Gly Val Ser
            35                  40                  45

Ala Val Ala Leu Leu Val Gly Glu Lys Val Gln Glu Thr Thr Leu
            50                  55                  60

Val Asp Asp Pro Phe Gln Met Lys Thr Gly Gly Met Val Asp Met Lys
65                  70                  75                  80

Lys Leu Lys Glu Arg Gly Lys Asp Lys Ile Ser Glu Glu Asp Leu
            85                  90                  95

His Leu Gly Thr Ser Phe Ser Ala Glu Thr Asn Arg Arg Asp Glu Asp
            100                 105                 110
```

```
Ala Asp Met Met Lys Tyr Ile Glu Thr Glu Leu Lys Lys Arg Lys Gly
            115                 120                 125

Ile Val Glu His Glu Gln Lys Val Lys Pro Lys Asn Ala Glu Asp
        130                 135                 140

Cys Leu Tyr Glu Leu Pro Glu Asn Ile Arg Val Ser Ser Ala Lys Lys
145                 150                 155                 160

Thr Glu Glu Met Leu Ser Asn Gln Met Leu Ser Gly Ile Pro Glu Val
                165                 170                 175

Asp Leu Gly Ile Asp Ala Lys Ile Lys Asn Ile Ile Ser Thr Glu Asp
            180                 185                 190

Ala Lys Ala Arg Leu Leu Ala Glu Gln Gln Asn Lys Lys Lys Asp Ser
        195                 200                 205

Glu Thr Ser Phe Val Pro Thr Asn Met Ala Val Asn Tyr Val Gln His
        210                 215                 220

Asn Arg Phe Tyr His Glu Glu Leu Asn Ala Pro Ile Arg Arg Asn Lys
225                 230                 235                 240

Glu Glu Pro Lys Ala Arg Pro Leu Arg Val Gly Asp Thr Glu Lys Pro
                245                 250                 255

Glu Pro Glu Arg Ser Pro Pro Asn Arg Lys Arg Pro Ala Asn Glu Lys
            260                 265                 270

Ala Thr Asp Asp Tyr His Tyr Glu Lys Phe Lys Lys Met Asn Arg Arg
        275                 280                 285

Tyr

<210> SEQ ID NO 60
<211> LENGTH: 153
<212> TYPE: PRT
<213> ORGANISM: Homo sapiens

<400> SEQUENCE: 60

Met Pro Tyr Val Phe Ser Phe Lys Met Pro Gln Glu Gln Gly Gln Met
1               5                   10                  15

Phe Gln Tyr Tyr Pro Val Tyr Met Val Leu Pro Trp Glu Gln Pro Gln
            20                  25                  30

Gln Thr Val Pro Arg Ser Pro Gln Gln Thr Arg Gln Gln Gln Tyr Glu
        35                  40                  45

Glu Gln Ile Pro Phe Tyr Ala Gln Phe Gly Tyr Ile Pro Gln Leu Ala
    50                  55                  60

Glu Pro Ala Ile Ser Gly Gly Gln Gln Leu Ala Phe Asp Pro Gln
65                  70                  75                  80

Leu Gly Thr Ala Pro Glu Ile Ala Val Met Ser Thr Gly Glu Glu Ile
                85                  90                  95

Pro Tyr Leu Gln Lys Glu Ala Ile Asn Phe Arg His Asp Ser Ala Gly
            100                 105                 110

Val Phe Met Pro Ser Thr Ser Pro Lys Pro Ser Thr Thr Asn Val Phe
        115                 120                 125

Thr Ser Ala Val Asp Gln Thr Ile Thr Pro Glu Leu Pro Glu Glu Lys
    130                 135                 140

Asp Lys Thr Asp Ser Leu Arg Glu Pro
145                 150

<210> SEQ ID NO 61
<211> LENGTH: 386
<212> TYPE: PRT
<213> ORGANISM: Homo sapiens
```

<400> SEQUENCE: 61

```
Met Thr Ser Leu Phe Arg Arg Ser Ser Gly Ser Gly Gly Gly Gly
1               5                   10                  15

Thr Ala Gly Ala Arg Gly Gly Gly Gly Thr Ala Ala Pro Gln Glu
            20                  25                  30

Leu Asn Asn Ser Arg Pro Ala Arg Gln Val Arg Arg Leu Glu Phe Asn
        35                  40                  45

Gln Ala Met Asp Asp Phe Lys Thr Met Phe Pro Asn Met Asp Tyr Asp
    50                  55                  60

Ile Ile Glu Cys Val Leu Arg Ala Asn Ser Gly Ala Val Asp Ala Thr
65                  70                  75                  80

Ile Asp Gln Leu Leu Gln Met Asn Leu Glu Gly Gly Ser Ser Gly
                85                  90                  95

Gly Val Tyr Glu Asp Ser Ser Asp Ser Glu Asp Ser Ile Pro Pro Glu
            100                 105                 110

Ile Leu Glu Arg Thr Leu Glu Pro Asp Ser Ser Asp Glu Glu Pro Pro
        115                 120                 125

Pro Val Tyr Ser Pro Pro Ala Tyr His Met His Val Phe Asp Arg Pro
    130                 135                 140

Tyr Pro Leu Ala Pro Pro Thr Pro Pro Arg Ile Asp Ala Leu Gly
145                 150                 155                 160

Ser Gly Ala Pro Thr Ser Gln Arg Arg Tyr Arg Asn Trp Asn Pro Pro
            165                 170                 175

Leu Leu Gly Asn Leu Pro Asp Asp Phe Leu Arg Ile Leu Pro Gln Gln
        180                 185                 190

Leu Asp Ser Ile Gln Gly Asn Ala Gly Gly Pro Lys Pro Gly Ser Gly
    195                 200                 205

Glu Gly Cys Pro Pro Ala Met Ala Gly Pro Gly Pro Gly Asp Gln Glu
210                 215                 220

Ser Arg Trp Lys Gln Tyr Leu Glu Asp Glu Arg Ile Ala Leu Phe Leu
225                 230                 235                 240

Gln Asn Glu Glu Phe Met Lys Glu Leu Gln Arg Asn Arg Asp Phe Leu
            245                 250                 255

Leu Ala Leu Glu Arg Asp Arg Leu Lys Tyr Glu Ser Gln Lys Ser Lys
        260                 265                 270

Ser Ser Ser Val Ala Val Gly Asn Asp Phe Gly Phe Ser Ser Pro Val
    275                 280                 285

Pro Gly Thr Gly Asp Ala Asn Pro Ala Val Ser Glu Asp Ala Leu Phe
290                 295                 300

Arg Asp Lys Leu Lys His Met Gly Lys Ser Thr Arg Arg Lys Leu Phe
305                 310                 315                 320

Glu Leu Ala Arg Ala Phe Ser Glu Lys Thr Lys Met Arg Lys Ser Lys
            325                 330                 335

Arg Lys His Leu Leu Lys His Gln Ser Leu Gly Ala Ala Ala Ser Thr
        340                 345                 350

Ala Asn Leu Leu Asp Asp Val Glu Gly His Ala Cys Asp Glu Asp Phe
    355                 360                 365

Arg Gly Arg Arg Gln Glu Ala Pro Lys Val Glu Glu Gly Leu Arg Glu
370                 375                 380

Gly Gln
385
```

<210> SEQ ID NO 62

<211> LENGTH: 329
<212> TYPE: PRT
<213> ORGANISM: Homo sapiens

<400> SEQUENCE: 62

Met Ala Ala Gln Tyr Gly Ser Met Ser Phe Asn Pro Ser Thr Pro Gly
1               5                   10                  15

Ala Ser Tyr Gly Pro Gly Arg Gln Glu Pro Arg Asn Ser Gln Leu Arg
            20                  25                  30

Ile Val Leu Val Gly Lys Thr Gly Ala Gly Lys Ser Ala Thr Gly Asn
        35                  40                  45

Ser Ile Leu Gly Arg Lys Val Phe His Ser Gly Thr Ala Ala Lys Ser
50                  55                  60

Ile Thr Lys Lys Cys Glu Lys Arg Ser Ser Ser Trp Lys Glu Thr Glu
65                  70                  75                  80

Leu Val Val Val Asp Thr Pro Gly Ile Phe Asp Thr Glu Val Pro Asn
                85                  90                  95

Ala Glu Thr Ser Lys Glu Ile Ile Arg Cys Ile Leu Leu Thr Ser Pro
            100                 105                 110

Gly Pro His Ala Leu Leu Leu Val Val Pro Leu Gly Arg Tyr Thr Glu
        115                 120                 125

Glu Glu His Lys Ala Thr Glu Lys Ile Leu Lys Met Phe Gly Glu Arg
130                 135                 140

Ala Arg Ser Phe Met Ile Leu Ile Phe Thr Arg Lys Asp Asp Leu Gly
145                 150                 155                 160

Asp Thr Asn Leu His Asp Tyr Leu Arg Glu Ala Pro Glu Asp Ile Gln
                165                 170                 175

Asp Leu Met Asp Ile Phe Gly Asp Arg Tyr Cys Ala Leu Asn Asn Lys
            180                 185                 190

Ala Thr Gly Ala Glu Gln Glu Ala Gln Arg Ala Gln Leu Leu Gly Leu
        195                 200                 205

Ile Gln Arg Val Val Arg Glu Asn Lys Glu Gly Cys Tyr Thr Asn Arg
210                 215                 220

Met Tyr Gln Arg Ala Glu Glu Ile Gln Lys Gln Thr Gln Ala Met
225                 230                 235                 240

Gln Glu Leu His Arg Val Glu Leu Glu Arg Glu Lys Ala Arg Ile Arg
                245                 250                 255

Glu Glu Tyr Glu Glu Lys Ile Arg Lys Leu Glu Asp Lys Val Glu Gln
            260                 265                 270

Glu Lys Arg Lys Lys Gln Met Glu Lys Lys Leu Ala Glu Gln Glu Ala
        275                 280                 285

His Tyr Ala Val Arg Gln Gln Arg Ala Arg Thr Glu Val Glu Ser Lys
290                 295                 300

Asp Gly Ile Leu Glu Leu Ile Met Thr Ala Leu Gln Ile Ala Ser Phe
305                 310                 315                 320

Ile Leu Leu Arg Leu Phe Ala Glu Asp
                325

<210> SEQ ID NO 63
<211> LENGTH: 78
<212> TYPE: PRT
<213> ORGANISM: Homo sapiens

<400> SEQUENCE: 63

Met Ser Glu Val Leu Pro Tyr Gly Asp Glu Lys Leu Ser Pro Tyr Gly
1               5                   10                  15

```
Asp Gly Gly Asp Val Gly Gln Ile Phe Ser Cys Arg Leu Gln Asp Thr
            20                  25                  30

Asn Asn Phe Phe Gly Ala Gly Gln Asn Lys Arg Pro Pro Lys Leu Gly
        35                  40                  45

Gln Ile Gly Arg Ser Lys Arg Val Val Ile Glu Asp Asp Arg Ile Asp
 50                  55                  60

Asp Val Leu Lys Asn Met Thr Asp Lys Ala Pro Pro Gly Val
 65                  70                  75
```

<210> SEQ ID NO 64
<211> LENGTH: 686
<212> TYPE: PRT
<213> ORGANISM: Homo sapiens

<400> SEQUENCE: 64

```
Met Lys Ile Val Ile Arg Gly Asp Arg Asn Thr Gly Lys Thr Ala Leu
 1               5                  10                  15

Trp His Arg Leu Gln Gly Arg Pro Phe Val Glu Glu Tyr Ile Pro Thr
            20                  25                  30

Gln Glu Ile Gln Val Thr Ser Ile His Trp Ser Tyr Lys Thr Thr Asp
        35                  40                  45

Asp Ile Val Lys Val Glu Val Trp Asp Val Val Asp Lys Gly Lys Cys
 50                  55                  60

Lys Lys Arg Gly Asp Gly Leu Lys Met Glu Asn Asp Pro Gln Glu Ala
 65                  70                  75                  80

Glu Ser Glu Met Ala Leu Asp Ala Glu Phe Leu Asp Val Tyr Lys Asn
                85                  90                  95

Cys Asn Gly Val Val Met Met Phe Asp Ile Thr Lys Gln Trp Thr Phe
            100                 105                 110

Asn Tyr Ile Leu Arg Glu Leu Pro Lys Val Pro Thr His Val Pro Val
        115                 120                 125

Cys Val Leu Gly Asn Tyr Arg Asp Met Gly Glu His Arg Val Ile Leu
130                 135                 140

Pro Asp Asp Val Arg Asp Phe Ile Asp Asn Leu Asp Arg Pro Pro Gly
145                 150                 155                 160

Ser Ser Tyr Phe Arg Tyr Ala Glu Ser Ser Met Lys Asn Ser Phe Gly
                165                 170                 175

Leu Lys Tyr Leu His Lys Phe Phe Asn Ile Pro Phe Leu Gln Leu Gln
            180                 185                 190

Arg Glu Thr Leu Leu Arg Gln Leu Glu Thr Asn Gln Leu Asp Met Asp
        195                 200                 205

Ala Thr Leu Glu Glu Leu Ser Val Gln Gln Glu Thr Glu Asp Gln Asn
210                 215                 220

Tyr Gly Ile Phe Leu Glu Met Met Glu Ala Arg Ser Arg Gly His Ala
225                 230                 235                 240

Ser Pro Leu Ala Ala Asn Gly Gln Ser Pro Ser Pro Gly Ser Gln Ser
                245                 250                 255

Pro Val Val Pro Ala Gly Ala Val Ser Thr Gly Ser Ser Pro Gly
            260                 265                 270

Thr Pro Gln Pro Ala Pro Gln Leu Pro Leu Asn Ala Ala Pro Pro Ser
        275                 280                 285

Ser Val Pro Pro Val Pro Ser Glu Ala Leu Pro Pro Ala Cys
290                 295                 300

Pro Ser Ala Pro Ala Pro Arg Arg Ser Ile Ile Ser Arg Leu Phe Gly
```

```
            305                 310                 315                 320
        Thr Ser Pro Ala Thr Glu Ala Ala Pro Pro Pro Glu Pro Val Pro
                        325                 330                 335
        Ala Ala Glu Gly Pro Ala Thr Val Gln Ser Val Glu Asp Phe Val Pro
                    340                 345                 350
        Asp Asp Arg Leu Asp Arg Ser Phe Leu Glu Asp Thr Thr Pro Ala Arg
                    355                 360                 365
        Asp Glu Lys Lys Val Gly Ala Lys Ala Ala Gln Gln Asp Ser Asp Ser
                370                 375                 380
        Asp Gly Glu Ala Leu Gly Gly Asn Pro Met Val Ala Gly Phe Gln Asp
        385                 390                 395                 400
        Asp Val Asp Leu Glu Asp Gln Pro Arg Gly Ser Pro Leu Pro Ala
                    405                 410                 415
        Gly Pro Val Pro Ser Gln Asp Ile Thr Leu Ser Ser Glu Glu Ala
                420                 425                 430
        Glu Val Ala Ala Pro Thr Lys Gly Pro Ala Pro Ala Pro Gln Gln Cys
                    435                 440                 445
        Ser Glu Pro Glu Thr Lys Trp Ser Ser Ile Pro Ala Ser Lys Pro Arg
                450                 455                 460
        Arg Gly Thr Ala Pro Thr Arg Thr Ala Ala Pro Pro Trp Pro Gly Gly
        465                 470                 475                 480
        Val Ser Val Arg Thr Gly Pro Glu Lys Arg Ser Ser Thr Arg Pro Pro
                    485                 490                 495
        Ala Glu Met Glu Pro Gly Lys Gly Glu Gln Ala Ser Ser Ser Glu Ser
                    500                 505                 510
        Asp Pro Glu Gly Pro Ile Ala Ala Gln Met Leu Ser Phe Val Met Asp
                515                 520                 525
        Asp Pro Asp Phe Glu Ser Glu Gly Ser Asp Thr Gln Arg Arg Ala Asp
                530                 535                 540
        Asp Phe Pro Val Arg Asp Asp Pro Ser Asp Val Thr Asp Glu Asp Glu
        545                 550                 555                 560
        Gly Pro Ala Glu Pro Pro Pro Pro Lys Leu Pro Leu Pro Ala Phe
                    565                 570                 575
        Arg Leu Lys Asn Asp Ser Asp Leu Phe Gly Leu Gly Leu Glu Glu Ala
                    580                 585                 590
        Gly Pro Lys Glu Ser Ser Glu Glu Gly Lys Glu Gly Lys Thr Pro Ser
                    595                 600                 605
        Lys Glu Lys Lys Lys Lys Lys Lys Gly Lys Glu Glu Glu Glu Lys
                610                 615                 620
        Ala Ala Lys Lys Lys Ser Lys His Lys Lys Ser Lys Asp Lys Glu Glu
        625                 630                 635                 640
        Gly Lys Glu Glu Arg Arg Arg Gln Gln Arg Pro Pro Arg Ser Arg
                    645                 650                 655
        Glu Arg Thr Ala Ala Asp Glu Leu Glu Ala Phe Leu Gly Gly Gly Ala
                    660                 665                 670
        Pro Gly Gly Arg His Pro Gly Gly Gly Asp Tyr Glu Glu Leu
                    675                 680                 685

<210> SEQ ID NO 65
<211> LENGTH: 376
<212> TYPE: PRT
<213> ORGANISM: Homo sapiens

<400> SEQUENCE: 65
```

```
Met Ser Asp Glu Val Phe Ser Thr Thr Leu Ala Tyr Thr Lys Ser Pro
1               5                   10                  15

Lys Val Thr Lys Arg Thr Thr Phe Gln Asp Glu Leu Ile Arg Ala Ile
            20                  25                  30

Thr Ala Arg Ser Ala Arg Gln Arg Ser Ser Glu Tyr Ser Asp Asp Phe
        35                  40                  45

Asp Ser Asp Glu Ile Val Ser Leu Gly Asp Phe Ser Asp Thr Ser Ala
    50                  55                  60

Asp Glu Asn Ser Val Asn Lys Lys Met Asn Asp Phe His Ile Ser Asp
65                  70                  75                  80

Asp Glu Glu Lys Asn Pro Ser Lys Leu Leu Phe Leu Lys Thr Asn Lys
                85                  90                  95

Ser Asn Gly Asn Ile Thr Lys Asp Glu Pro Val Cys Ala Ile Lys Asn
                100                 105                 110

Glu Glu Glu Met Ala Pro Asp Gly Cys Glu Asp Ile Val Val Lys Ser
                115                 120                 125

Phe Ser Glu Ser Gln Asn Lys Asp Glu Glu Phe Glu Lys Asp Lys Ile
    130                 135                 140

Lys Met Lys Pro Lys Pro Arg Ile Leu Ser Ile Lys Ser Thr Ser Ser
145                 150                 155                 160

Ala Glu Asn Asn Ser Leu Asp Thr Asp Asp His Phe Lys Pro Ser Pro
                165                 170                 175

Trp Pro Arg Ser Met Leu Lys Lys Ser His Met Glu Glu Lys Asp
                180                 185                 190

Gly Leu Glu Asp Lys Glu Thr Ala Leu Ser Glu Glu Leu Glu Leu His
    195                 200                 205

Ser Ala Pro Ser Ser Leu Pro Thr Pro Asn Gly Ile Gln Leu Glu Ala
    210                 215                 220

Glu Lys Lys Ala Phe Ser Glu Asn Leu Asp Pro Glu Asp Ser Cys Leu
225                 230                 235                 240

Thr Ser Leu Ala Ser Ser Leu Lys Gln Ile Leu Gly Asp Ser Phe
                245                 250                 255

Ser Pro Gly Ser Glu Gly Asn Ala Ser Gly Lys Asp Pro Asn Glu Glu
    260                 265                 270

Ile Thr Glu Asn His Asn Ser Leu Lys Ser Asp Glu Asn Lys Glu Asn
    275                 280                 285

Ser Phe Ser Ala Asp His Val Thr Thr Ala Val Glu Lys Ser Lys Glu
    290                 295                 300

Ser Gln Val Thr Ala Asp Asp Leu Glu Glu Lys Ala Lys Ala Glu
305                 310                 315                 320

Leu Ile Met Asp Asp Asp Arg Thr Val Asp Pro Leu Leu Ser Lys Ser
                325                 330                 335

Gln Ser Ile Leu Ile Ser Thr Ser Ala Thr Ala Ser Ser Lys Lys Thr
    340                 345                 350

Ile Glu Asp Arg Asn Ile Lys Asn Lys Ser Thr Asn Asn Arg Ala
    355                 360                 365

Ser Ser Ala Ser Ala Arg Ser Gly
    370                 375
```

<210> SEQ ID NO 66
<211> LENGTH: 441
<212> TYPE: PRT
<213> ORGANISM: Homo sapiens

<400> SEQUENCE: 66

```
Met Lys Lys Phe Phe Gln Glu Phe Lys Ala Asp Ile Lys Phe Lys Ser
1               5                   10                  15

Ala Gly Pro Gly Gln Lys Leu Lys Glu Ser Val Gly Glu Lys Ala His
            20                  25                  30

Lys Glu Lys Pro Asn Gln Pro Ala Pro Arg Pro Pro Arg Gln Gly Pro
                35                  40                  45

Thr Asn Glu Ala Gln Met Ala Ala Ala Ala Leu Ala Arg Leu Glu
    50                  55                  60

Gln Lys Gln Ser Arg Ala Trp Gly Pro Thr Ser Gln Asp Thr Ile Arg
65                  70                  75                  80

Asn Gln Val Arg Lys Glu Leu Gln Ala Glu Ala Thr Val Ser Gly Ser
                85                  90                  95

Pro Glu Ala Pro Gly Thr Asn Val Val Ser Glu Pro Arg Glu Glu Gly
                100                 105                 110

Ser Ala His Leu Ala Val Pro Gly Val Tyr Phe Thr Cys Pro Leu Thr
                115                 120                 125

Gly Ala Thr Leu Arg Lys Asp Gln Arg Asp Ala Cys Ile Lys Glu Ala
            130                 135                 140

Ile Leu Leu His Phe Ser Thr Asp Pro Val Ala Ala Ser Ile Met Lys
145                 150                 155                 160

Ile Tyr Thr Phe Asn Lys Asp Gln Asp Arg Val Lys Leu Gly Val Asp
                165                 170                 175

Thr Ile Ala Lys Tyr Leu Asp Asn Ile His Leu His Pro Glu Glu Glu
            180                 185                 190

Lys Tyr Arg Lys Ile Lys Leu Gln Asn Lys Val Phe Gln Glu Arg Ile
            195                 200                 205

Asn Cys Leu Glu Gly Thr His Glu Phe Phe Glu Ala Ile Gly Phe Gln
210                 215                 220

Lys Val Leu Leu Pro Ala Gln Asp Gln Glu Asp Pro Glu Glu Phe Tyr
225                 230                 235                 240

Val Leu Ser Glu Thr Thr Leu Ala Gln Pro Gln Ser Leu Glu Arg His
                245                 250                 255

Lys Glu Gln Leu Leu Ala Ala Glu Pro Val Arg Ala Lys Leu Asp Arg
                260                 265                 270

Gln Arg Arg Val Phe Gln Pro Ser Pro Leu Ala Ser Gln Phe Glu Leu
            275                 280                 285

Pro Gly Asp Phe Phe Asn Leu Thr Ala Glu Glu Ile Lys Arg Glu Gln
            290                 295                 300

Arg Leu Arg Ser Glu Ala Val Glu Arg Leu Ser Val Leu Arg Thr Lys
305                 310                 315                 320

Ala Met Arg Glu Lys Glu Glu Gln Arg Gly Leu Arg Lys Tyr Asn Tyr
                325                 330                 335

Thr Leu Leu Arg Val Arg Leu Pro Asp Gly Cys Leu Leu Gln Gly Thr
            340                 345                 350

Phe Tyr Ala Arg Glu Arg Leu Gly Ala Val Tyr Gly Phe Val Arg Glu
                355                 360                 365

Ala Leu Gln Ser Asp Trp Leu Pro Phe Glu Leu Leu Ala Ser Gly Gly
            370                 375                 380

Gln Lys Leu Ser Glu Asp Glu Asn Leu Ala Leu Asn Glu Cys Gly Leu
385                 390                 395                 400

Val Pro Ser Ala Leu Leu Thr Phe Ser Trp Asp Met Ala Val Leu Glu
                405                 410                 415
```

Asp Ile Lys Ala Ala Gly Ala Glu Pro Asp Ser Ile Leu Lys Pro Glu
        420                 425                 430

Leu Leu Ser Ala Ile Glu Lys Leu Leu
        435                 440

<210> SEQ ID NO 67
<211> LENGTH: 204
<212> TYPE: PRT
<213> ORGANISM: Homo sapiens

<400> SEQUENCE: 67

Met Glu Ala Ala Gly Ser Pro Ala Ala Thr Glu Thr Gly Lys Tyr Ile
1               5                   10                  15

Ala Ser Thr Gln Arg Pro Asp Gly Thr Trp Arg Lys Gln Arg Arg Val
            20                  25                  30

Lys Glu Gly Tyr Val Pro Gln Glu Glu Val Pro Val Tyr Glu Asn Lys
        35                  40                  45

Tyr Val Lys Phe Phe Lys Ser Lys Pro Glu Leu Pro Pro Gly Leu Ser
    50                  55                  60

Pro Glu Ala Thr Ala Pro Val Thr Pro Ser Arg Pro Glu Gly Gly Glu
65                  70                  75                  80

Pro Gly Leu Ser Lys Thr Ala Lys Arg Asn Leu Lys Arg Lys Glu Lys
                85                  90                  95

Arg Arg Gln Gln Gln Glu Lys Gly Glu Ala Glu Ala Leu Ser Arg Thr
            100                 105                 110

Leu Asp Lys Val Ser Leu Glu Glu Thr Ala Gln Leu Pro Ser Ala Pro
        115                 120                 125

Gln Gly Ser Arg Ala Ala Pro Thr Ala Ala Ser Asp Gln Pro Asp Ser
    130                 135                 140

Ala Ala Thr Thr Glu Lys Ala Lys Lys Ile Lys Asn Leu Lys Lys Lys
145                 150                 155                 160

Leu Arg Gln Val Glu Glu Leu Gln Gln Arg Ile Gln Ala Gly Glu Val
                165                 170                 175

Ser Gln Pro Ser Lys Glu Gln Leu Glu Lys Leu Ala Arg Arg Arg Ala
            180                 185                 190

Leu Glu Glu Glu Leu Glu Asp Leu Glu Leu Gly Leu
        195                 200

<210> SEQ ID NO 68
<211> LENGTH: 190
<212> TYPE: PRT
<213> ORGANISM: Homo sapiens

<400> SEQUENCE: 68

Met Ala Ser Arg Gly Lys Thr Glu Thr Ser Lys Leu Lys Gln Asn Leu
1               5                   10                  15

Glu Glu Gln Leu Asp Arg Leu Met Gln Gln Leu Gln Asp Leu Glu Glu
            20                  25                  30

Cys Arg Glu Glu Leu Asp Thr Asp Glu Tyr Glu Glu Thr Lys Lys Glu
        35                  40                  45

Thr Leu Glu Gln Leu Ser Glu Phe Asn Asp Ser Leu Lys Lys Ile Met
    50                  55                  60

Ser Gly Asn Met Thr Leu Val Asp Glu Leu Ser Gly Met Gln Leu Ala
65                  70                  75                  80

Ile Gln Ala Ala Ile Ser Gln Ala Phe Lys Thr Pro Glu Val Ile Arg
                85                  90                  95

```
Leu Phe Ala Lys Lys Gln Pro Gly Gln Leu Arg Thr Arg Leu Ala Glu
            100                 105                 110

Met Asp Arg Asp Leu Met Val Gly Lys Leu Glu Arg Asp Leu Tyr Thr
        115                 120                 125

Gln Gln Lys Val Glu Ile Leu Thr Ala Leu Arg Lys Leu Gly Glu Lys
130                 135                 140

Leu Thr Ala Asp Asp Glu Ala Phe Leu Ser Ala Asn Ala Gly Ala Ile
145                 150                 155                 160

Leu Ser Gln Phe Glu Lys Val Ser Thr Asp Leu Gly Ser Gly Asp Lys
                165                 170                 175

Ile Leu Ala Leu Ala Ser Phe Glu Val Glu Lys Thr Lys Lys
            180                 185                 190

<210> SEQ ID NO 69
<211> LENGTH: 194
<212> TYPE: PRT
<213> ORGANISM: Homo sapiens

<400> SEQUENCE: 69

Met Ala Pro Lys Lys Asp Val Lys Pro Val Ala Ala Ala Ala Ala Ala
1               5                   10                  15

Ala Pro Ala Pro Ala Pro Ala Pro Ala Pro Ala Pro Ala Pro Ala Lys
            20                  25                  30

Pro Lys Glu Glu Lys Ile Asp Leu Ser Ala Ile Lys Ile Glu Phe Ser
        35                  40                  45

Lys Glu Gln Gln Asp Glu Phe Lys Glu Ala Phe Leu Leu Phe Asp Arg
    50                  55                  60

Thr Gly Asp Ser Lys Ile Thr Leu Ser Gln Val Gly Asp Val Leu Arg
65                  70                  75                  80

Ala Leu Gly Thr Asn Pro Thr Asn Ala Glu Val Arg Lys Val Leu Gly
                85                  90                  95

Asn Pro Ser Asn Glu Glu Leu Asn Ala Lys Lys Ile Glu Phe Glu Gln
            100                 105                 110

Phe Leu Pro Met Met Gln Ala Ile Ser Asn Asn Lys Asp Gln Ala Thr
        115                 120                 125

Tyr Glu Asp Phe Val Glu Gly Leu Arg Val Phe Asp Lys Glu Gly Asn
    130                 135                 140

Gly Thr Val Met Gly Ala Glu Leu Arg His Val Leu Ala Thr Leu Gly
145                 150                 155                 160

Glu Lys Met Lys Glu Glu Glu Val Glu Ala Leu Met Ala Gly Gln Glu
                165                 170                 175

Asp Ser Asn Gly Cys Ile Asn Tyr Glu Ala Phe Val Lys His Ile Met
            180                 185                 190

Ser Ile

<210> SEQ ID NO 70
<211> LENGTH: 227
<212> TYPE: PRT
<213> ORGANISM: Homo sapiens

<400> SEQUENCE: 70

Met Glu Lys Leu Phe Asn Glu Asn Glu Gly Met Pro Ser Asn Gln Gly
1               5                   10                  15

Lys Ile Asp Asn Glu Glu Gln Pro Pro His Glu Gly Lys Pro Glu Val
            20                  25                  30

Ala Cys Ile Leu Glu Asp Lys Lys Leu Glu Asn Glu Gly Asn Thr Glu
```

```
                35                  40                  45
Asn Thr Gly Lys Arg Val Glu Glu Pro Leu Lys Asp Lys Glu Lys Pro
    50                  55                  60
Glu Ser Ala Gly Lys Ala Lys Gly Glu Gly Lys Ser Glu Arg Lys Gly
65                  70                  75                  80
Lys Ser Glu Met Gln Gly Gly Ser Lys Thr Glu Gly Lys Pro Glu Arg
                85                  90                  95
Gly Gly Arg Ala Glu Gly Glu Gly Glu Pro Asp Ser Glu Arg Glu Pro
            100                 105                 110
Glu Ser Glu Gly Glu Pro Glu Ser Glu Thr Arg Ala Ala Gly Lys Arg
        115                 120                 125
Pro Ala Glu Asp Asp Ile Pro Arg Lys Ala Lys Arg Lys Thr Asn Lys
    130                 135                 140
Gly Leu Ala Gln Tyr Leu Lys Gln Tyr Lys Ala Ile His Asp Met
145                 150                 155                 160
Asn Phe Ser Asn Glu Asp Met Ile Arg Glu Phe Asp Asn Met Ala Arg
                165                 170                 175
Val Glu Asp Lys Arg Arg Lys Ser Lys Gln Lys Leu Gly Ala Phe Leu
            180                 185                 190
Trp Met Gln Arg Asn Leu Gln Asp Pro Phe Tyr Pro Arg Gly Pro Arg
        195                 200                 205
Glu Phe Arg Gly Gly Cys Arg Ala Pro Arg Arg Asp Thr Glu Asp Ile
    210                 215                 220
Pro Tyr Val
225

<210> SEQ ID NO 71
<211> LENGTH: 109
<212> TYPE: PRT
<213> ORGANISM: Homo sapiens

<400> SEQUENCE: 71

Met Ala Lys Gln Pro Ser Asp Val Ser Ser Glu Cys Asp Arg Glu Gly
1               5                   10                  15
Arg Gln Leu Gln Pro Ala Glu Arg Pro Pro Gln Leu Arg Pro Gly Ala
            20                  25                  30
Pro Thr Ser Leu Gln Thr Glu Pro Gln Asp Arg Ser Pro Ala Pro Met
        35                  40                  45
Ser Cys Asp Lys Ser Thr Gln Thr Pro Ser Pro Pro Cys Gln Ala Phe
    50                  55                  60
Asn His Tyr Leu Ser Ala Met Ala Ser Met Arg Gln Ala Glu Pro Ala
65                  70                  75                  80
Asp Met Arg Pro Glu Ile Trp Ile Ala Gln Glu Leu Arg Arg Ile Gly
                85                  90                  95
Asp Glu Phe Asn Ala Tyr Tyr Ala Arg Arg Leu Glu Lys
            100                 105

<210> SEQ ID NO 72
<211> LENGTH: 363
<212> TYPE: PRT
<213> ORGANISM: Homo sapiens

<400> SEQUENCE: 72

Met Ala Asp Thr Asp Leu Phe Met Glu Cys Glu Glu Glu Glu Leu Glu
1               5                   10                  15
Pro Trp Gln Lys Ile Ser Asp Val Ile Glu Asp Ser Val Val Glu Asp
```

```
            20                  25                  30

Tyr Asn Ser Val Asp Lys Thr Thr Val Ser Val Ser Gln Gln Pro
            35                  40                  45

Val Ser Ala Pro Val Pro Ile Ala His Ala Ser Val Ala Gly His
        50                  55                  60

Leu Ser Thr Ser Thr Thr Val Ser Ser Gly Ala Gln Asn Ser Asp
 65                  70                  75                  80

Ser Thr Lys Lys Thr Leu Val Thr Leu Ile Ala Asn Asn Ala Gly
                85                  90                  95

Asn Pro Leu Val Gln Gln Gly Gly Gln Pro Leu Ile Leu Thr Gln Asn
            100                 105                 110

Pro Ala Pro Gly Leu Gly Thr Met Val Thr Gln Pro Val Leu Arg Pro
        115                 120                 125

Val Gln Val Met Gln Asn Ala Asn His Val Thr Ser Ser Pro Val Ala
        130                 135                 140

Ser Gln Pro Ile Phe Ile Thr Thr Gln Gly Phe Pro Val Arg Asn Val
145                 150                 155                 160

Arg Pro Val Gln Asn Ala Met Asn Gln Val Gly Ile Val Leu Asn Val
                165                 170                 175

Gln Gln Gly Gln Thr Val Arg Pro Ile Thr Leu Val Pro Ala Pro Gly
            180                 185                 190

Thr Gln Phe Val Lys Pro Thr Val Gly Val Pro Gln Val Phe Ser Gln
        195                 200                 205

Met Thr Pro Val Arg Pro Gly Ser Thr Met Pro Val Arg Pro Thr Thr
    210                 215                 220

Asn Thr Phe Thr Thr Val Ile Pro Ala Thr Leu Thr Ile Arg Ser Thr
225                 230                 235                 240

Val Pro Gln Ser Gln Ser Gln Gln Thr Lys Ser Thr Pro Ser Thr Ser
                245                 250                 255

Thr Thr Pro Thr Ala Thr Gln Pro Thr Ser Leu Gly Gln Leu Ala Val
            260                 265                 270

Gln Ser Pro Gly Gln Ser Asn Gln Thr Thr Asn Pro Lys Leu Ala Pro
        275                 280                 285

Ser Phe Pro Ser Pro Pro Ala Val Ser Ile Ala Ser Phe Val Thr Val
    290                 295                 300

Lys Arg Pro Gly Val Thr Gly Glu Asn Ser Asn Glu Val Ala Lys Leu
305                 310                 315                 320

Val Asn Thr Leu Asn Thr Ile Pro Ser Leu Gly Gln Ser Pro Gly Pro
                325                 330                 335

Val Val Val Ser Asn Asn Ser Ser Ala His Gly Ser Gln Arg Thr Ser
            340                 345                 350

Gly Pro Glu Ser Ser Met Lys Gly Thr Ile Thr
        355                 360

<210> SEQ ID NO 73
<211> LENGTH: 182
<212> TYPE: PRT
<213> ORGANISM: Homo sapiens

<400> SEQUENCE: 73

Met Ala Asp Ser Glu Asn Gln Gly Pro Ala Glu Pro Ser Gln Ala Ala
 1               5                  10                  15

Ala Ala Ala Glu Ala Ala Ala Glu Glu Val Met Ala Glu Gly Gly Ala
            20                  25                  30
```

```
Gln Gly Gly Asp Cys Asp Ser Ala Ala Gly Asp Pro Asp Ser Ala Ala
            35                  40                  45

Gly Gln Met Ala Glu Glu Pro Gln Thr Pro Ala Glu Asn Ala Pro Lys
 50                  55                  60

Pro Lys Asn Asp Phe Ile Glu Ser Leu Pro Asn Ser Val Lys Cys Arg
 65                  70                  75                  80

Val Leu Ala Leu Lys Lys Leu Gln Lys Arg Cys Asp Lys Ile Glu Ala
                 85                  90                  95

Lys Phe Asp Lys Glu Phe Gln Ala Leu Glu Lys Lys Tyr Asn Asp Ile
            100                 105                 110

Tyr Lys Pro Leu Leu Ala Lys Ile Gln Glu Leu Thr Gly Glu Met Glu
        115                 120                 125

Gly Cys Ala Trp Thr Leu Glu Gly Glu Glu Glu Glu Glu Glu Glu Tyr
130                 135                 140

Glu Asp Asp Glu Glu Gly Glu Asp Glu Glu Glu Glu Ala Ala
145                 150                 155                 160

Ala Glu Ala Ala Ala Gly Ala Lys His Asp Asp Ala His Ala Glu Met
                165                 170                 175

Pro Asp Asp Ala Lys Lys
            180

<210> SEQ ID NO 74
<211> LENGTH: 365
<212> TYPE: PRT
<213> ORGANISM: Homo sapiens

<400> SEQUENCE: 74

Met Asp Gly Pro Ala Glu Pro Gln Ile Pro Gly Leu Trp Asp Thr Tyr
 1                   5                  10                  15

Glu Asp Asp Ile Ser Glu Ile Ser Gln Lys Leu Pro Gly Glu Tyr Phe
                 20                  25                  30

Arg Tyr Lys Gly Val Pro Phe Pro Val Gly Leu Tyr Ser Leu Glu Ser
            35                  40                  45

Ile Ser Leu Ala Glu Asn Thr Gln Asp Val Arg Asp Asp Ile Phe
 50                  55                  60

Ile Ile Thr Tyr Pro Lys Ser Gly Thr Thr Trp Met Ile Glu Ile Ile
 65                  70                  75                  80

Cys Leu Ile Leu Lys Glu Gly Asp Pro Ser Trp Ile Arg Ser Val Pro
                 85                  90                  95

Ile Trp Glu Arg Ala Pro Trp Cys Glu Thr Ile Val Gly Ala Phe Ser
            100                 105                 110

Leu Pro Asp Gln Tyr Ser Pro Arg Leu Met Ser Ser His Leu Pro Ile
        115                 120                 125

Gln Ile Phe Thr Lys Ala Phe Phe Ser Ser Lys Ala Lys Val Ile Tyr
130                 135                 140

Met Gly Arg Asn Pro Arg Asp Val Val Ser Leu Tyr His Tyr Ser
145                 150                 155                 160

Lys Ile Ala Gly Gln Leu Lys Asp Pro Gly Thr Pro Asp Gln Phe Leu
                165                 170                 175

Arg Asp Phe Leu Lys Gly Glu Val Gln Phe Gly Ser Trp Phe Asp His
            180                 185                 190

Ile Lys Gly Trp Leu Arg Met Lys Gly Lys Asp Asn Phe Leu Phe Ile
        195                 200                 205

Thr Tyr Glu Glu Leu Gln Gln Asp Leu Gln Gly Ser Val Glu Arg Ile
210                 215                 220
```

```
Cys Gly Phe Leu Gly Arg Pro Leu Gly Lys Glu Ala Leu Gly Ser Val
225                 230                 235                 240

Val Ala His Ser Thr Phe Ser Ala Met Lys Ala Asn Thr Met Ser Asn
                245                 250                 255

Tyr Thr Leu Leu Pro Pro Ser Leu Leu Asp His Arg Arg Gly Ala Phe
            260                 265                 270

Leu Arg Lys Gly Val Cys Gly Asp Trp Lys Asn His Phe Thr Val Ala
        275                 280                 285

Gln Ser Glu Ala Phe Asp Arg Ala Tyr Arg Lys Gln Met Arg Gly Met
    290                 295                 300

Pro Thr Phe Pro Trp Asp Glu Pro Glu Glu Asp Gly Ser Pro Asp
305                 310                 315                 320

Pro Glu Pro Ser Pro Glu Pro Lys Pro Ser Leu Glu Pro Asn
                325                 330                 335

Thr Ser Leu Glu Arg Glu Pro Arg Pro Asn Ser Ser Pro Ser Pro Ser
                340                 345                 350

Pro Gly Gln Ala Ser Glu Thr Pro His Pro Arg Pro Ser
                355                 360                 365

<210> SEQ ID NO 75
<211> LENGTH: 377
<212> TYPE: PRT
<213> ORGANISM: Homo sapiens

<400> SEQUENCE: 75

Met His Asp Glu Val Ala Gln Pro Leu Asn Leu Ser Ala Lys Pro Lys
1               5                   10                  15

Thr Ser Asp Gly Lys Ser Pro Thr Ser Pro Thr Ser Pro His Met Pro
                20                  25                  30

Ala Leu Arg Ile Asn Ser Gly Ala Gly Pro Leu Lys Ala Ser Val Pro
            35                  40                  45

Ala Ala Leu Ala Ser Pro Ser Ala Arg Val Ser Thr Ile Gly Tyr Leu
    50                  55                  60

Asn Asp His Asp Ala Val Thr Lys Ala Ile Gln Glu Ala Arg Gln Met
65                  70                  75                  80

Lys Glu Gln Leu Arg Arg Glu Gln Gln Val Leu Asp Gly Lys Val Ala
                85                  90                  95

Val Val Asn Ser Leu Gly Leu Asn Asn Cys Arg Thr Glu Lys Glu Lys
            100                 105                 110

Thr Thr Leu Glu Ser Leu Thr Gln Gln Leu Ala Val Lys Gln Asn Glu
        115                 120                 125

Glu Gly Lys Phe Ser His Ala Met Met Asp Phe Asn Leu Ser Gly Asp
    130                 135                 140

Ser Asp Gly Ser Ala Gly Val Ser Glu Ser Arg Ile Tyr Arg Glu Ser
145                 150                 155                 160

Arg Gly Arg Gly Ser Asn Glu Pro His Ile Lys Arg Pro Met Asn Ala
                165                 170                 175

Phe Met Val Trp Ala Lys Asp Glu Arg Arg Lys Ile Leu Gln Ala Phe
            180                 185                 190

Pro Asp Met His Asn Ser Asn Ile Ser Lys Ile Leu Gly Ser Arg Trp
        195                 200                 205

Lys Ala Met Thr Asn Leu Glu Lys Gln Pro Tyr Tyr Glu Glu Gln Ala
    210                 215                 220

Arg Leu Ser Lys Gln His Leu Glu Lys Tyr Pro Asp Tyr Lys Tyr Lys
```

```
             225                 230                 235                 240
     Pro Arg Pro Lys Arg Thr Cys Leu Val Asp Gly Lys Lys Leu Arg Ile
                         245                 250                 255

Gly Glu Tyr Lys Ala Ile Met Arg Asn Arg Arg Gln Glu Met Arg Gln
                         260                 265                 270

Tyr Phe Asn Val Gly Gln Ala Gln Ile Pro Ile Ala Thr Ala Gly
                     275                 280                 285

Val Val Tyr Pro Gly Ala Ile Ala Met Ala Gly Met Pro Ser Pro His
                 290                 295                 300

Leu Pro Ser Glu His Ser Ser Val Ser Ser Pro Glu Pro Gly Met
     305                 310                 315                 320

Pro Val Ile Gln Ser Thr Tyr Gly Val Lys Gly Glu Pro His Ile
                         325                 330                 335

Lys Glu Glu Ile Gln Ala Glu Asp Ile Asn Gly Glu Ile Tyr Asp Glu
                     340                 345                 350

Tyr Asp Glu Glu Glu Asp Asp Pro Asp Val Asp Tyr Gly Ser Asp Ser
                 355                 360                 365

Glu Asn His Ile Ala Gly Gln Ala Asn
         370                 375

<210> SEQ ID NO 76
<211> LENGTH: 307
<212> TYPE: PRT
<213> ORGANISM: Homo sapiens

<400> SEQUENCE: 76

Met Ser Lys Arg Lys Leu Ile Pro Lys Leu Ser Ile Gln Ser Pro Val
     1               5                   10                  15

Leu His Thr Asn Leu Asn Val Gln Ser Thr His Pro Pro Leu Lys Lys
                     20                  25                  30

Glu Asp Leu His Arg Ile Ser Lys Asp Ser Leu Glu Ser Asp Ser Glu
                 35                  40                  45

Ser Leu Thr Gln Glu Ile Met Cys His Ser Glu Phe Asp Asp Arg Ile
     50                  55                  60

Arg Gly Asn Gly Met Glu Pro Asp Ser Leu Asp Glu Glu Glu Ser Pro
     65                  70                  75                  80

Arg Trp Gly Ser Leu His Glu Met Glu Glu Ala Ser Gly Lys Ala
                     85                  90                  95

Ala Gln Met Ala Arg Glu Gln Asn His His Thr Trp Asp Gln Gly Ala
                 100                 105                 110

Asn Asn Arg Gln Gln Pro Ile Glu Asp Lys Tyr Ser Asp Leu Arg Tyr
                 115                 120                 125

Asp Pro Asn Trp Lys Ser Lys Lys Glu Glu Gly Gln Leu Leu Ser Val
                 130                 135                 140

Glu Ala Leu Pro Glu Ser Thr Asp Ser Ser Leu Glu Asn Leu Pro Leu
     145                 150                 155                 160

Ala Pro Leu Tyr Pro Ser Gln Glu Thr Ser Met Glu Leu Ser Gly Gly
                         165                 170                 175

Lys Gly Glu Gln Lys Glu Ser Pro Gln Ser Ala Ala Ser Leu Leu Gly
                     180                 185                 190

Ser Glu Phe Leu Ser Pro Asn Tyr Glu His Gly Ala Arg Arg Ser Lys
                 195                 200                 205

Pro Phe Ser Glu Leu Ser Asp Ser Asp Leu Glu Glu Lys Ser Ser Ser
                 210                 215                 220
```

```
Leu Ser Pro Tyr Val Lys Ser Ser Ser His Asn Glu Val Phe Leu
225                 230                 235                 240

Pro Gly Ser Arg Gly Pro Arg Arg Arg Lys Ser Lys Gln His Phe Val
            245                 250                 255

Glu Lys Asn Lys Leu Thr Leu Gly Leu Pro Thr Pro Lys Thr Asp Ser
            260                 265                 270

Tyr Leu Gln Leu His Asn Lys Lys Arg Gly Glu Ser His Pro Glu Gln
            275                 280                 285

Val Ile Leu Arg Val Asn Ser Leu Pro Arg Asp Gly Phe Lys Thr Phe
            290                 295                 300

Trp Ser Gln
305

<210> SEQ ID NO 77
<211> LENGTH: 107
<212> TYPE: PRT
<213> ORGANISM: Homo sapiens

<400> SEQUENCE: 77

Met Asp Ala Ile Leu Asn Tyr Arg Ser Glu Asp Thr Glu Asp Tyr Tyr
1               5                   10                  15

Thr Leu Leu Gly Cys Asp Glu Leu Ser Ser Val Glu Gln Ile Leu Ala
            20                  25                  30

Glu Phe Lys Val Arg Ala Leu Glu Cys His Pro Asp Lys His Pro Glu
            35                  40                  45

Asn Pro Lys Ala Val Glu Thr Phe Gln Lys Leu Gln Lys Ala Lys Glu
        50                  55                  60

Ile Leu Thr Asn Glu Glu Ser Arg Ala Arg Tyr Asp His Trp Arg Arg
65                  70                  75                  80

Ser Gln Met Ser Met Pro Phe Gln Trp Ala Leu Asn Asp Ser
                85                  90                  95

Val Lys Thr Val Gly Phe Ser Leu Gly Ala Thr
            100                 105

<210> SEQ ID NO 78
<211> LENGTH: 486
<212> TYPE: PRT
<213> ORGANISM: Homo sapiens

<400> SEQUENCE: 78

Met Ala Trp Ile Lys Arg Lys Phe Gly Glu Arg Pro Pro Lys Arg
1               5                   10                  15

Leu Thr Arg Glu Ala Met Arg Asn Tyr Leu Lys Glu Arg Gly Asp Gln
            20                  25                  30

Thr Val Leu Ile Leu His Ala Lys Val Ala Gln Lys Ser Tyr Gly Asn
            35                  40                  45

Glu Lys Arg Phe Phe Cys Pro Pro Cys Val Tyr Leu Met Gly Ser
        50                  55                  60

Gly Trp Lys Lys Lys Lys Glu Gln Met Glu Arg Asp Gly Cys Ser Glu
65                  70                  75                  80

Gln Glu Ser Gln Pro Cys Ala Phe Ile Gly Ile Gly Asn Ser Asp Gln
                85                  90                  95

Glu Met Gln Gln Leu Asn Leu Glu Gly Lys Asn Tyr Cys Thr Ala Lys
            100                 105                 110

Thr Leu Tyr Ile Ser Asp Ser Asp Lys Arg Lys His Phe Met Leu Ser
            115                 120                 125
```

```
Val Lys Met Phe Tyr Gly Asn Ser Asp Asp Ile Gly Val Phe Leu Ser
            130                 135                 140
Lys Arg Ile Lys Val Ile Ser Lys Pro Ser Lys Lys Gln Ser Leu
145                 150                 155                 160
Lys Asn Ala Asp Leu Cys Ile Ala Ser Gly Thr Lys Val Ala Leu Phe
                165                 170                 175
Asn Arg Leu Arg Ser Gln Thr Val Ser Thr Arg Tyr Leu His Val Glu
            180                 185                 190
Gly Gly Asn Phe His Ala Ser Ser Gln Gln Trp Gly Ala Phe Phe Ile
                195                 200                 205
His Leu Leu Asp Asp Glu Ser Glu Gly Glu Phe Thr Val Arg
            210                 215                 220
Asp Gly Tyr Ile His Tyr Gly Gln Thr Val Lys Leu Val Cys Ser Val
225                 230                 235                 240
Thr Gly Met Ala Leu Pro Arg Leu Ile Ile Arg Lys Val Asp Lys Gln
                245                 250                 255
Thr Ala Leu Leu Asp Ala Asp Pro Val Ser Gln Leu His Lys Cys
            260                 265                 270
Ala Phe Tyr Leu Lys Asp Thr Glu Arg Met Tyr Leu Cys Leu Ser Gln
                275                 280                 285
Glu Arg Ile Ile Gln Phe Gln Ala Thr Pro Cys Pro Lys Glu Pro Asn
            290                 295                 300
Lys Glu Met Ile Asn Asp Gly Ala Ser Trp Thr Ile Ser Thr Asp
305                 310                 315                 320
Lys Ala Glu Tyr Thr Phe Tyr Glu Gly Met Gly Pro Val Leu Ala Pro
                325                 330                 335
Val Thr Pro Val Pro Val Val Glu Ser Leu Gln Leu Asn Gly Gly Gly
            340                 345                 350
Asp Val Ala Met Leu Glu Leu Thr Gly Gln Asn Phe Thr Pro Asn Leu
                355                 360                 365
Arg Val Trp Phe Gly Asp Val Glu Ala Glu Thr Met Tyr Arg Cys Gly
            370                 375                 380
Glu Ser Met Leu Cys Val Val Pro Asp Ile Ser Ala Phe Arg Glu Gly
385                 390                 395                 400
Trp Arg Trp Val Arg Gln Pro Val Gln Val Pro Val Thr Leu Val Arg
                405                 410                 415
Asn Asp Gly Ile Ile Tyr Ser Thr Ser Leu Thr Phe Thr Tyr Thr Pro
            420                 425                 430
Glu Pro Gly Pro Arg Pro His Cys Ser Ala Ala Gly Ala Ile Leu Arg
                435                 440                 445
Ala Asn Ser Ser Gln Val Pro Pro Asn Glu Ser Asn Thr Asn Ser Glu
450                 455                 460
Gly Ser Tyr Thr Asn Ala Ser Thr Asn Ser Thr Ser Val Thr Ser Ser
465                 470                 475                 480
Thr Ala Thr Val Val Ser
                485

<210> SEQ ID NO 79
<211> LENGTH: 82
<212> TYPE: PRT
<213> ORGANISM: Homo sapiens
```

```
<400> SEQUENCE: 79

Met Ser Gln Ala Gly Ala Gln Glu Ala Pro Ile Lys Lys Lys Arg Pro
1               5                   10                  15

Pro Val Lys Glu Glu Asp Leu Lys Gly Ala Arg Gly Asn Leu Thr Lys
                20                  25                  30

Asn Gln Glu Ile Lys Ser Lys Thr Tyr Gln Val Met Arg Glu Cys Glu
            35                  40                  45

Gln Ala Gly Ser Ala Ala Pro Ser Val Phe Ser Arg Thr Arg Thr Gly
        50                  55                  60

Thr Glu Thr Val Phe Glu Lys Pro Lys Ala Gly Pro Thr Lys Ser Val
65                  70                  75                  80

Phe Gly

<210> SEQ ID NO 80
<211> LENGTH: 129
<212> TYPE: PRT
<213> ORGANISM: Homo sapiens

<400> SEQUENCE: 80

Met Glu Asp Ala Leu Asp Glu Leu Ile Lys Asp Cys Ala Gln Gln Leu
1               5                   10                  15

Phe Glu Leu Thr Asp Asp Lys Glu Asn Glu Arg Leu Ala Tyr Val Thr
                20                  25                  30

Tyr Gln Asp Ile His Ser Ile Gln Ala Phe His Glu Gln Ile Val Ile
            35                  40                  45

Ala Val Lys Ala Pro Ala Glu Thr Arg Leu Asp Val Pro Ala Pro Arg
        50                  55                  60

Glu Asp Ser Ile Thr Val His Ile Arg Ser Thr Asn Gly Pro Ile Asp
65                  70                  75                  80

Val Tyr Leu Cys Glu Val Glu Gln Gly Gln Thr Ser Asn Lys Arg Ser
                85                  90                  95

Glu Gly Val Gly Thr Ser Ser Ser Glu Ser Thr His Pro Glu Gly Pro
            100                 105                 110

Glu Glu Glu Glu Asn Pro Gln Gln Ser Glu Glu Leu Leu Glu Val Ser
        115                 120                 125

Asn
```